(12) United States Patent
Blumberg et al.

(10) Patent No.: US 9,656,961 B2
(45) Date of Patent: *May 23, 2017

(54) METHODS FOR TREATING DEPRESSIVE SYMPTOMS

(71) Applicant: Alkermes Pharma Ireland Limited, Dublin (IE)

(72) Inventors: Laura Cook Blumberg, Lincoln, MA (US); Daniel R. Deaver, Franklin, MA (US); David J. Eyerman, Wayland, MA (US); Thomas Andrew Wynn, Lexington, MA (US)

(73) Assignee: ALKERMES PHARMA IRELAND LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 14/286,499

(22) Filed: May 23, 2014

(65) Prior Publication Data

US 2015/0072971 A1    Mar. 12, 2015

Related U.S. Application Data

(60) Provisional application No. 61/827,295, filed on May 24, 2013, provisional application No. 61/827,317, filed on May 24, 2013.

(51) Int. Cl.
| | | |
|---|---|---|
| *A61K 31/44* | (2006.01) |
| *C07D 221/28* | (2006.01) |
| *A61K 31/485* | (2006.01) |
| *C07D 211/62* | (2006.01) |
| *C07D 217/04* | (2006.01) |
| *C07D 221/22* | (2006.01) |
| *C07D 223/04* | (2006.01) |
| *C07D 401/12* | (2006.01) |
| *C07D 405/12* | (2006.01) |
| *C07D 489/00* | (2006.01) |
| *C07D 489/09* | (2006.01) |

(52) U.S. Cl.
CPC .......... *C07D 221/28* (2013.01); *A61K 31/485* (2013.01); *C07D 211/62* (2013.01); *C07D 217/04* (2013.01); *C07D 221/22* (2013.01); *C07D 223/04* (2013.01); *C07D 401/12* (2013.01); *C07D 405/12* (2013.01); *C07D 489/00* (2013.01); *C07D 489/09* (2013.01)

(58) Field of Classification Search
CPC ........................... A61K 31/407; A61K 31/485
USPC ........................................................ 514/289
See application file for complete search history.

(56) References Cited

U.S. PATENT DOCUMENTS

| | | |
|---|---|---|
| 3,332,950 A | 7/1967 | Blumberg et al. |
| 3,856,795 A | 12/1974 | Yardley |
| 3,957,793 A | 5/1976 | Wentland et al. |
| 4,032,529 A | 6/1977 | Wentland et al. |
| 4,100,288 A | 7/1978 | Merz et al. |
| RE29,943 E | 3/1979 | Wentland et al. |
| 4,161,597 A | 7/1979 | Olofson et al. |
| 4,176,186 A | 11/1979 | Goldberg et al. |
| 4,205,171 A | 5/1980 | Albertson |
| 4,374,139 A | 2/1983 | Mohacsi |
| 4,451,470 A | 5/1984 | Ganti |
| 4,464,378 A | 8/1984 | Hussain |
| 4,473,573 A | 9/1984 | Merz et al. |
| 4,489,079 A | 12/1984 | Giudice et al. |
| 4,649,200 A | 3/1987 | Portoghese et al. |
| 4,929,622 A | 5/1990 | Allen et al. |
| 5,258,386 A | 11/1993 | Newman et al. |
| 5,607,941 A | 3/1997 | Merz et al. |
| 5,847,142 A | 12/1998 | Mudryk et al. |
| 6,365,594 B1 | 4/2002 | Dondio et al. |
| 6,784,187 B2 | 8/2004 | Wentland |
| 6,812,236 B2 | 11/2004 | Gibson et al. |
| 6,887,998 B2 | 5/2005 | Wentland |
| 7,244,866 B2 | 7/2007 | Carson et al. |
| 7,262,298 B2 | 8/2007 | Wentland |
| 7,265,226 B2 | 9/2007 | Wentland |
| 7,557,119 B2 | 7/2009 | Wentland |
| 7,956,187 B2 | 6/2011 | Wentland |
| 8,026,252 B2 | 9/2011 | Wentland |
| 8,252,929 B2 | 8/2012 | Wentland |
| 8,354,534 B2 | 1/2013 | Arnelle et al. |
| 8,642,615 B2 | 2/2014 | Wentland |
| 8,680,112 B2 | 3/2014 | Wentland |
| 8,778,960 B2 | 7/2014 | Deaver et al. |
| 8,802,655 B2 | 8/2014 | Wentland |

(Continued)

FOREIGN PATENT DOCUMENTS

| | | |
|---|---|---|
| EP | 0254120 A2 | 1/1988 |
| EP | 0632041 A1 | 1/1995 |
| EP | 1359146 B1 | 4/2008 |
| ES | 2121553 B1 | 6/1999 |
| GB | 874217 A | 8/1961 |

(Continued)

OTHER PUBLICATIONS

U.S. Appl. No. 14/833,334, filed Aug. 24, 2015, Laura Blumberg.
U.S. Appl. No. 14/286,499, filed May 23, 2014, Laura Blumberg.
Alkermes: "Alkermes Initiates Clinical Study of ALKS 5461 for Treatment-Resistant Depression," Retrieved from the internet: URL: http://www.pipelinereview.com/index.php/2011061543020/Small-Molecules/Alkermes-Initiates-Clinical-Study-of-ALKS-5461-for-Treatment-Resistant-Depression.html (Jun. 2011).

(Continued)

*Primary Examiner* — Kevin E Weddington
(74) *Attorney, Agent, or Firm* — Lathrop & Gage LLP; Brian C. Trinque

(57) ABSTRACT

The present application relates methods for treating a depressive symptom comprising administering an effective amount of a μ opioid receptor agonist or a pharmaceutically acceptable salt thereof to a subject in need thereof. Non-limiting examples of such agonist include the compounds of Formulas I, II, III, and IV, as well as the compounds of Table A.

19 Claims, 9 Drawing Sheets

(56) References Cited

U.S. PATENT DOCUMENTS

| | | | |
|---|---|---|---|
| 8,822,488 | B2 | 9/2014 | Deaver et al. |
| 9,133,125 | B2* | 9/2015 | Blumberg ............ A61K 31/485 |
| 9,211,293 | B2* | 12/2015 | Deaver ................ A61K 31/485 |
| 2002/0099216 | A1 | 7/2002 | Gibson et al. |
| 2003/0181475 | A1 | 9/2003 | Kaiko et al. |
| 2004/0192715 | A1 | 9/2004 | Chasin et al. |
| 2004/0254208 | A1 | 12/2004 | Weber et al. |
| 2005/0113401 | A1 | 5/2005 | Lawson |
| 2005/0176645 | A1 | 8/2005 | Mickle et al. |
| 2005/0182258 | A1 | 8/2005 | Schmidhammer et al. |
| 2005/0215799 | A1 | 9/2005 | Wentland et al. |
| 2006/0030580 | A1 | 2/2006 | Wentland |
| 2006/0063792 | A1 | 3/2006 | Dolle et al. |
| 2007/0021457 | A1 | 1/2007 | Wentland |
| 2007/0099947 | A1 | 5/2007 | Dean et al. |
| 2007/0238748 | A1 | 10/2007 | Wentland |
| 2008/0004324 | A1 | 1/2008 | Barak |
| 2008/0234306 | A1 | 9/2008 | Perez et al. |
| 2009/0053329 | A1 | 2/2009 | Peters et al. |
| 2009/0197905 | A1 | 8/2009 | Wentland |
| 2009/0209569 | A1 | 8/2009 | Arnelle et al. |
| 2009/0247562 | A1 | 10/2009 | Wentland |
| 2009/0311347 | A1 | 12/2009 | Oronsky |
| 2010/0035910 | A1 | 2/2010 | Wang et al. |
| 2010/0048906 | A1 | 2/2010 | Wang et al. |
| 2010/0130512 | A1 | 5/2010 | Wentland |
| 2010/0190817 | A1 | 7/2010 | Wentland |
| 2010/0240691 | A1 | 9/2010 | Turncliff et al. |
| 2011/0136848 | A1 | 6/2011 | Silverman |
| 2012/0010412 | A1 | 1/2012 | Duncan |
| 2013/0231361 | A1 | 9/2013 | Wentland |
| 2013/0281388 | A1 | 10/2013 | Deaver |
| 2015/0045384 | A1 | 2/2015 | Blumberg et al. |

FOREIGN PATENT DOCUMENTS

| | | |
|---|---|---|
| GB | 1340720 A | 12/1973 |
| JP | 40010154 B4 | 5/1965 |
| WO | WO 9311761 A1 | 6/1993 |
| WO | WO 9725331 A1 | 7/1997 |
| WO | WO 9852929 A1 | 11/1998 |
| WO | WO 0112197 A1 | 2/2001 |
| WO | WO 0236573 A2 | 5/2002 |
| WO | WO 03101963 A1 | 12/2003 |
| WO | WO 2004005294 A2 | 1/2004 |
| WO | WO 2004007449 A1 | 1/2004 |
| WO | WO 2004045562 A2 | 6/2004 |
| WO | WO 2006052710 A1 | 5/2006 |
| WO | WO 2006096626 A2 | 9/2006 |
| WO | WO 2007014137 A2 | 2/2007 |
| WO | WO 2007089934 A2 | 8/2007 |
| WO | WO 2008144394 A2 | 11/2008 |
| WO | WO 2009023567 A1 | 2/2009 |
| WO | WO 2010011619 A1 | 1/2010 |
| WO | WO 2010107457 A1 | 9/2010 |
| WO | WO 2010141666 A2 | 9/2010 |
| WO | WO 2011119605 A2 | 9/2011 |
| WO | WO 2012088494 A1 | 6/2012 |
| WO | 2014190270 A1 | 11/2014 |
| WO | 2014190271 A2 | 11/2014 |

OTHER PUBLICATIONS

Alkermes: "Strong Results for Alkermes' ALKS 5461 in Major Depressive Disorder," Retrieved from the internet: URL: http://www.thepharmaletter.com/file/109997/strong-results-for-alkermes-alks-5461-in-major-depressive-disorder.html (Jan. 2012).

Belluzzi, J.D., et al., "Enkephalin May Mediate Euphoria and Drive-Reduction Reward," Nature, 266, pp. 556-558 (Apr. 1977).

Berge, S.M., et al. "Pharmaceutical Salts"; 1977; Journal of Pharmaceutical Sciences; 66(1): 1-19.

Bianchetti, A., et al., "Quaternary Derivatives of Narcotic Antagonists: Stereochemical Requirements at the Chiral Nitrogen for in vitro and in vivo Activity," Life Sciences, 33(Suppl 1), pp. 415-418 (1983).

Bianchi, G., et al., "Quaternary Narcotic Antagonists' Relative Ability to Prevent Antinociception and Gastrointestinal Transit Inhibition in Morphine-Treated Rats as an Index of Peripheral Selectivity," Life Sciences, 30(22): pp. 1875-1883 (1982).

Bidlack, J.M., et. al., "8-Carboxamidocyclazocine: a long-acting, novel benzomorphan," J. Pharmacol. Exp. Ther.. Jul. 2002; 302(1):374-80.

Cacchi, S., et al., "Palladium-Catalyzed Carbonylation of Aryl Triflates," Tetrahedron Ltrs., 27, pp. 3931-3934 (1986).

Cao, X., et al., "Why is it Challenging to Predict Intestinal Drug Absorption and Oral Bioavailability in Human Using Rat Model," Pharmaceutical Research, 23(8), pp. 1675-1686 (Aug. 2006).

Darwin, W.D., et al., "Fluorescence Properties of Pseudomorphine and Congeners: Structure-Activity Relationships," Journal of Pharmaceutical Sciences, 1980, vol. 69, p. 253-257.

Coop, A., et al., "Direct and Simple Conversion of Codeine to Thebainon-A and Dihydrothebainone," Heterocycles, vol. 50, No. 1, pp. 39-42 (1999).

Coop, A., et al., "δ Opioid Affinity and Selectivity of 4-Hydroxy-3-methoxyindolomorphinan Analogues Related to Naltrindole," J. Med. Chem. 1999, 42, pp. 1673-1679.

Danso-Danquah, R., et al., "Synthesis and σ Binding Properties of 1'-and 3'-Halo-and 1',3'-Dihalo-N-normetazocine Analogues," J. Med. Chem., 38, 2986-2989 (1995).

Davies, S.G., et al., "Palladium Catalysed Elaboration of Codeine and Morphine," J. Chem. Soc. Perkin Trans., 1 pp. 1413-1420 (2001).

Díaz, N., et al., "SAR & Biological Evaluation of Novel trans-3,4-dimethyl-4-arylpiperidine Derivatives as Opioid Antagonists," Bioorganic & Medicinal Chemistry Letters 15, pp. 3844-3848 (2005).

Elman, I., et al., "Food Intake and Reward Mechanisms in Patients with Schizophrenia: Implications for Metabolic Disturbances and Treatment with Second-Generation Antipsychotic Agents," Neuropsychopharmacology 31, pp. 2091-2120 (2006).

Garriock, H.A., et al., "Association of Mu-Opioid Receptor Variants and Response to Citalopram Treatment in Major Depressive Disorder," Am. J. Psychiatry 167(5): pp. 565-573 (May 2010).

Heiner, J., et al., "Efficient kg-Scale Synthesis of Thrombin Inhibitor CRC 220," Tetrahedron, vol. 51, No. 44, pp. 12047-12068 (1995).

Huidobro-Toro, J.P., et al., Comparative Study on the Effect of Morphine and the Opioid-Like Peptides in the Vas Deferens of Rodents: Species and Strain Differences, Evidence for Multiple Opiate Receptors, Life Sciences vol. 28, pp. 1331-1336 (1981).

Ida, H., "The Nonnarcotic Antitussive Drug Dimemorfan: A Review," Clinical Therapeutics, vol. 19, No. 2, pp. 215-231 (1997).

Gross-Isseroff, R., et al., "Regionally Selective Increases in μ Opioid Receptor Density in the Brains of Suicide Victims," Brain Research 530, pp. 312-316 (1990).

Kennedy, S.E., et al., "Dysregulation of Endogenous Opioid Emotion Regulation Circuitry in Major Depression in Women," Arch Gen Psychiatry 63, pp. 1199-1208 (Nov. 2006).

Ko, M.C., et al., "Differentiation of kappa opioid agonist-induced antinociception by naltrexone apparent pA2 analysis in rhesus monkeys," J Pharmacol Exp Ther. May 1998;285(2):518-26.

Kubota, H., et al., "Palladium-Catalyzed Cyanation of Hindered, Electron-Rich Aryl Triflates by Zinc Cyanide", Tetrahedron Lett. 39, 2907-2910 (1998).

Kubota, H., et al., "Synthesis and Biological Activity of 3-Substituted 3-Desoxynaltrindole Derivatives", Bioorg. Med. Chem. Lett. 8, 799-804 (1998).

Mohacsi, E., et al., "Acylmorphinans. A Novel Class of Potent Analgesic Agents," J. Med. Chem. 1985, 28(9), pp. 1177-1180.

Morera, E., et al., "A Palladium-Catalyzed Carbonylative Route to Primary Amides," Tetrahedron Lett. 39, pp. 2835-2838 (1998).

(56) References Cited

OTHER PUBLICATIONS

Nan, Y., et al., "Synthesis of 2'-Amino-17-cyclopropylmethyl-6 7-dehydro-3, 14-dihydroxy-4, 5α-epoxy-6,7:4',5'-thiazolomorphinan from Naltrexone[1]," J. Heterocyclic Chem., 34, pp. 1195-1203 (1997).

Neumeyer, J.L., et al., "Design and Synthesis of Novel Dimeric Morphinan Ligands for κ and μ Opioid Receptors," J. Med. Chem., 46, pp. 5162-5170 (2003).

Rennison, D., et al., "Structural Determinants of Opioid Activity in Derivatives of 14-Aminomorphinones: Effects of Changes to the Chain Linking of the C14-Amino Group to the Aryl Ring," Journal of Medicinal Chemistry 49(20): pp. 6104-6110 (2006).

Saal, C., "Pharmaceutical Salts Optimization of Solubility or Even More?," American Pharmaceutical Review, pp. 1-6, http://www.americanpharmaceuticalreview.com/ (Mar. 2010).

Sayre, L.M., et. al., "Design and Synthesis of Naltrexone-Derived Affinity Labels with Nonequilibrium Opioid Agonist and Antagonist Activities. Evidence for the Existence of Different μ Receptor Subtypes in Different Tissues," J. Medicinal Chemistry, 1984, 27: 1325-1335.

Schultz, J.E.J., et al. 2001, "Opioids and cardioprotection." Pharmacology & Therapeutics, vol. 89, pp. 123-137.

Simpkins, J.W., et al., "Evaluation of the Sites of Opioid Influence on Anterior Pituitary Hormone Secretion Using a Quaternary Opiate Antagonist," Neuroendocrinology, 54(4): pp. 384-390 (1991).

Todtenkopf, M.S., et al., "In vivo Characterization of Novel, Peripherally-Acting Opioid Antagonists," Society for Neuroscience Abstract Viewer and Itinerary Planner, vol. 38, 38th Annual Meeting of the Society for Neuroscience, Nov. 2008.

Vanalstine, M., et al., "Redefining the Structure-Activity Relationships of 2,6-methano-3-benzazocines.5. Opioid Receptor Binding Properties of [N-(4'-phenyl)-phenethyl) Analogues of 8-CAC," Bioorganic & Medicinal Chemistry Letters, vol. 17, No. 23, pp. 6516-6520 (Nov. 2, 2007).

Vanalstine M., "Design, Synthesis and Evalulation of Novel N-substituted Derivatives of 8-Carboxamidocyclazocine," Thesis (Ph.D.)—Rensselaer Polytechnic Institute, Apr. 2007, pp. 1-215.

Wentland, M.P., et al., "8-Aminocyclazocine Analogues: Synthesis and Structure-Activity Relationships", Bioorg. Med. Chem. Ltrs. 10(2), pp. 183-187 (2000).

Wentland, M.P., et al., "8-Carboxamidocyclazocine Analogues: Redefining the Structure-Activity Relationships of 2,6 Methano-3-benzazocines", Bioorg. Med. Chem. Ltrs, 11(5), pp. 623-626 (2001).

Wentland, M.P., et al., "Syntheses and Opioid Receptor Binding Affinities of 8-Amino-2,6-methano-3-benzazocines," Journal of Medicinal Chemistry, 2003, pp. 838-849, vol. 46, No. 5.

Wentland, M.P., et al., "Synthesis and Opioid Receptor Binding Properties of Highly Potent 4-hydroxy Analogue of Naltrexone," Bioorg. Med. Chem. Lett. 15(8): pp. 2107-2110 (2005).

Wentland, M., et al., "Redefining the Structure-Activity Relationships of 2,6-methano-3-benzazocines. Part 3: 8-Thiocarboxamido and 8-thioformamido Derivatives of Cyclazocine," Bioorg. Med. Chem. Lett., 15(10), pp. 2547-2551 (2005).

Wentland, M.P., et al., "Redefining the Structure-Activity Relationships of 2,6-methano-3-benzazocines.4. Opioid Receptor Binding Properties of 8-[N-(4'-phenyl)-phenethyl) carboxamidol] Analogues of Cyclazocine and Ethylketocyclazocine," Journal of Medicinal Chemistry, vol. 49, No. 18, pp. 5635-5639 (Sep. 7, 2006).

Wentland, M.P., et al., "Redefining the Structure-Activity Relationships of 2,6-methano-3-benzazocines, Part 6: Opioid Receptor Binding Properties of Cyclic Variants of 8-carboxamidocyclazocine," Bioorganic & Medicinal Chemistry, 2008, pp. 5653-5664, vol. 16, No. 10.

Wentland, M., et al., "Syntheses and Opioid Receptor Binding Properties of Carboxamido-Substituted Opioids," Bioorganic & Medicinal Chemistry 19(1): pp. 203-208 (Jan. 2009).

Wentland, M. P., et al., "Redefining the Structure-Activity Relationships of 2,6-methano-3-benzazocines, Part 7: Syntheses and Opioid Receptor Properties of Cyclic Variants of Cyclazocine," Bioorganic & Medicinal Chemistry Letters, 2009, pp. 365-368, vol. 19, No. 2.

Yamamoto, T., et al., "Buprenorphine Activates μ and Opioid Receptor Like-1 Receptors Simultaneously, but the Analgesic Effect is Mainly Mediated by μ Receptor Activation in the Rat Formalin Test," Journal of Pharmacology and Experimental Therapeutics, vol. 318, No. 1, pp. 206-213 (2006).

Zaveri, N., et. al.,"Small-Molecule Agonists and Antagonists of the Opioid Receptor-Like Receptor (ORL 1, NOP): Ligand-Based Analysis of Structural Factors Influencing Intrinsic Activity at NOP," AAPS Journal, 2005, E345-E352.

Zhang, A., et al., "10-Ketomorphinan and 3-Substituted 3-desoxymorphinan Analogues as Mixed κ and μ Opioid Ligands: Synthesis and Biological Evaluation of Their Binding Affinity at Opioid Receptors," J. Med. Chem. 47, pp. 165-174 (2004).

McCurdy, et al., "Investigation of Phenolic Bioisosterism in Opiates: 3-Sulfonamido Analogues of Naltrexone and Oxymorphone," Organic Letters, vol. 2, No. 6, pp. 819-821 (2000).

Wentland, et al., "Selective Protection and Functionalization of Morphine: Synthesis and Opioid Receptor Binding Properties of 3-Amino 3-desoxymorphine Derivatives", J. Med. Chem. 43, pp. 3558-3565 (2000).

Wentland, et al., "3-Carboxamido Analogues of Morphine and Naltrexone: Synthesis and Opioid Receptor Binding Properties", Bioorg. Med. Chem. Lett. 11(13), pp. 1717-1721 (2001).

Wentland et. al., Redefining the structure-activity relationships of 2,6-methano-3-benzazocines. Part 2: 8-formamidocyclazocine analogues, Bioorg. Med. Chem. Lett. Jun. 2, 2003;13(11):1911-4.

Wentland M.P, et al., "Syntheses of novel high affinity ligands for opioid receptors," Bioorg. Med. Chem. Lett. Apr. 15, 2009;19(8):2289-2294. Epub Feb. 25, 2009.

International Search Report and Written Opinion of the International Searching Authority for Application No. PCT/US2014/039359, dated Sep. 22, 2014 (17 pages).

International Search Report and Written Opinion of the International Searching Authority for Application No. PCT/US2014/039361, dated Sep. 29, 2014, (6 pages).

* cited by examiner

Figure 3
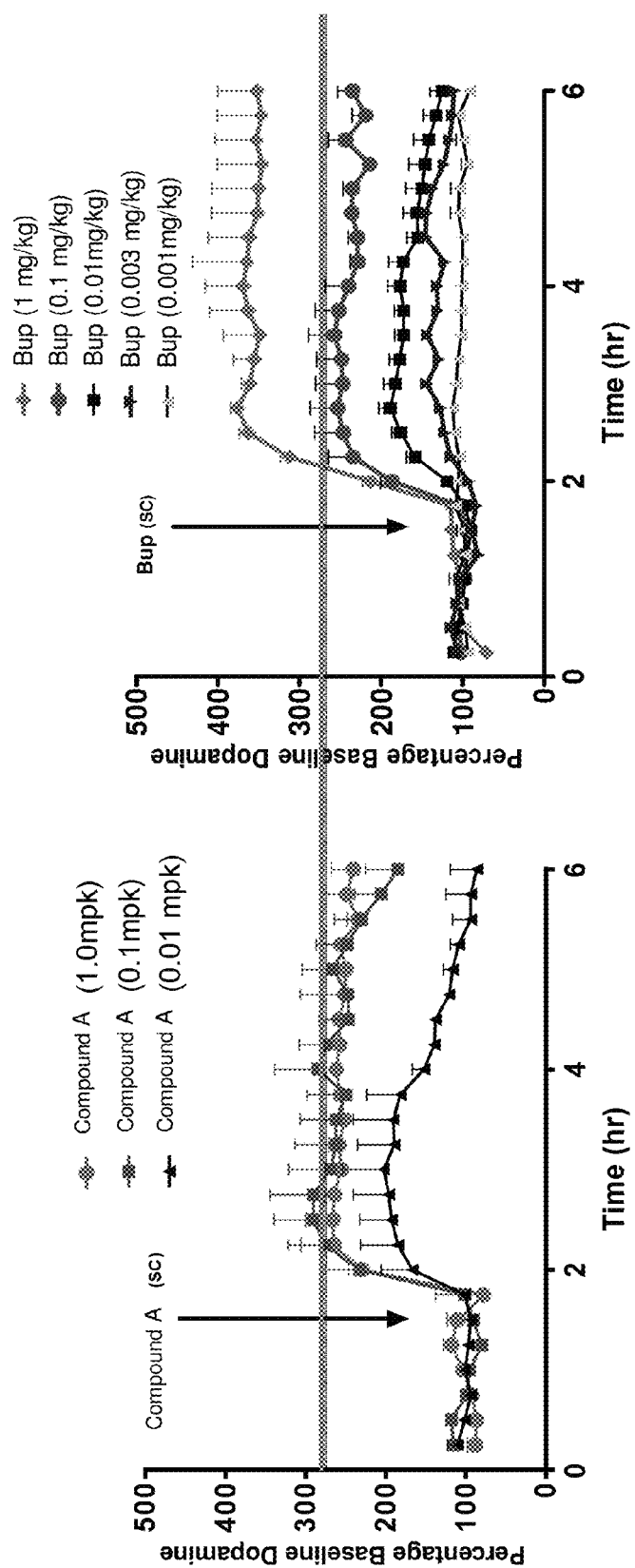
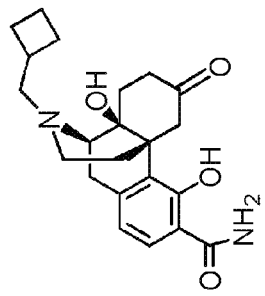
Compound A

METHODS FOR TREATING DEPRESSIVE SYMPTOMS

RELATED APPLICATIONS

This application claims priority to U.S. Provisional Application Ser. No. 61/827,295, filed May 24, 2013, and U.S. Provisional Application Ser. No. 61/827,317, filed May 24, 2013, the contents of which are incorporated herein by reference in their entireties.

BACKGROUND

Depression (also known as depressive disorders or depressive symptoms) includes common but serious disorders of the brain characterized by combinations of signs and symptoms that may include feelings of hopelessness, guilt, worthlessness, and/or sadness alongside changes in sleep and/or eating patterns. While complex depressive disorders are thought to be caused by multiple factors, it is widely accepted that these disorders generally have a neurochemical component. Current treatment regimens often consist of a combination of psychotherapy and one or more medications to regulate neurotransmitters such as dopamine, serotonin and norepinephrine.

Current pharmacological methods of treatment for depressive disorders can be efficacious, but they often have significant drawbacks. Many anti-depressants have a latency period of two to three weeks, a delay that can be life-threatening to a patient who is depressed. After this initial period, if a chosen therapeutic shows little or no effect on the symptoms of the patient, the treating physician may alter the therapeutic regimen by increasing the dosage of the chosen drug or by recommending an entirely new compound. Even after a medication proves efficacious, the patient may suffer side effects such as dizziness, weight gain, and a loss of libido. The patient may also develop a tolerance to the drug, leading them to take ever-increasing doses in order to achieve similar results. In certain cases, chemical dependence may also develop, leading to potential abuse and, in the case of abrupt discontinuation, major withdrawal (including the risk of grand mal seizures and death).

While certain treatments for depressive disorders do exist, many commonly used therapeutics suffer from significant drawbacks including inefficacy, latency periods, tolerance, and chemical dependence. There is therefore an urgent need for new and improved methods of treatment for these disorders that may be used alone or in conjunction with existing therapeutic modalities.

SUMMARY OF THE INVENTION

Provided herein are methods for treating depressive symptoms comprising administering to a subject in need thereof a µ opioid receptor agonist, e.g., a compound of Formula I, II, III, or IV, or Table A.

In one aspect, provided herein is a method of treating a depressive symptom in a subject in need thereof, which comprises administering to the subject an effective amount of a µ opioid receptor agonist that exhibits an Emax of 5% to 45% in a GTPγS binding assay. In one embodiment, the Emax is 15% to 35% in a GTPγS binding assay. In another embodiment, said agonist has a low risk of opioid dependence, opioid addiction, and/or symptoms of opioid withdrawal.

In another aspect, provided herein is a method of treating a depressive symptom in a subject in need thereof, which comprises administering to the subject an effective amount of a compound that exhibits a maximal dopamine efflux in the nucleus accumbens of 125% to 300% over base line in a rat. In particular embodiments, the compound exhibits a maximal dopamine efflux in the nucleus accumbens of 200% to 300% over base line in a rat.

In another aspect, provided herein is a method of treating a depressive symptom in a subject in need thereof, which comprises administering to the subject an effective amount of a compound that does not attenuate thermal pain in a rodent hot plate model when administered at a dose of at least 1 mg/kg. In one embodiment, the compound does not attenuate thermal pain in a rodent hot plate model when administered at a dose of at least 3 mg/kg. In another embodiment, the compound does not attenuate thermal pain in a rodent hot plate model when administered at a dose of 10 mg/kg.

In still another embodiment, provided herein is a method of treating a depressive symptom in a subject comprising administering to the subject a compound of Formula I:

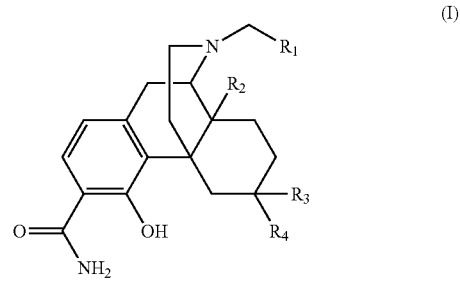

or a pharmaceutically acceptable salt thereof, wherein:

$R_1$ is cyclobutyl,

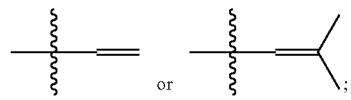

$R_2$ is H, hydroxyl, or methoxy; and $R_3$ and $R_4$ are each, independently, H, hydroxyl, or $NR_5R_6$, wherein $R_5$ and $R_6$ are each independently H, alkyl or substituted acyl, or alternatively, $R_3$ and $R_4$, together with the carbon atom to which they are attached, form C=O or C=CH$_2$.

In one embodiment of Formula I, substituted acyl is defined as follows:

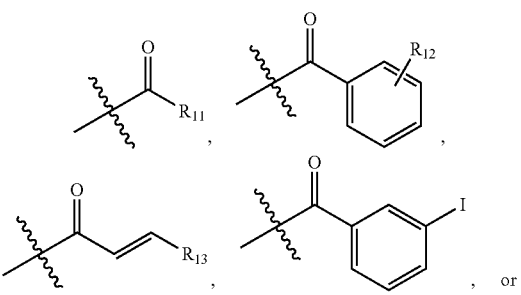

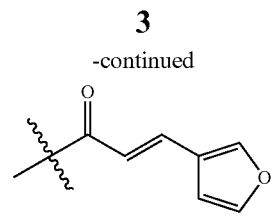
wherein $R_{11}$ is linear or branched $C_1$-$C_6$ alkyl; $R_{12}$ is halo, $C_1$-$C_6$ alkyl, or $C_1$-$C_6$ alkoxy; and $R_{13}$ is aryl or heteroaryl. In one embodiment of Formula (IV), $R_1$ is cyclopropyl.
In particular embodiments, the compound of Formula I is:
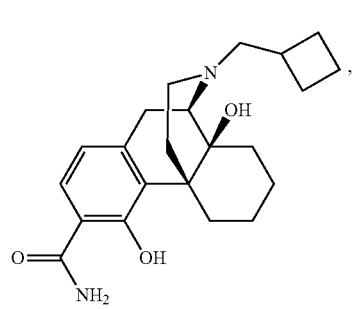
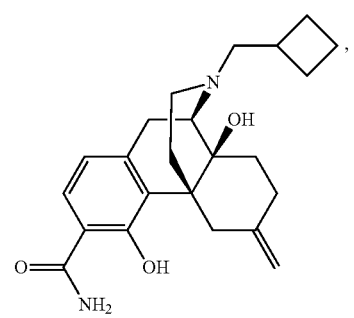
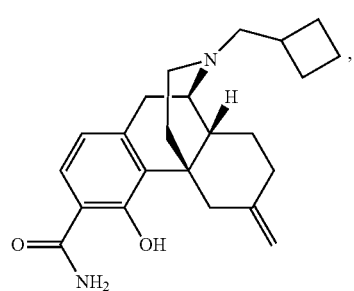
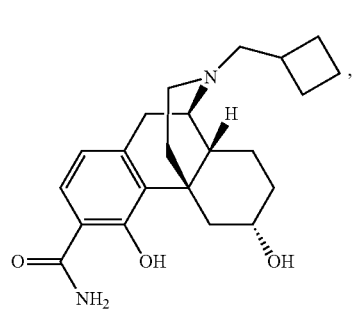
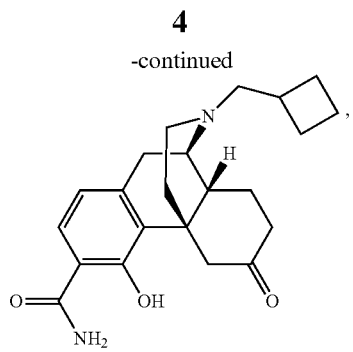
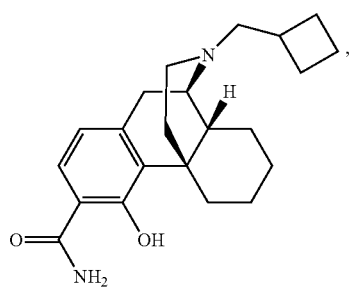
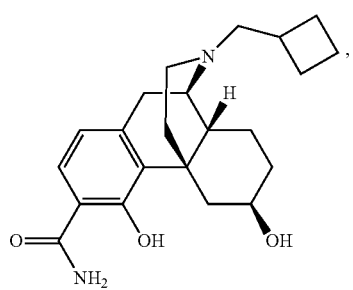
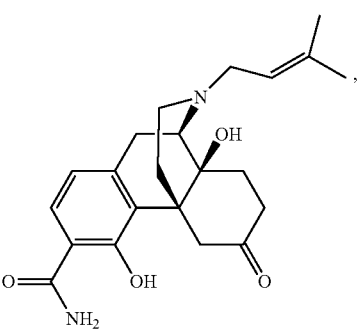
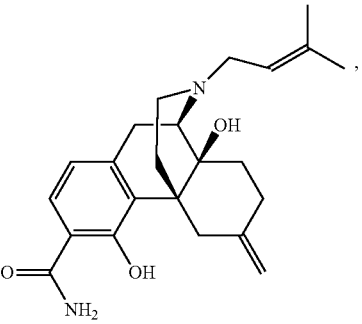

-continued

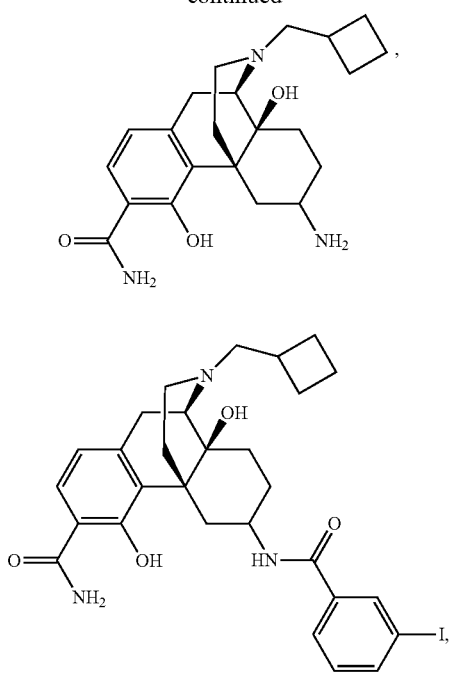

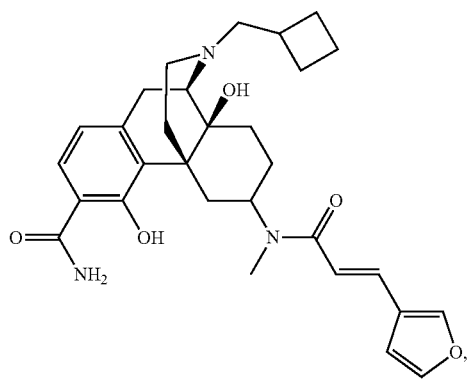

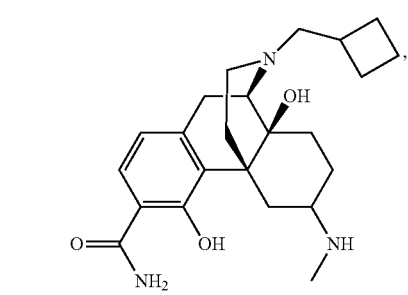

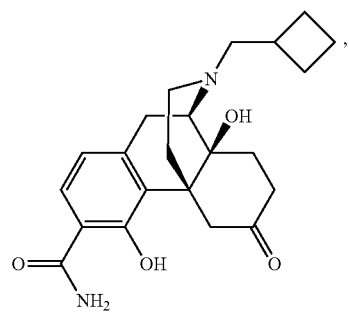

-continued

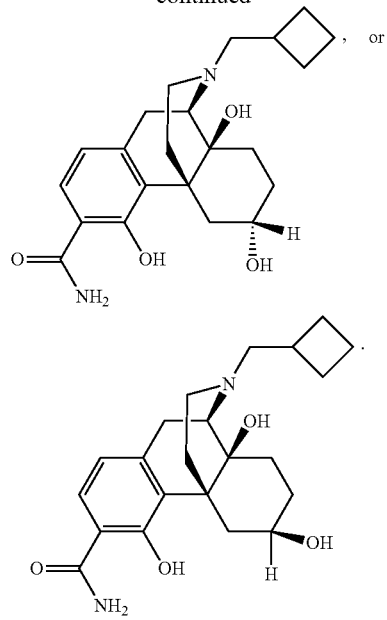

In another aspect, provided herein is a method of treating a depressive symptom in a subject comprising administering to the subject a compound of Formula II:

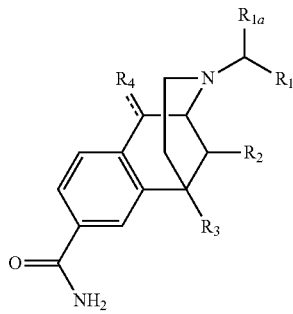

(II)

or a pharmaceutically acceptable salt thereof, wherein:

$R_1$ is $C_1$-$C_6$ alkyl, $C_2$-$C_6$ alkenyl, cycloalkyl, heterocyclyl, hydroxyalkyl, or alkoxyalkyl;

$R_{1a}$ is H or methyl;

$R_2$ and $R_3$ are each methyl, or alternatively, $R_2$ and $R_3$, together with the carbon atoms to which they are attached, form a 6-membered unsubstituted carbocyclic ring;

when ----- is a single bond, $R_4$ is H; and when ----- is a double bond, $R_4$ is O.

In particular embodiment, the compound of Formula II is:

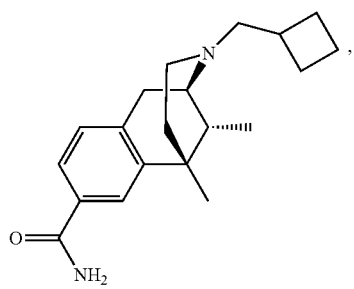

7
-continued
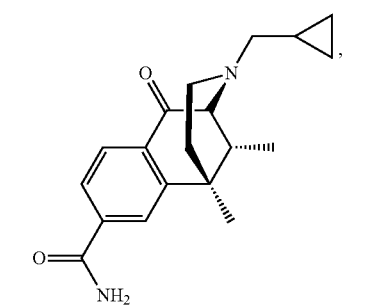
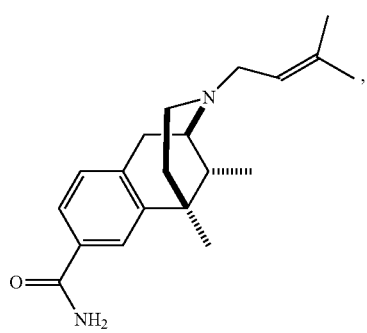
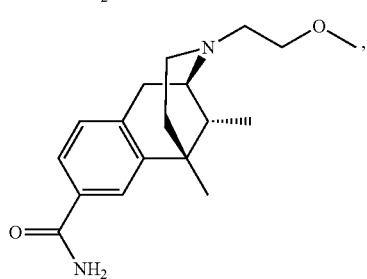
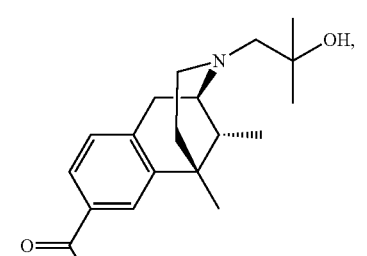
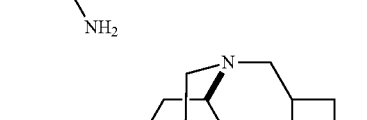
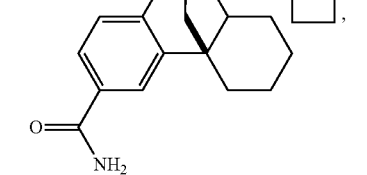
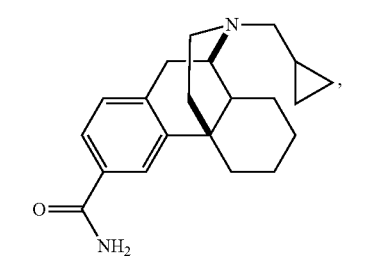
8
-continued
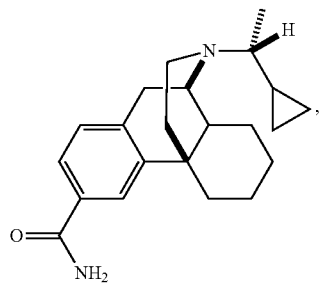
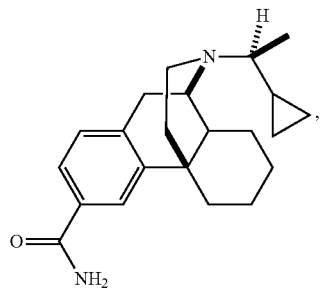
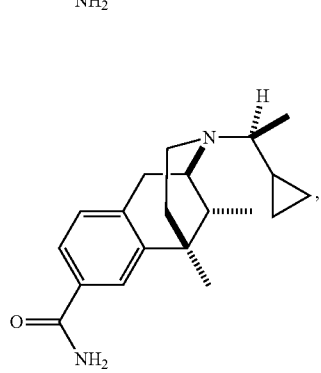
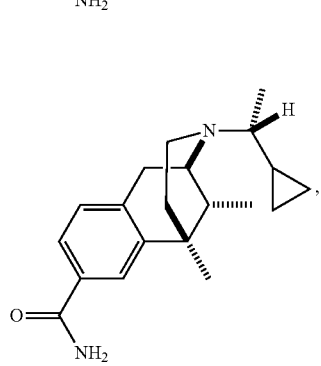
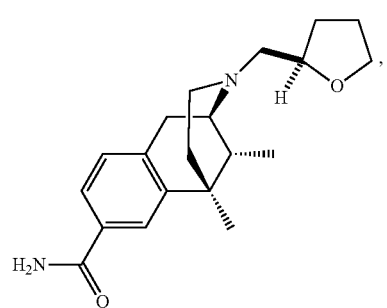

-continued

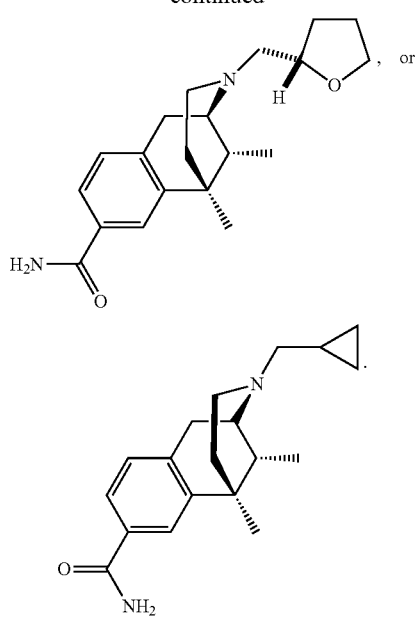

Also provided herein is a method of treating a depressive symptom in a subject comprising administering to the subject a compound of Formula III:

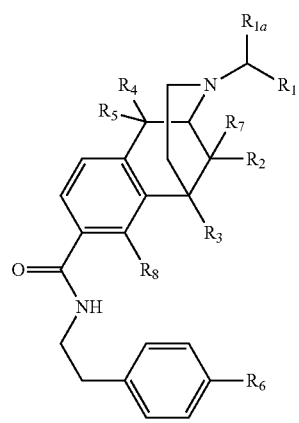

or a pharmaceutically acceptable salt thereof, wherein:

$R_1$ is $C_1$-$C_6$ alkyl, $C_2$-$C_6$ alkenyl, aryl, cycloalkyl, heterocyclyl, benzyl, hydroxyalkyl, or alkoxyalkyl;

$R_{1a}$ is H or methyl;

$R_2$ and $R_3$ are each H, methyl, or ethyl, or alternatively, $R_2$ and $R_3$, together with the carbon atoms to which they are attached, form a 6-membered unsubstituted carbocyclic ring or carbonyl-substituted carbocyclic ring;

$R_4$ and $R_5$ are each, independently, H, hydroxyl, or $C_1$-$C_6$ alkyl;

$R_6$ is unsubstituted or substituted $C_6$-$C_{10}$ aryl, or substituted or unsubstituted heteroaryl comprising one or two 5- or 6-membered rings and 1-4 heteroatoms selected from N, O and S; and $R_7$ and $R_8$ are each, independently, H or hydroxyl.

In particular embodiment, the compound of Formula III is:

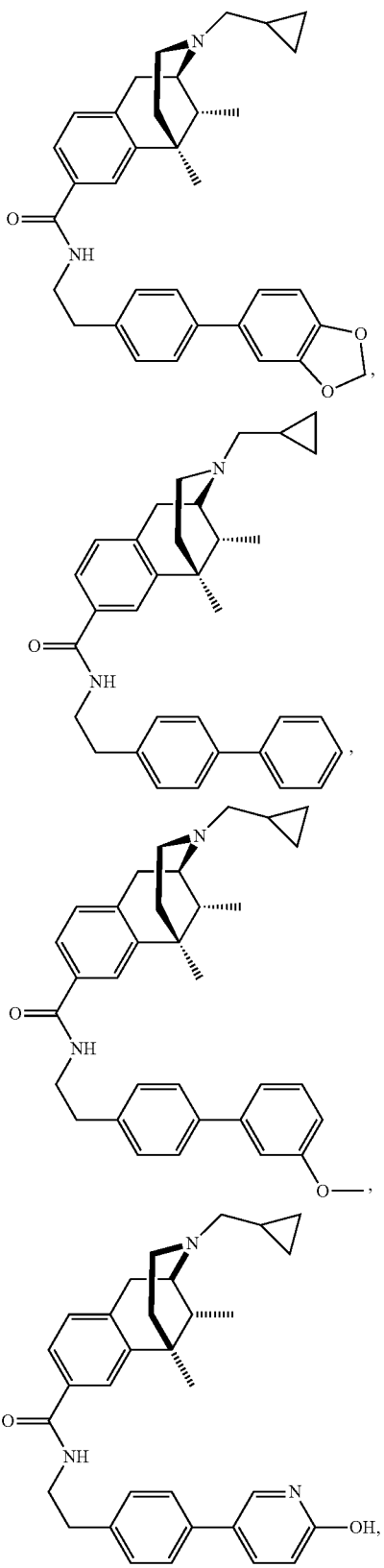

-continued

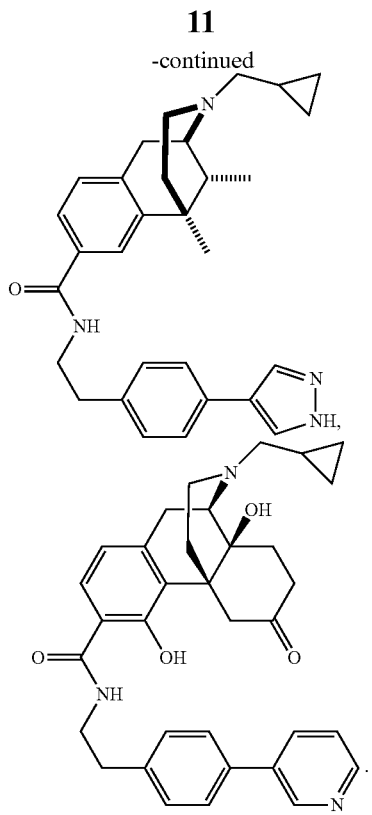

or

Furthermore, provided herein is a method of treating a depressive symptom in a subject comprising administering to the subject a compound of Formula IV:

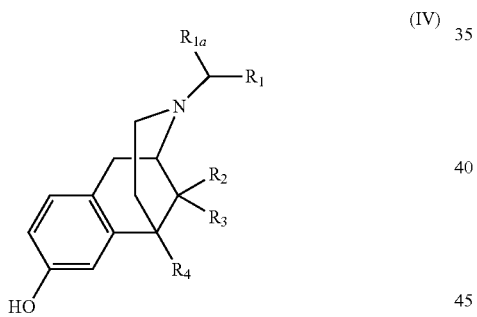 (IV)

or a pharmaceutically acceptable salt thereof, wherein:
R₁ is $C_1$-$C_6$ alkyl, $C_2$-$C_6$ alkenyl, aryl, cycloalkyl, heterocyclyl, benzyl, hydroxyalkyl, or alkoxyalkyl;
R$_{1a}$ is H or methyl;
R₂ is H, hydroxyl, or methoxy; and
R₃ and R₄ are each methyl, or alternatively, R₃ and R₄, together with the carbon atoms to which they are attached, form a 6-membered unsubstituted carbocyclic ring.

In certain embodiment, the compound of Formula IV is:

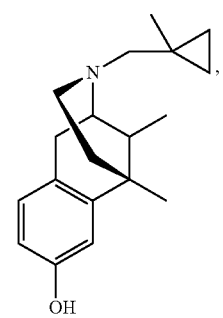

-continued

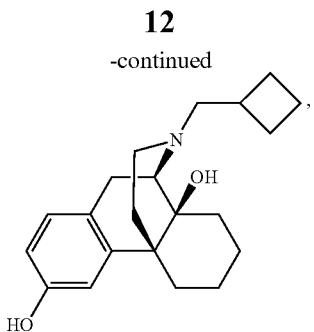

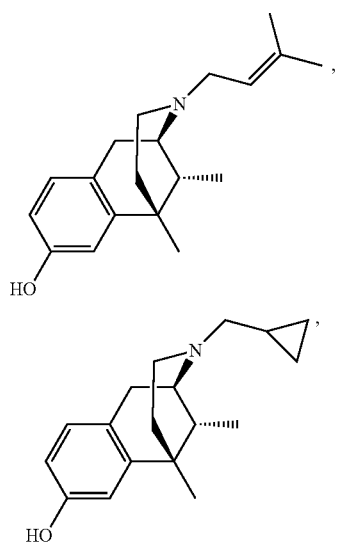

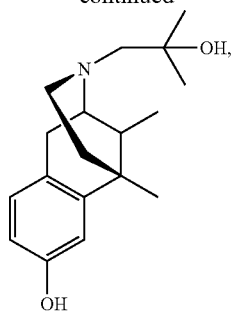
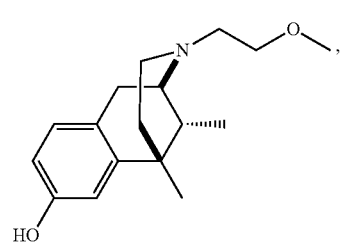
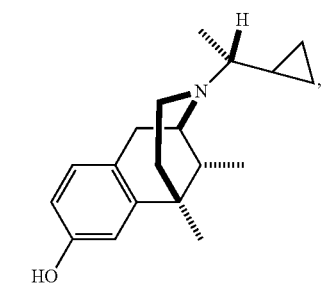
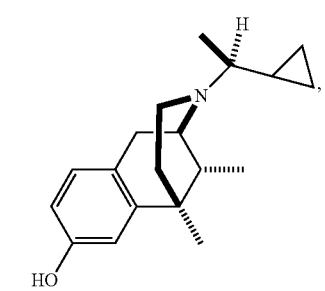
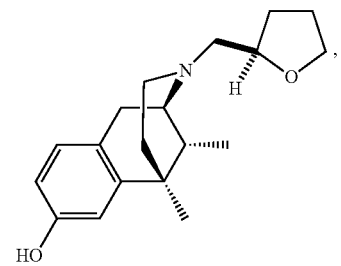
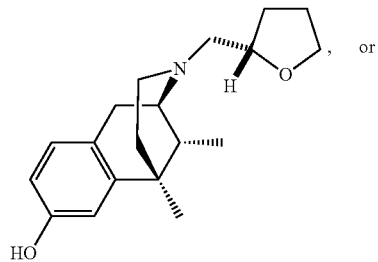, or
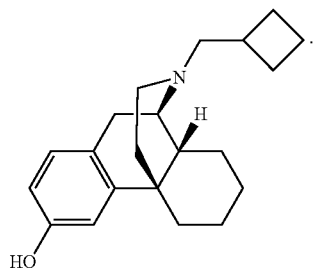
In yet another aspect, provided herein is a method of treating a depressive symptom in a subject comprising administering to the subject a compound selected from:
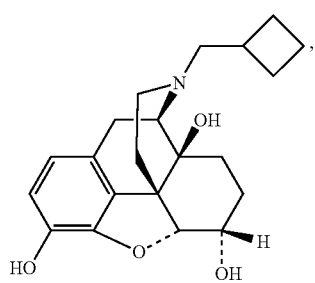
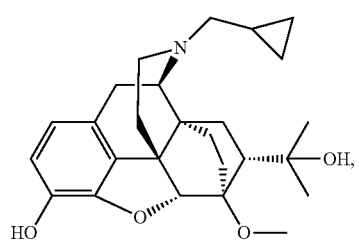
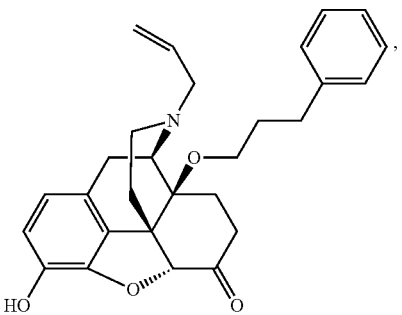
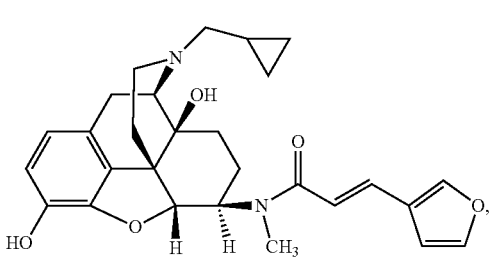

-continued

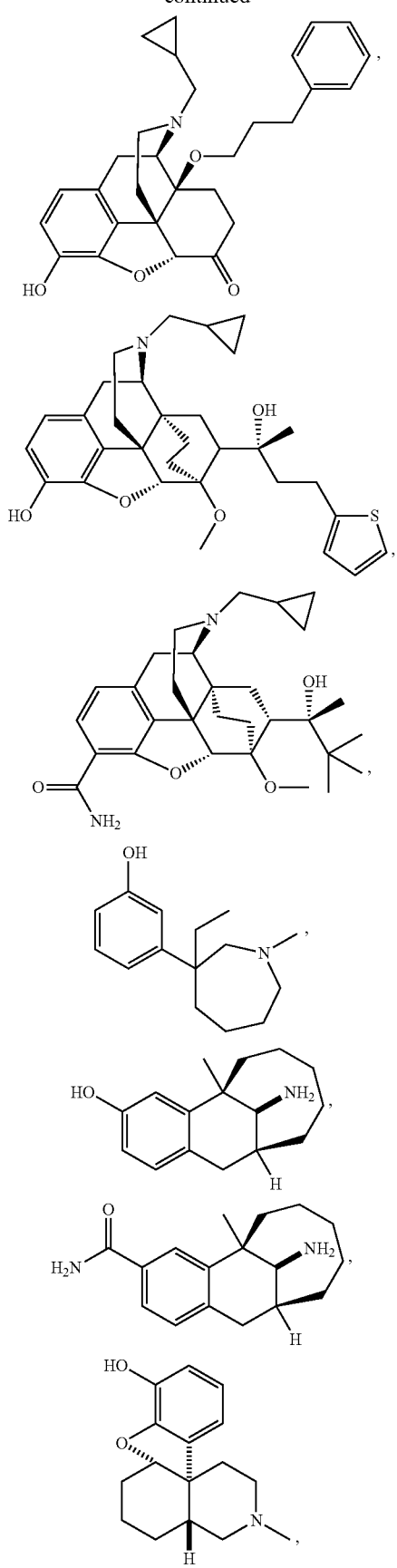

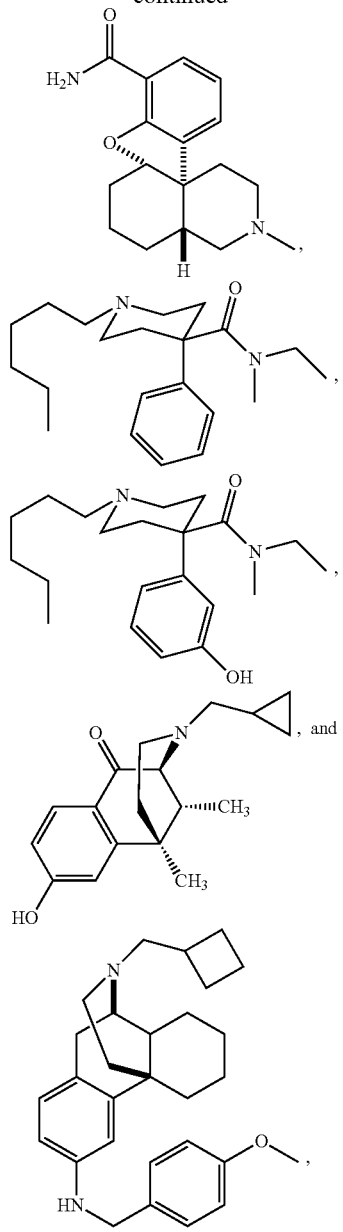

or a pharmaceutically acceptable salt thereof.

In certain embodiments of the methods disclosed herein, the compound is a µ opioid receptor agonist that exhibits an Emax of 5% to 45% in a GTPγS binding assay. In particular embodiments, the Emax is 15% to 35% in a GTPγS binding assay. In other embodiments, said agonist has a low risk of opioid dependence, opioid addiction, and/or symptoms of opioid withdrawal.

In other embodiments of the methods, the compound exhibits a maximal dopamine efflux in the nucleus accumbens of 125% to 300% over base line in a rat. In particular embodiments, the compound has a maximal dopamine efflux in the nucleus accumbens of 200% to 300% over base line in a rat.

In still other embodiments, the compound of the methods provided herein does not attenuate thermal pain in a rodent hot plate model when administered at a dose of at least 1 mg/kg. In particular embodiments, the compound does not attenuate thermal pain in a rodent hot plate model when administered at a dose of at least 3 mg/kg. In other embodiments, the compound does not attenuate thermal pain in a rodent hot plate model when administered at a dose of 10 mg/kg.

In preferred embodiments of the methods provided herein, the subject is a human.

In certain embodiments of the methods provided herein, the depressive symptom is depressed mood, loss of pleasure, loss of appetite, sleep disturbance, psychomotor changes, fatigue, and/or post-partum depression.

In other embodiments, the depressive symptom is associated with a mental condition, wherein the mental condition is schizoaffective disorder, and/or seasonal affective disorder.

In still other embodiments, the depressive symptom is acute stress disorder, adjustment disorders with depressed mood, Asperger syndrome, attention deficit, bereavement, bipolar I disorder, bipolar II disorder, borderline and personality disorder, cyclothymia and dysthymia, depression such as major depressive disorder (MDD) and treatment-resistant disorder (TRD), Dysthymic disorder, hyperactivity disorder, impulse control disorder, mixed mania, obsessive-compulsive personality disorder (OCD), paranoid, post-traumatic stress disorder, seasonal affective disorder, self-injury separation, sleep disorder, substance-induced mood disorder, Tourette syndrome and tic disorder, and/or Trichotillomania.

In other embodiments, the depressive symptom is an anxiety disorder, wherein the anxiety disorder is generalized anxiety disorder, panic, agoraphobia, acute stress, and/or post-traumatic stress disorder.

In still other embodiments of the treatment methods, the depressive symptom is associated with chronic or recurrent depression.

BRIEF DESCRIPTION OF THE DRAWINGS

FIG. 3 depicts the results of in vivo microdialysis experiments measuring dopamine release in the rat nucleus accumbens induced by Compound A and buprenorphine.

DETAILED DESCRIPTION

Methods of Treatment

Figure 1:
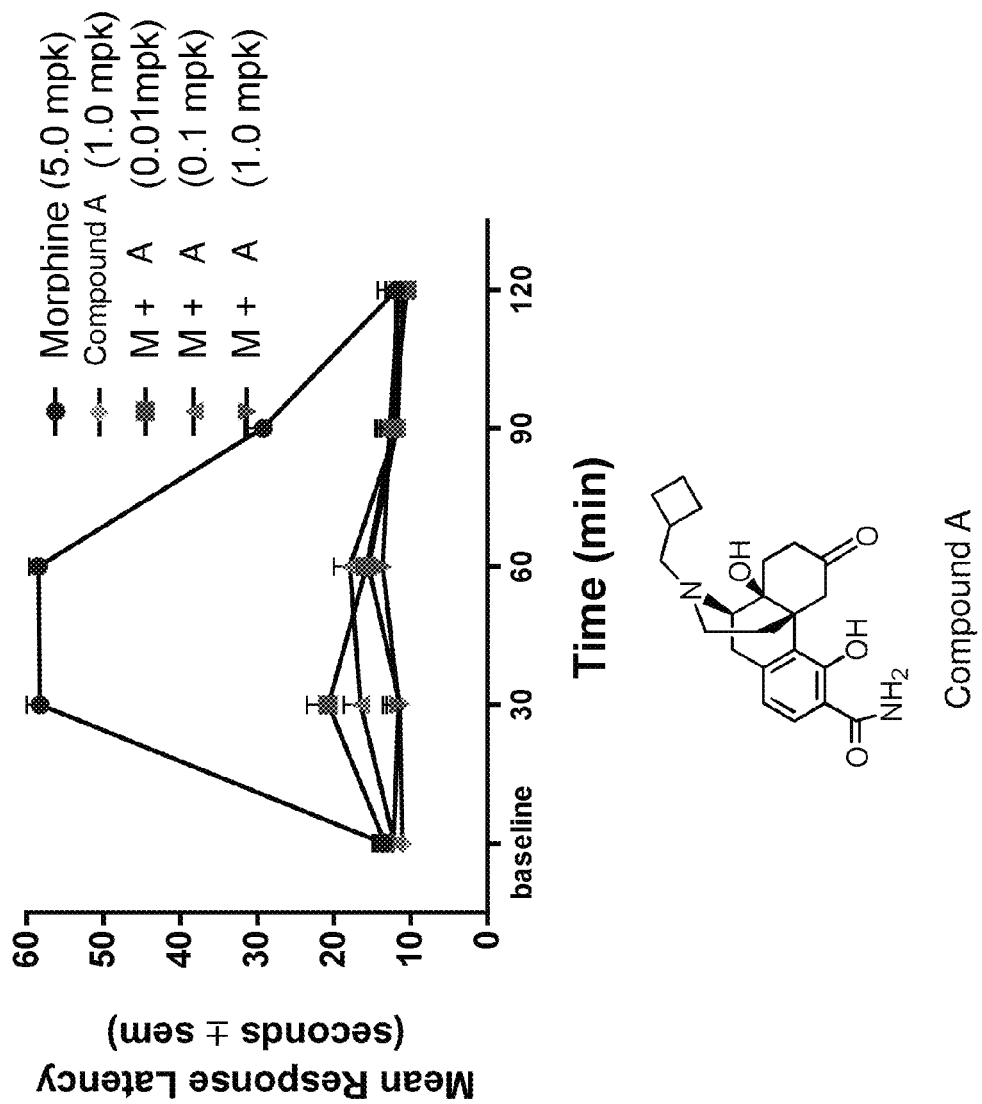
FIG. 1 depicts the results of experiments measuring the antinociceptive effects of Compound A, either alone or in combination with morphine, using a rat hot plate assay.

The compounds of Formulas (I), (II), (III), (IV), and Table A, provided herein, are particularly suitable for treating a depressive symptom. The depressive symptom can be depressed mood, loss of pleasure, loss of appetite, sleep disturbance, psychomotor changes, fatigue, and/or post-partum depression. The depressive symptom can be associated with a mental condition, wherein the mental condition is schizoaffective disorder, and/or seasonal affective disorder.

Furthermore, the depressive symptom can be acute stress disorder, adjustment disorders with depressed mood, Asperger syndrome, attention deficit, bereavement, bipolar I disorder, bipolar II disorder, borderline and personality disorder, cyclothymia and dysthymia, depression such as major depressive disorder (MDD) and treatment-resistant disorder (TRD), Dysthymic disorder, hyperactivity disorder, impulse control disorder, mixed mania, obsessive-compulsive personality disorder (OCD), paranoid, post-traumatic stress disorder, seasonal affective disorder, self-injury separation, sleep disorder, substance-induced mood disorder, Tourette syndrome and tic disorder, and/or Trichotillomania.

The depressive symptom can also be an anxiety disorder, wherein the anxiety disorder is generalized anxiety disorder, panic, agoraphobia, acute stress, and/or post-traumatic stress disorder.

The depressive symptom can be associated with chronic or recurrent depression.

Accordingly, provided herein are methods of treating depressive symptoms in a subject in need thereof, comprising administering to the subject a compound, or a pharmaceutically acceptable salt thereof, of Formulas (I), (II), (III), or (IV), or Table A.

It has been discovered that Emax value in a GTPγS binding assay can be used to select a μ opioid receptor agonists for the treatment of a depressive symptom. In particular, it has been discovered that compounds with an Emax of 5% to 45% in a GTPγS binding assay are especially suitable for treating depressive symptoms. Thus, in one aspect, provided herein is a method of treating a depressive symptom in a subject in need thereof comprising administering to the subject an effective amount of a μ opioid receptor agonist that exhibits an Emax of 5% to 45% (e.g., 5, 10, 15, 20, 25, 30, 35, 40, or 45%) in a GTPγS binding assay. In a particular embodiment, the Emax of the agonist is 15% to 35% in a GTPγS binding assay. In another embodiment, the agonist has a low risk of opioid dependence, opioid addiction and/or symptoms of opioid withdrawal. Non-limiting examples of such agonist include the compounds of Formulas I, II, III and IV, as well as the compounds of Table A.

It has also been discovered that a compound that exhibits a maximal dopamine efflux in the nucleus accumbens in a rat of 125% to 300% over base line is particularly suitable for treatment of depressive symptoms. Thus, in another aspect, provided herein is a method of treating a depressive symptom in a subject in need thereof comprising administering to the subject an effective amount of a compound that exhibits a maximal dopamine efflux in the nucleus accumbens in a rat of 125% to 300% (e.g., 125, 150, 175, 200, 225, 250, 275, or 300%) over base line. In a particular embodiment, the maximal dopamine efflux in the nucleus accumbens in a rat is 200% to 300% over base line. In another embodiment, the compound has a low risk of opioid dependence, opioid addiction and/or symptoms of opioid withdrawal. Non-limiting examples of such compound include the compounds of Formulas I, II, III and IV, as well as the compounds of Table A.

In still another aspect, provided herein is a method of treating a depressive symptom in a subject in need thereof comprising administering to the subject an effective amount of a compound that does not attenuate thermal pain in a rodent hot plate model when administered at a dose of at least 1 mg/kg (e.g., 1, 2, 3, 4, 5, 6, 7, 8, 9, or 10 mg/kg). In one embodiment, the compound does not attenuate thermal pain in a rodent hot plate model when administered at a dose of 1-10 mg/kg (e.g., 1, 2, 3, 4, 5, 6, 7, 8, 9, or 10 mg/kg). In one embodiment, the compound does not attenuate thermal pain in a rodent hot plate model when administered at a dose of at least 3 mg/kg. In another embodiment, the compound does not attenuate thermal pain in a rodent hot plate model when administered at a dose of 10 mg/kg. In still another embodiment, the compound has a low risk of opioid dependence, opioid addiction and or symptoms of opioid withdrawal. Non-limiting examples of such compound include the compounds of Formulas I, II, III and IV, as well as the compounds of Table A.

In one aspect, provided herein is a method of treating a depressive symptom in a subject in need thereof comprising administering to the subject a compound of Formula I:

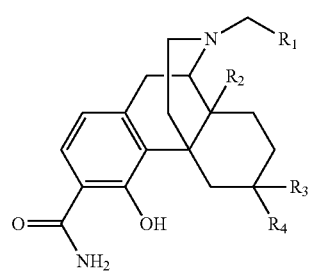

(I)

or a pharmaceutically acceptable salt thereof, wherein:
$R_1$ is cyclobutyl,

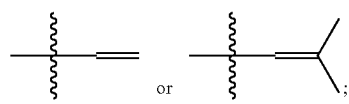

$R_2$ is H, hydroxyl, or methoxy; and $R_3$ and $R_4$ are each, independently, H hydroxyl, or $NR_5R_6$, wherein $R_5$ and $R_6$ are each independently H, alkyl or optionally substituted acyl, or alternatively, $R_3$ and $R_4$, together with the carbon atom to which they are attached, form C=O or C=CH$_2$.

In one embodiment, the substituted acyl is defined as follows:

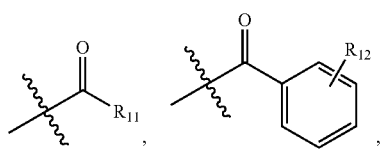

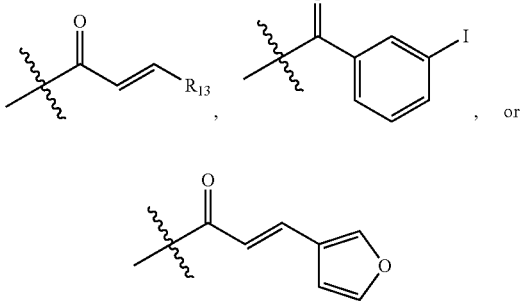

wherein $R_{11}$ is linear or branched $C_1$-$C_6$ alkyl; $R_{12}$ is halo, $C_1$-$C_6$ alkyl, or $C_1$-$C_6$ alkoxy; and $R_{13}$ is aryl or heteroaryl. In one embodiment of Formula (IV), $R_1$ is cyclopropyl.

In another embodiment, the compound of Formula I is

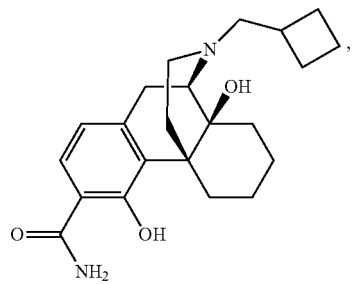

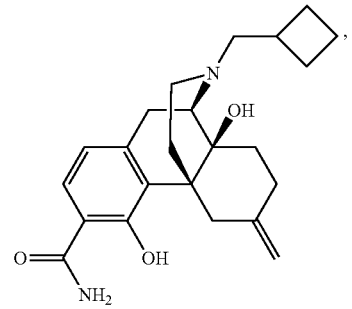

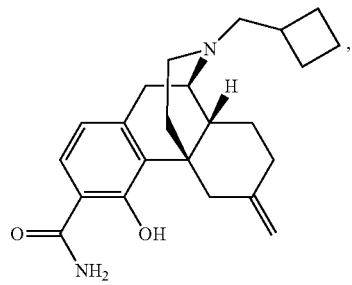

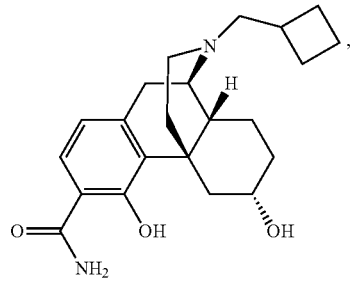

21
-continued
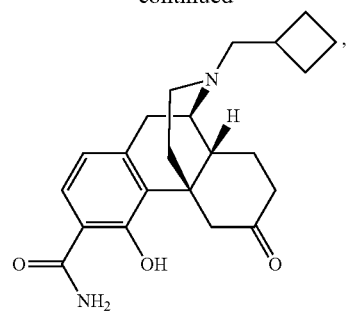
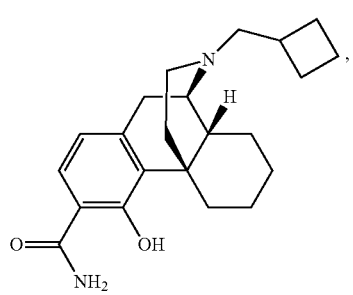
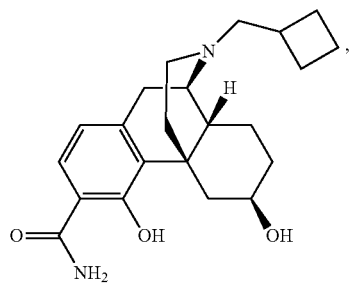
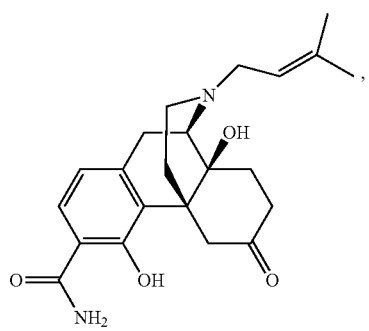
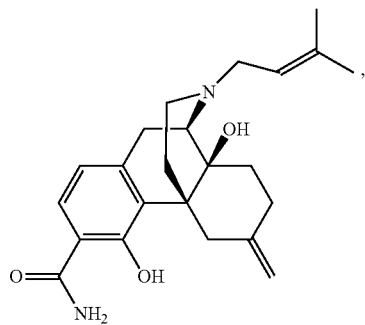
22
-continued
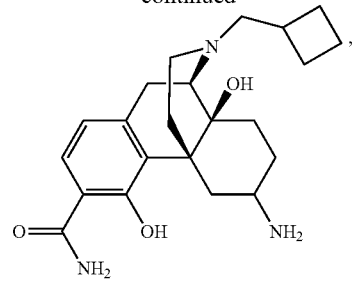
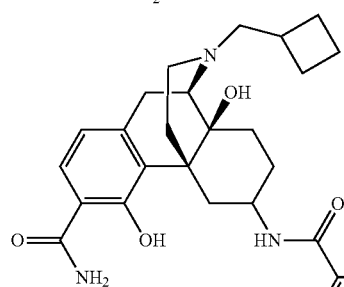
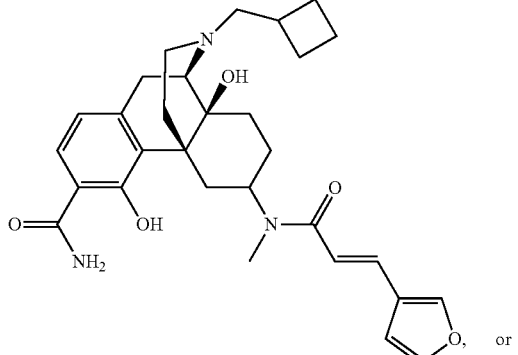
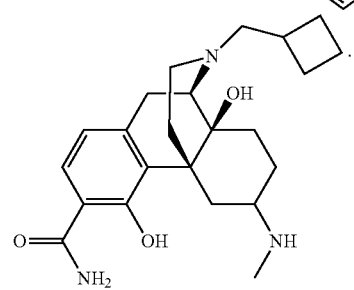
In another aspect, provided herein is a method of treating a depressive symptom in a subject in need thereof comprising administering to the subject a compound of Formula II:
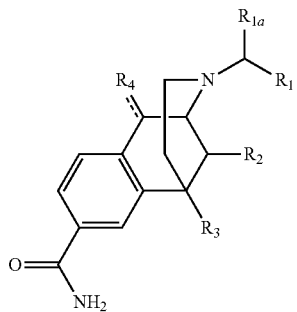
(II)

or a pharmaceutically acceptable salt thereof, wherein:

$R_1$ is $C_1$-$C_6$ alkyl, $C_2$-$C_6$ alkenyl, cycloalkyl, heterocyclyl, hydroxyalkyl, or alkoxyalkyl;

$R_{1a}$ is H or methyl;

$R_2$ and $R_3$ are each methyl, or alternatively, $R_2$ and $R_3$, together with the carbon atoms to which they are attached, form a 6-membered unsubstituted carbocyclic ring;

when ----- is a single bond, $R_4$ is H; and when ----- is a double bond, $R_4$ is O.

In one embodiment, the compound of Formula II is:

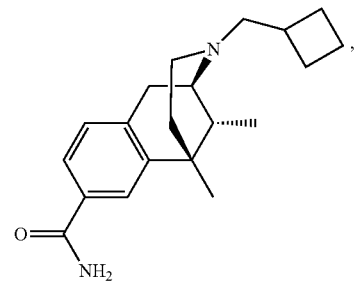,

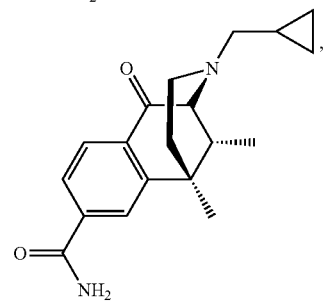,

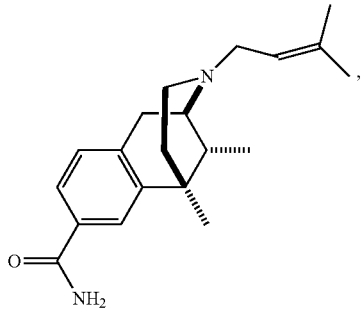,

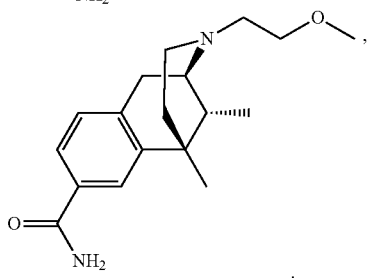,

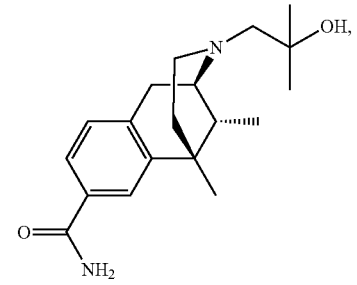,

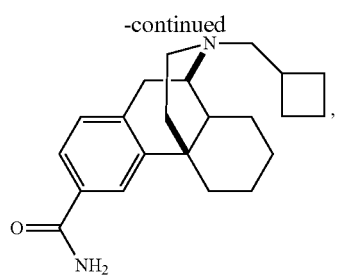,

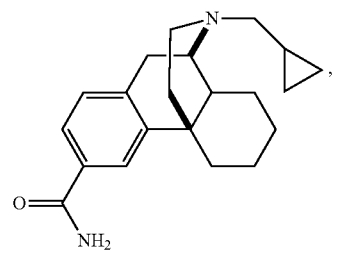,

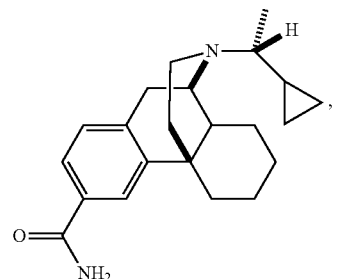,

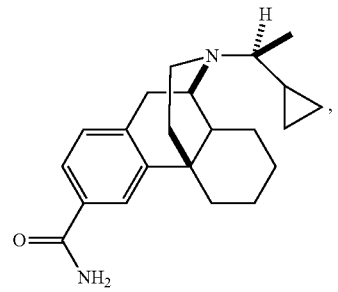,

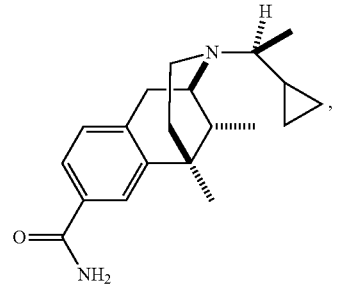,

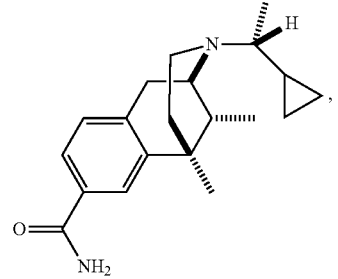,

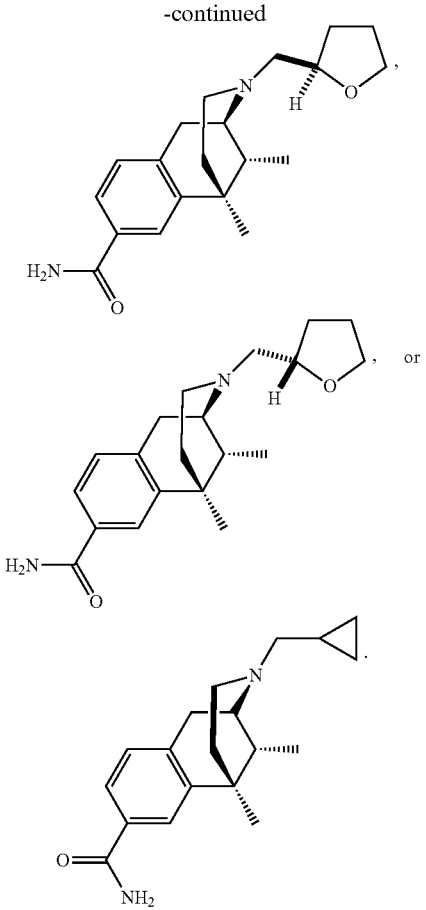

In still another aspect, provided herein is a method of treating a depressive symptom in a subject in need thereof comprising administering to the subject a compound of Formula III:

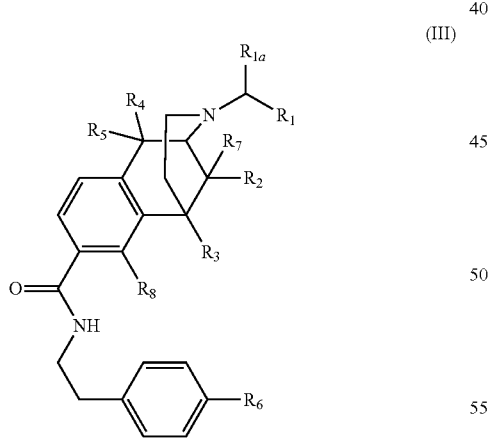
(III)

or a pharmaceutically acceptable salt thereof, wherein:

$R_1$ is $C_1$-$C_6$ alkyl, $C_2$-$C_6$ alkenyl, aryl, cycloalkyl, heterocyclyl, benzyl, hydroxyalkyl, or alkoxyalkyl;

$R_{1a}$ is H or methyl;

$R_2$ and $R_3$ are each H, methyl, or ethyl, or alternatively, $R_2$ and $R_3$, together with the carbon atoms to which they are attached, form a 6-membered unsubstituted carbocyclic ring or carbonyl-substituted carbocyclic ring;

$R_4$ and $R_5$ are each, independently, H, hydroxyl, or $C_1$-$C_6$ alkyl;

$R_6$ is unsubstituted or substituted $C_6$-$C_{10}$ aryl, or substituted or unsubstituted heteroaryl comprising one or two 5- or 6-membered rings and 1-4 heteroatoms selected from N, O and S; and $R_7$ and $R_8$ are each, independently, H or hydroxyl.

In one embodiment, the compound of Formula III is:

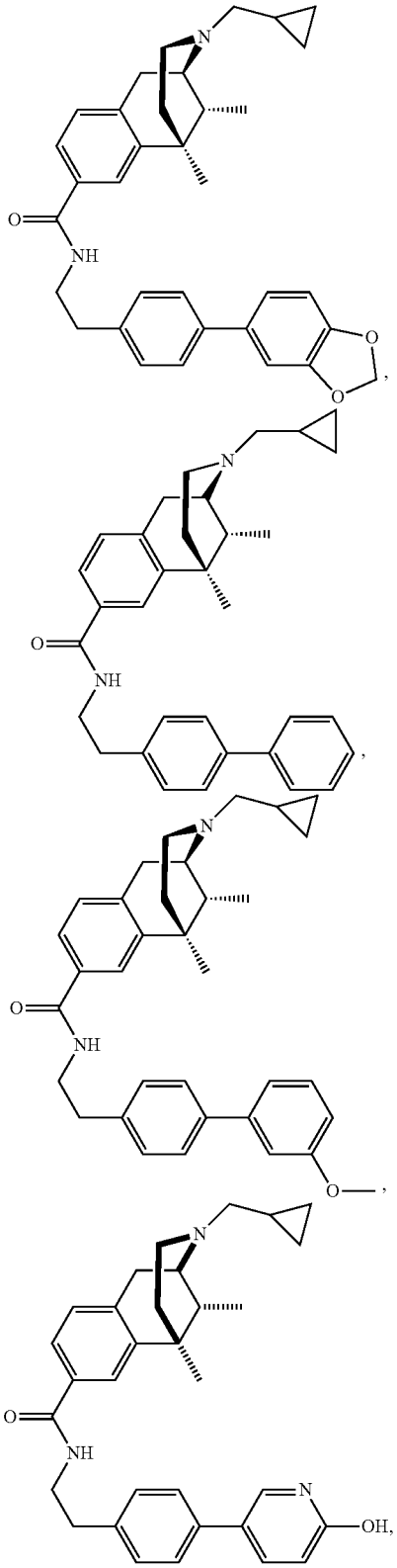

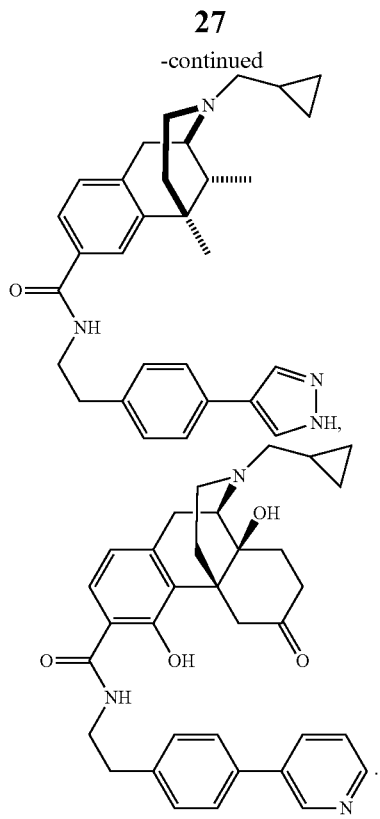

or

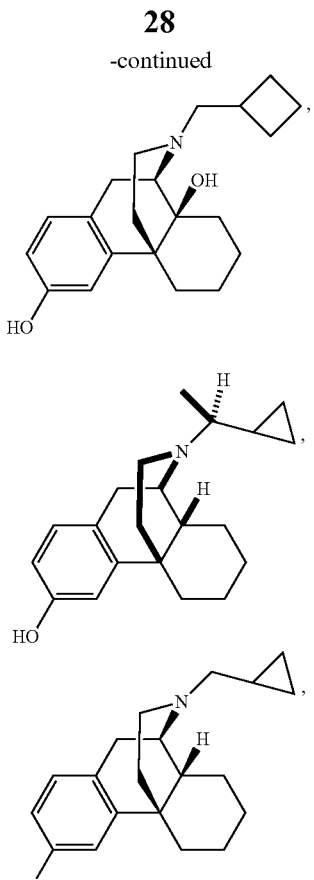

In another aspect, provided herein is a method of treating a depressive symptom in a subject in need thereof comprising administering to the subject a compound of Formula IV:

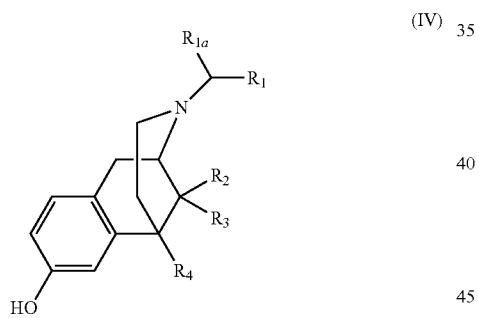

(IV)

or a pharmaceutically acceptable salt thereof, wherein:
$R_1$ is $C_1$-$C_6$ alkyl, $C_2$-$C_6$ alkenyl, aryl, cycloalkyl, heterocyclyl, benzyl, hydroxyalkyl, or alkoxyalkyl;
$R_{1a}$ is H or methyl;
$R_2$ is H, hydroxyl, or methoxy; and
$R_3$ and $R_4$ are each methyl, or alternatively, $R_3$ and $R_4$, together with the carbon atoms to which they are attached, form a 6-membered unsubstituted carbocyclic ring.

In one embodiment, the compound of Formula IV is:

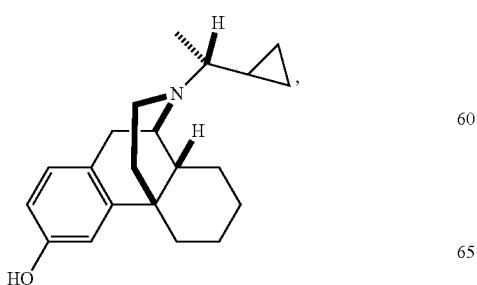

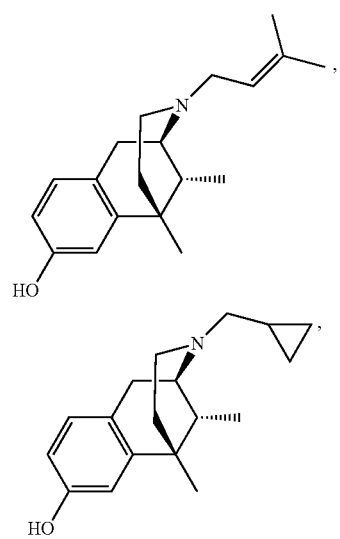

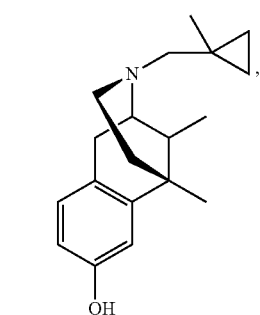

-continued
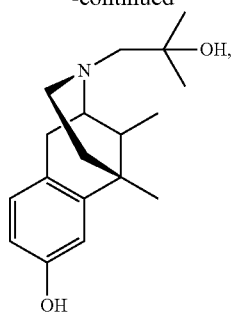
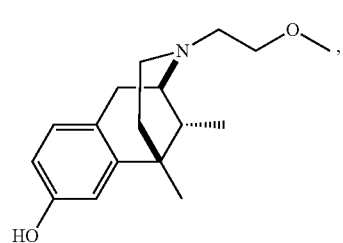
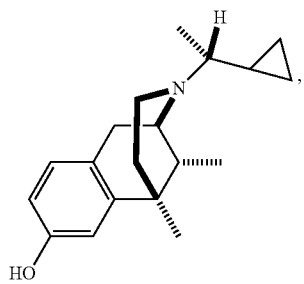
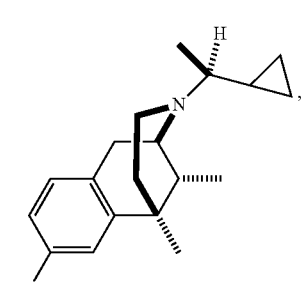
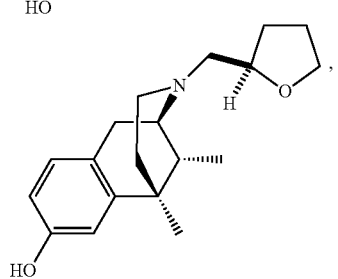
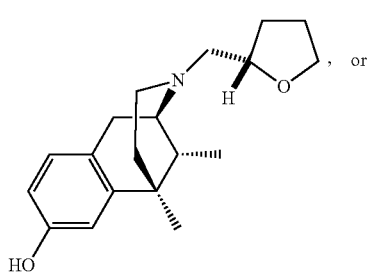, or
-continued
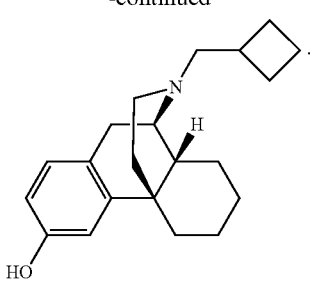
In yet another aspect, provided herein is a method of treating a depressive symptom in a subject in need thereof comprising administering to the subject a compound selected from Table A, or a pharmaceutically acceptable salt thereof.
TABLE A
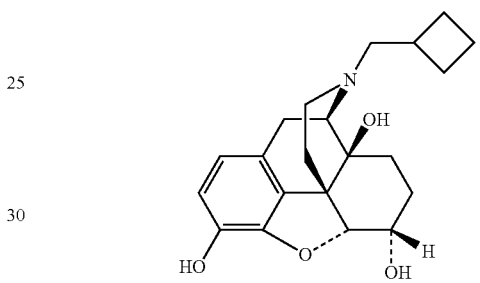
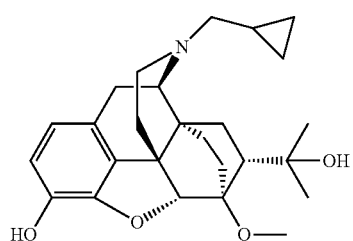 [SMILES: CO[C@]12CC[C@@]3(C[C@@H]1C(C)(C)O)[C@H]1Cc4ccc(O)c5c4[C@@]3(CCN1CC1CC1)[C@H]2O5]
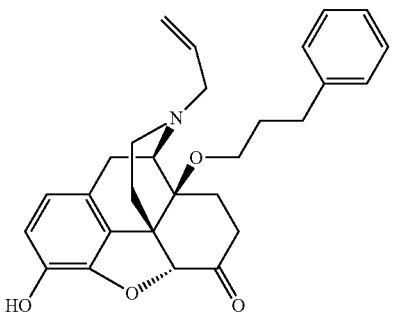 [SMILES: C=CCN1CC[C@]23c4c5ccc(O)c4O[C@H]2C(=O)CC[C@@]3(OCCCc2ccccc2)[C@H]1C5]
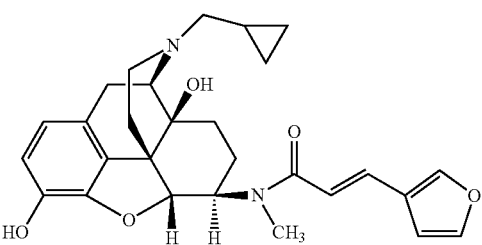 [SMILES: CN(C(=O)/C=C/c1ccoc1)[C@@H]1CC[C@@]2(O)[C@H]3Cc4ccc(O)c5c4[C@@]2(CCN3CC2CC2)[C@H]1O5]

TABLE A-continued
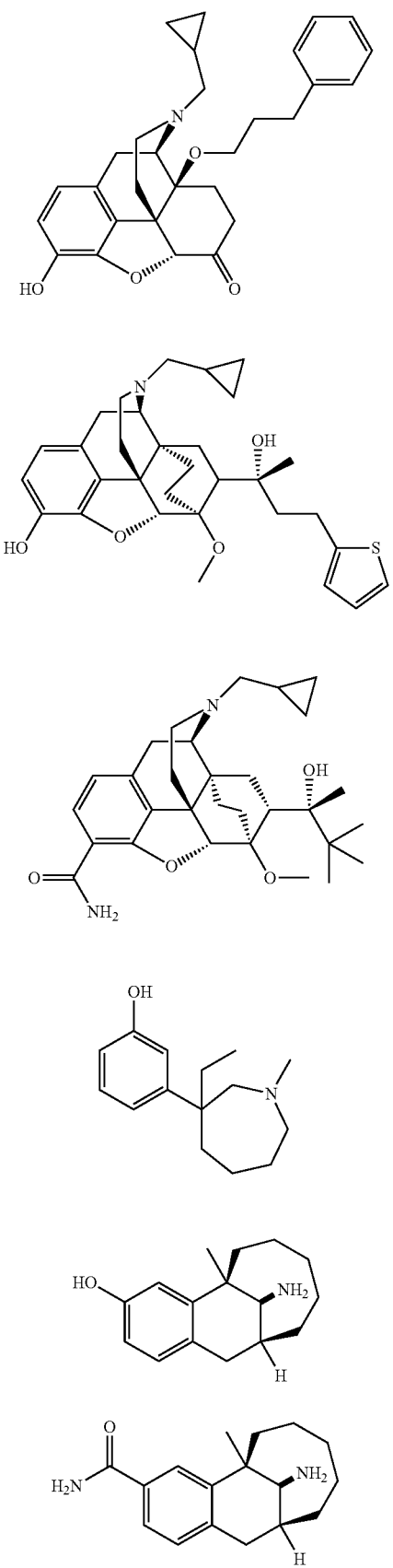
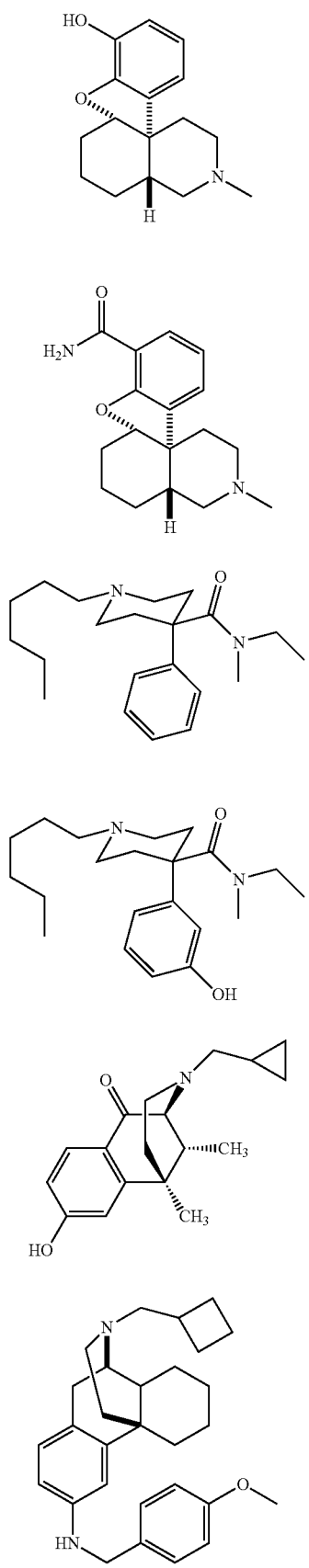

TABLE A-continued

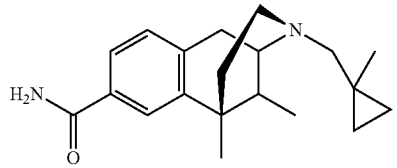

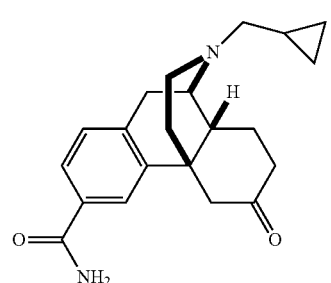

Compound B

In another aspect, provided herein is a method of treating depression in a subject in need thereof, comprising administering to the subject the compound of Formulas (I), (II), (III), or (IV), or Table A, or a pharmaceutically acceptable salt thereof.

In one embodiment, provided herein is a method of treating depression in a subject in need thereof, comprising administering to the subject the compound of Formula (I) or a pharmaceutically acceptable salt thereof.

In another embodiment, provided herein is a method of treating depression in a subject in need thereof, comprising administering to the subject the compound of Formula (II) or a pharmaceutically acceptable salt thereof.

In still another embodiment, provided herein is a method of treating depression in a subject in need thereof, comprising administering to the subject the compound of Formula (III) or a pharmaceutically acceptable salt thereof.

In yet another embodiment, provided herein is a method of treating depression in a subject in need thereof, comprising administering to the subject the compound of Formula (IV) or a pharmaceutically acceptable salt thereof.

In yet another embodiment, provided herein is a method of treating depression in a subject in need thereof, comprising administering to the subject the compound of Table A or a pharmaceutically acceptable salt thereof.

In yet another aspect, provided herein is a method of treating a depressive symptom in a subject in need thereof comprising administering to the subject a compound selected from Table B, or a pharmaceutically acceptable salt thereof.

In yet another embodiment, provided herein is a method of treating depression in a subject in need thereof, comprising administering to the subject the compound of Table B or a pharmaceutically acceptable salt thereof.

In one specific embodiment, provided herein is a method of treating depression and/or a depressive symptom in a subject in need thereof, comprising administering to the subject the compound:

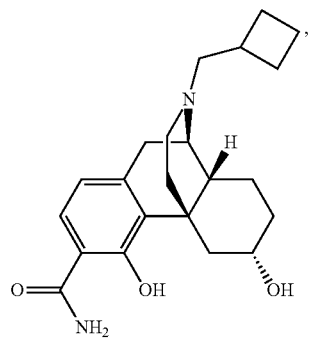 [SMILES: NC(=O)c1ccc2c(c1O)[C@]13CCN(CC4CCC4)[C@H](C2)[C@@H]1CC[C@H](O)C3]

or a pharmaceutically acceptable salt thereof.

In another embodiment, provided herein is a method of treating depression and/or a depressive symptom in a subject in need thereof, comprising administering to the subject the compound:

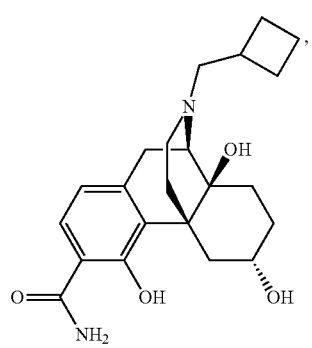 [SMILES: NC(=O)c1ccc2c(c1O)[C@]13CCN(CC4CCC4)[C@H](C2)[C@]1(O)CC[C@H](O)C3]

or a pharmaceutically acceptable salt thereof.

In still another embodiment, provided herein is a method of treating depression and/or a depressive symptom in a subject in need thereof, comprising administering to the subject the compound:

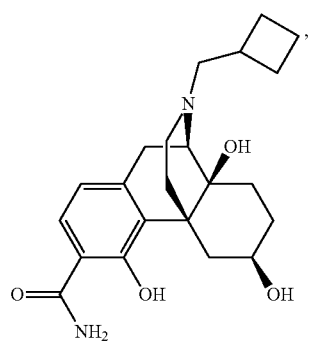 [SMILES: NC(=O)c1ccc2c(c1O)[C@]13CCN(CC4CCC4)[C@H](C2)[C@]1(O)CC[C@@H](O)C3]

or a pharmaceutically acceptable salt thereof.

In still another embodiment, provided herein is a method of treating depression and/or a depressive symptom in a subject in need thereof, comprising administering to the subject the compound:

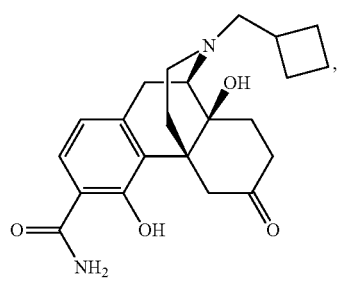 [SMILES: NC(=O)c1ccc2c(c1O)[C@]13CCN(CC4CCC4)[C@H](C2)[C@]1(O)CCC(=O)C3]

or a pharmaceutically acceptable salt thereof.

In one embodiment, the compound of Formulas (I), (II), (III), or (IV), or Table is a μ opioid receptor agonist having an Emax of 5% to 45% (e.g., 5, 10, 15, 20, 25, 30, 35, 40, or 45%) in a GTPγS binding assay. In one particular embodiment, the agonist exhibits an Emax of 15% to 35% in the GTPγS binding assay. In another embodiment, said agonist has a low risk of opioid dependence, opioid addiction and or symptoms of opioid withdrawal.

In one embodiment, the compound of Formulas (I), (II), (III), or (IV), or Table A, is a compound that exhibits a maximal dopamine efflux in the nucleus accumbens in a rat of 125% to 300% (e.g., 125, 150, 175, 200, 225, 250, 275, or 300%) over base line. In one particular embodiment, the maximal dopamine efflux in the nucleus accumbens of a rat is 200% to 300% over base line. In another embodiment, the compound has a low risk of opioid dependence, opioid addiction and or symptoms of opioid withdrawal.

In another embodiment, the compound of Formulas (I), (II), (III), or (IV), or Table A, is a compound that does not attenuate thermal pain in a rodent hot plate model when administered at of dose of at least 1 mg/kg (e.g., 1, 2, 3, 4, 5, 6, 7, 8, 9, or 10 mg/kg). In one embodiment, the compound does not attenuate thermal pain in a rodent hot plate model when administered at a dose of 1-10 mg/kg (e.g., 1, 2, 3, 4, 5, 6, 7, 8, 9, or 10 mg/kg). In one particular embodiment, the compound does not attenuate thermal pain in a rodent hot plate model when administered at a dose of at least 3 mg/kg. In another embodiment, the compound does not attenuate thermal pain in a rodent hot plate model when administered at a dose of 10 mg/kg. In another embodiment, the compound has a low risk of opioid dependence, opioid addiction and or symptoms of opioid withdrawal.

In one particular embodiment of the above-described methods, the subject is a human.

In another embodiment, the depressive symptom is depressed mood, loss of pleasure, loss of appetite, sleep disturbance, psychomotor changes, fatigue, and/or post-partum depression.

In still another embodiment, the depressive symptom can be associated with a mental condition, wherein the mental condition is schizoaffective disorder, and/or seasonal affective disorder.

In yet another embodiment, the depressive symptom is acute stress disorder, adjustment disorders with depressed mood, Asperger syndrome, attention deficit, bereavement, bipolar I disorder, bipolar II disorder, borderline and personality disorder, cyclothymia and dysthymia, depression such as major depressive disorder (MDD) and treatment-resistant disorder (TRD), Dysthymic disorder, hyperactivity disorder, impulse control disorder, mixed mania, obsessive-compulsive personality disorder (OCD), paranoid, post-traumatic stress disorder, seasonal affective disorder, self-injury separation, sleep disorder, substance-induced mood disorder, Tourette syndrome and tic disorder, and/or Trichotillomania.

In another embodiment, the depressive symptom is an anxiety disorder, wherein the anxiety disorder is generalized anxiety disorder, panic, agoraphobia, acute stress, and/or post-traumatic stress disorder.

In another embodiment, the depressive symptom is associated with chronic or recurrent depression.

Definitions

The term "treat," "treated," "treating" or "treatment" includes the diminishment or alleviation of at least one symptom associated or caused by the state, disorder or disease being treated. In certain embodiments, the treatment comprises bringing into contact with the opioid receptor an effective amount of a μ opioid receptor agonist, such as a compound of Formulas (I), (II), (III), or (IV), or Table A.

The term "subject" is intended to be a mammal. Examples of subjects include humans, dogs, cows, horses, pigs, sheep, goats, cats, mice, rabbits, rats, and transgenic non-human animals. In preferred embodiments, the subject is a human, e.g., a human suffering from a depressive symptom, pain, pruritis, diarrhea, irritable bowel syndrome, gastrointestinal motility disorder, obesity, respiratory depression, convulsions, coughing, hyperalgesia, or drug addiction.

As used to herein, the term "GTPγS binding assay" refers to the GTPγS binding assay described in Example B1, herein. This GTPγS binding assay is performed under conditions such that the observed Emax value for buprenorphine (CAS#52485-79-7) in this assay is at least 50% compared to baseline.

As used to herein, the term "Emax" refers to the maximal observed effect of a compound. In certain embodiments, the Emax is the maximal percentage increase of [35S]GTPγS binding induced by an agonist relative to basal [35S]GTPγS binding in the absence of any drug.

As used to herein, the term "EC50" refers to the concentration of a compound required to achieve an effect that is 50% of the Emax.

As used to herein, the term "rodent hot plate model" refers to the thermal pain assay described in Example B2, herein.

As used herein the term "low risk of opioid dependence, opioid addiction and or symptoms of opioid withdrawal" refers to low "abuse liability." Drugs with "abuse liability" are those associated with physical and/or psychological dependence in humans, or with a probability for diversion from the intended medical condition for recreational use. There are a variety of animal models that can be used to assess the abuse liability of drugs. In general, these models use comparator drugs with known high abuse potential. For the opioid class of compounds, the most common comparator drug is morphine. Morphine has been shown clinically to have a high potential for abuse. Morphine produces a "drug high," dependency when the drug is repeatedly administered, and withdrawal when the drug use is abruptly stopped. Each of these traits can be evaluated in animal models for a given experimental drug to determine its relative risk compared to morphine. For example, efflux of nucleus accumbens dopamine can be evaluated as a predictor of the high or euphoria following administration of the drug. A reduction in the maximal possible observed increase in dopamine efflux would be correlated with a significantly lower degree of euphoria and a reduction in the abuse liability associated with drug-liking. Similarly, the potential for dependence and withdrawal can be determined in standard animal models in which the drug is administer 1-3 times per day, or by continual infusion for 5 to 14 days, followed by abrupt withdrawal. For addictive opioids, abrupt cessation of administration of the drug will cause withdrawal characterized by such traits as weight-loss associated with excessive urination and defecation, increased shaking behavior, increased "jumping" activity, and reduced body temperature. These are quantitative measures that can be used to evaluate the relative risk for dependency compared to morphine. The ability of a drug to induce withdrawal in opioid-dependent patients will also lead to a reduced abuse liability associated with diversion of the drug. This feature can also be directly assessed in animals by making them dependent on morphine, or another opioid agonist, and then precipitating withdrawal by the administration of the drug. In certain embodiments, the compounds disclosed herein have a lower abuse liability (e.g., a lower risk of opioid dependence, opioid addiction and or symptoms of opioid withdrawal) than buprenorphine.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, 1 to 6 carbons, 1 to 4 carbons, or 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Furthermore, the expression "$C_x$-$C_y$-alkyl", wherein x is 1-5 and y is 2-10 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl and isobutyl.

The term "alkenyl," alone or in combination refers to a straight-chain, cyclic or branched hydrocarbon residue comprising at least one olefinic bond and the indicated number of carbon atoms. Preferred alkenyl groups have up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl, isobutenyl, 1-cyclohexenyl, 1-cyclopentenyl.

As used herein, the term "cycloalkyl" or "carbocyclic" refers to saturated or unsaturated monocyclic, bicyclic or tricyclic hydrocarbon groups of 3-12 carbon atoms, preferably 3-9, or 3-7 carbon atoms. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

"Alkoxyalkyl" refers to a group having the formula —$R^i$—$OR^{ii}$, wherein $R^i$ is an alkyl group as defined above, and $OR^{ii}$ is an alkoxy group as defined below.

"Alkoxy" refers to those alkyl groups, having from 1 to 10 carbon atoms, attached to the remainder of the molecule via an oxygen atom. Alkoxy groups with 1-8 carbon atoms are preferred. The alkyl portion of an alkoxy may be linear, cyclic, or branched, or a combination thereof. Examples of alkoxy groups include methoxy, ethoxy, isopropoxy, butoxy, cyclopentyloxy, and the like. An alkoxy group can also be represented by the following formula: —$OR^i$, where $R^i$ is the "alkyl portion" of an alkoxy group.

The term "hydroxyalkyl" refers to a group having the formula —$R^{iii}$—OH, wherein $R^{iii}$ is an alkyl group as defined above.

The term "aryl" includes aromatic monocyclic or multi-cyclic e.g., tricyclic, bicyclic, hydrocarbon ring systems consisting only of hydrogen and carbon and containing from six to nineteen carbon atoms, or six to ten carbon atoms, where the ring systems may be partially saturated. Aryl groups include, but are not limited to, groups such as phenyl, tolyl, xylyl, anthryl, naphthyl and phenanthryl. Aryl groups can also be fused or bridged with alicyclic or heterocyclic rings which are not aromatic so as to form a polycycle (e.g., tetralin).

The term "heteroaryl," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" refers to a five-member to ten-member, fully saturated or partially unsaturated nonaromatic heterocylic groups containing at least one heteroatom such as O, S or N. The most frequent examples are piperidinyl, morpholinyl, piperazinyl, pyrrolidinyl or pirazinyl. Attachment of a heterocyclyl substituent can occur via a carbon atom or via a heteroatom.

Moreover, the alkyl, alkenyl, cycloalkyl, cycloalkenyl, alkoxy, aryl, heteroaryl, and heterocycle groups described above can be "unsubstituted" or "substituted." The term "substituted" is intended to describe moieties having substituents replacing a hydrogen on one or more atoms, e.g. C, O or N, of a molecule. Such substituents can independently include, for example, one or more of the following: straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, (CR'R")$_{0-3}$NR'R" (e.g., —$NH_2$), (CR'R")$_{0-3}$CN (e.g., —CN), —$NO_2$, halogen (e.g., —F, —Cl, —Br, or —I), (CR'R")$_{0-3}$C(halogen)$_3$ (e.g., —$CF_3$), (CR'R")$_{0-3}$CH(halogen)$_2$, (CR'R")$_{0-3}$CH$_2$(halogen), (CR'R")$_{0-3}$CONR'R", (CR'R")$_{0-3}$(CNH)NR'R", (CR'R")$_{0-3}$S(O)$_{1-2}$NR'R", (CR'R")$_{0-3}$CHO, (CR'R")$_{0-3}$O(CR'R")$_{0-3}$H, (CR'R")$_{0-3}$S(O)$_{0-3}$R' (e.g., —$SO_3$H, —$OSO_3$H), (CR'R")$_{0-3}$O(CR'R")$_{0-3}$H (e.g., —$CH_2OCH_3$ and —$OCH_3$), (CR'R")$_{0-3}$S(CR'R")$_{0-3}$H (e.g., —SH and —$SCH_3$), (CR'R")$_{0-3}$OH (e.g., —OH), (CR'R")$_{0-3}$COR', (CR'R")$_{0-3}$(substituted or unsubstituted phenyl), (CR'R")$_{0-3}$($C_3$-$C_8$ cycloalkyl), (CR'R")$_{0-3}$CO$_2$R' (e.g., —$CO_2$H), or (CR'R")$_{0-3}$OR' group, or the side chain of any naturally occurring amino acid; wherein R' and R" are each independently hydrogen, a $C_1$-$C_5$ alkyl, $C_2$-$C_5$ alkenyl, $C_2$-$C_5$ alkynyl, or aryl group.

As used herein, the term "acyl" refers to an organic radical linked to a carbonyl.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17.sup.th ed., Mack Publishing Company, Easton, Pa., 1985, p. 1418 and Journal of Pharmaceutical Science, 66, 2 (1977), each of which is incorporated herein by reference in its entirety.

The description of the disclosure herein should be construed in congruity with the laws and principals of chemical bonding. For example, it may be necessary to remove a hydrogen atom in order accommodate a substitutent at any given location. Furthermore, it is to be understood that definitions of the variables (i.e., "R groups"), as well as the bond locations of the generic formulae of the invention (e.g., Formulas I, II, III, or IV), will be consistent with the laws of chemical bonding known in the art. It is also to be understood that all of the compounds of the invention described above will further include bonds between adjacent atoms and/or hydrogens as required to satisfy the valence of each atom. That is, bonds and/or hydrogen atoms are added to provide the following number of total bonds to each of the following types of atoms: carbon: four bonds; nitrogen: three bonds; oxygen: two bonds; and sulfur: two-six bonds.

The compounds of this invention may include asymmetric carbon atoms. It is to be understood accordingly that the isomers arising from such asymmetry (e.g., all enantiomers, stereoisomers, rotamers, tautomers, diastereomers, or racemates) are included within the scope of this invention. Such isomers can be obtained in substantially pure form by classical separation techniques and by stereochemically controlled synthesis. Furthermore, the structures and other compounds and moieties discussed in this application also include all tautomers thereof. Compounds described herein may be obtained through art recognized synthesis strategies.

It will also be noted that the substituents of some of the compounds of this invention include isomeric cyclic structures. It is to be understood accordingly that constitutional isomers of particular substituents are included within the scope of this invention, unless indicated otherwise. For example, the term "tetrazole" includes tetrazole, 2H-tetrazole, 3H-tetrazole, 4H-tetrazole and 5H-tetrazole.

EXEMPLIFICATION OF THE INVENTION

The invention is further illustrated by the following examples, which should not be construed as further limiting. The practice of the present invention will employ, unless otherwise indicated, conventional techniques of cell biology, cell culture, molecular biology, transgenic biology, microbiology and immunology, which are within the skill of the art.

Part A. Synthetic Procedures

Synthesis procedures for preparation of the compounds of the invention are readily available to the ordinary skilled artisan. For example, U.S. Pat. No. 7,262,298; PCT publication WO2012/088494; U.S. Pat. No. 8,252,929; U.S. Pat. No. 8,026,252; Neumeyer et al. (Journal of Med. Chem. 2012, p. 3878); and U.S. Pat. No. 8,252,929 provide synthesis methods that can be used or easily adapted to make the compounds of Formulas I, II, III, and IV, and Table A. All of the above-referenced patents and references are incorporated herein by reference in their entirety.

The following are illustrative examples of synthesizing certain particular compounds provided in this disclosure. One skilled in the art will readily apply and/or adapt these methods to synthesize the compounds provided herein, e.g., the compounds of Formulas I, II, III, and IV, and Table A.

General Procedure to Synthesize a NH Core Compound

Synthesis of (4R,4aR,7aR,12bS)-3-methyl-1,2,3,4, 4a,5,6,7a-octahydrospiro[4,12-methanobenzofuro[3, 2-e]isoquinoline-7,2'-[1,3]dioxolan]-9-ol

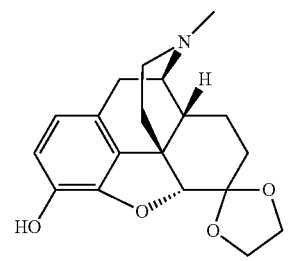

To Hydromorphone HCl (15.0 g, 46.7 mmol) was added ethylene glycol (80 mL) and methane sulfonic acid (10 mL) and the reaction heated at 80° C. overnight. The reaction was cooled to room temperature and poured into ice/NH$_{3(aq)}$ (~350 mL). The product was extracted with dichloromethane and dried over MgSO$_4$ before concentration under reduced pressure to give (4R,4aR,7aR,12bS)-3-methyl-1,2, 3,4,4a,5,6,7a-octahydrospiro[4,12-methanobenzofuro[3,2-e]isoquinoline-7,2'-[1,3]dioxolan]-9-ol (19 g, 99.9% LCMS); [M+H]$^+$ 330.5. This was taken onto the next step without purification.

Synthesis of (4R,4aR,7aR,12bS)-3-methyl-1,2,3,4, 4a,5,6,7a-octahydrospiro[4,12-methanobenzofuro[3, 2-e]isoquinoline-7,2'-[1,3]dioxolan]-9-yl trifluoromethanesulfonate

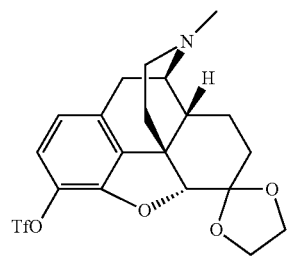 [SMILES: CN1CC[C@]23c4c5ccc(OS(=O)(=O)C(F)(F)F)c4O[C@H]2C2(CC[C@H]3[C@H]1C5)OCCO2]

To a mixture of (4R,4aR,7aR,12bS)-3-methyl-1,2,3,4,4a, 5,6,7a-octahydrospiro[4,12-methanobenzofuro[3,2-e]isoquinoline-7,2'-[1,3]dioxolan]-9-ol (21.54 g, 46.73 mmol)

and triethylamine (20 mL, 140.2 mmol) in dichloromethane (600 mL) was added N-Phenylbis(trifluoromethanesulfonamide) (17.53 g, 49.0 mmol) and the mixture stirred at room temperature overnight. The solvent was concentrated under reduced pressure and the residue taken up in 20% hexane in ethyl acetate (1 L) and washed with water (×5). The organic phase was dried (MgSO$_4$). Filtration and removal of the solvent under reduced pressure gave (4R,4aR,7aR,12bS)-3-methyl-1,2,3,4,4a,5,6,7a-octahydrospiro[4,12-methanobenzofuro[3,2-e]isoquinoline-7,2'-[1,3]dioxolan]-9-yl trifluoromethanesulfonate (20.77 g, 96% pure LCMS); [M+H]$^+$ 462.1.

Synthesis of (4R,4aR,7aR,12bS)-3-methyl-1,2,3,4,4a,5,6,7a-octahydrospiro[4,12-methanobenzofuro[3,2-e]isoquinoline-7,2'-[1,3]dioxolane]-9-carbonitrile

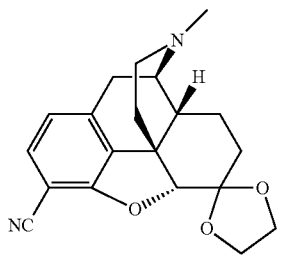 [SMILES: CN1CC[C@]23c4c5ccc(C#N)c4O[C@H]2C2(CC[C@H]3[C@H]1C5)OCCO2]

To a solution of (4R,4aR,7aR,12bS)-3-methyl-1,2,3,4,4a,5,6,7a-octahydrospiro[4,12-methanobenzofuro[3,2-e]isoquinoline-7,2'-[1,3]dioxolan]-9-yl trifluoromethanesulfonate (20.77 g, 45.0 mmol) in degassed dimethylformamide (400 mL) was added tetrakis(triphenylphosphine)palladium (0) (5.21 g, 4.50 mmol). After heating to 40° C., zinc cyanide (3.18 g, 27.0 mmol) was added and the reaction mixture heated at 110° C. for 6 hours. The reaction mixture was cooled to room temperature and diluted with ethyl acetate and filtered through a pad of celite. The filtrate was diluted further with ethyl acetate and washed with water (3×500 mL). The aqueous phase was basified with sodium hydrogen carbonate solution and re-extracted with ethyl acetate and the combined organics dried (MgSO$_4$), filtered and concentrated under reduced pressure. Purification by silica chromatography (100% dichloromethane to 5% NH$_3$/methanol in dichloromethane) gave (4R,4aR,7aR,12bS)-3-methyl-1,2,3,4,4a,5,6,7a-octahydrospiro[4,12-methanobenzofuro[3,2-e]isoquinoline-7,2'-[1,3]dioxolane]-9-carbonitrile (10.0 g, 91% pure LCMS, 63% yield over three steps); [M+H]$^+$ 339.1.

Synthesis of (4R,4aR,7aR,12bS)-1,2,3,4,4a,5,6,7a-octahydrospiro[4,12-methanobenzofuro[3,2-e]isoquinoline-7,2'-[1,3]dioxolane]-9-carbonitrile

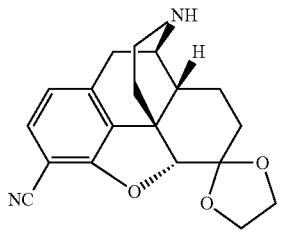 [SMILES: N#Cc1ccc2c3c1O[C@H]1C4(CC[C@H]5[C@@H](C2)NCC[C@@]351)OCCO4]

To a suspension of (4R,4aR,7aR,12bS)-3-methyl-1,2,3,4,4a,5,6,7a-octahydrospiro[4,12-methanobenzofuro[3,2-e]isoquinoline-7,2'-[1,3]dioxolane]-9-carbonitrile (5.0 g, 17.8 mmol) in dimethylformamide (50 mL) was added diisopropyl azodicarboxylate (5.4 mL, 27.5 mmol). The reaction was heated to 55° C. for 3 hours until the starting material was consumed. To the reaction was added dimedone (5.8 g, 41.4 mmol) and methanol (1.75 mL, 54.8 mmol) and the reaction heated to 60° C. for 3 hours. The reaction was allowed to cool to room temperature and poured into 0.5 M HCl$_{(aq)}$ (50 mL). The aqueous phase was washed with diethyl ether:ethyl acetate (3:1). The organic phase was back extracted with 0.5 M HCl$_{(aq)}$ and acidic phases combined before basifying with 2M NaOH until pH9. The aqueous phase was extracted with ethyl acetate (×3). The combined organic phases were washed with water/brine (×3) before drying over MgSO$_4$ and concentrating under reduced pressure. The residue was purified by silica chromatography (5% methanol in dichloromethane to 5% NH$_3$/methanol in dichloromethane) to give (4R,4aR,7aR,12bS)-1,2,3,4,4a,5,6,7a-octahydrospiro[4,12-methanobenzofuro[3,2-e]isoquinoline-7,2'-[1,3]dioxolane]-9-carbonitrile as a pale yellow solid (3.90 g, 95% pure LCMS, 81% yield); [M+H]$^+$ 325.1.

General Procedure to Synthesize a Deoxygenated Core Compound

Synthesis of (4R,4aR,7aR,12bS)-9-(benzyloxy)-3-methyl-2,3,4,4a,5,6-hexahydro-1H-4,12-methanobenzofuro[3,2-e]isoquinolin-7 (7aH)-one

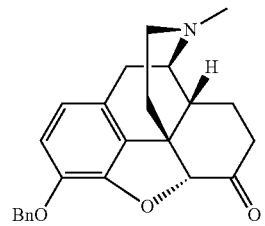

To Hydromorphone HCl (50.0 g, 155.3 mmol) in dimethylformamide (500 mL) was added sodium hydride (14.30 g, 357.4 mmol) portionwise with cooling. The addition was conducted over 25 minutes. The reaction was stirred at room temperature for 1.5 hours before the addition of benzyl chloride (17.88 mL, 357.4 mmol) over 10 minutes with cooling. The reaction was allowed to warm to room temperature and stirred for 40 hours. The reaction was incomplete so additional benzyl chloride (1.79 mL, 15.5 mmol) was added. After 4 hours, the reaction was quenched with water (60 mL), acidified with aqueous HCl (2M, 800 mL) and washed with ethyl acetate/diethyl ether (3:1) (2×800 mL). The aqueous phase was basified with aqueous NaOH (2M, 800 mL) and extracted with ethyl acetate (2×1 L). The organic phases were combined, washed with water/brine (1:1) (2×800 mL) and dried over MgSO$_4$ before concentration under reduced pressure. The residue was taken up in ethyl acetate and washed with water/brine (2×500 mL), dried over MgSO$_4$ before concentration under reduced pressure to give (4R,4aR,7aR,12bS)-9-(benzyloxy)-3-methyl-2,3,4,4a,5,6-hexahydro-1H-4,12-methanobenzofuro[3,2-e]isoquinolin-7(7aH)-one (47.9 g, 95% pure by NMR, 82% yield); [M+H]$^+$ 376.2. This was taken onto the next step without purification.

Synthesis of (4bS,8aR,9R)-3-(benzyloxy)-4-hydroxy-11-methyl-8,8a,9,10-tetrahydro-5H-9,4b-(epiminoethano)phenanthren-6(7H)-one

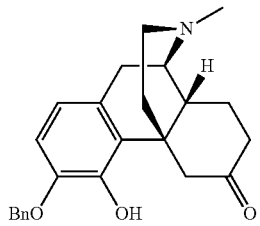

To (4R,4aR,7aR,12bS)-9-(benzyloxy)-3-methyl-2,3,4,4a,5,6-hexahydro-1H-4,12-methanobenzofuro[3,2-e]isoquinolin-7(7aH)-one (58.32 g, 0.16 mol) in ethanol (1.55 L) was added ammonium chloride (124.65 g, 2.33 mol) and zinc powder (101.59 g, 1.55 mol). The reaction was heated to reflux and monitored by TLC. Once complete, the reaction was allowed to cool and filtered through a pad of celite. The pad was washed thoroughly with ethanol (1 L) and methanol (1 L). The filtrate was concentrated under reduced pressure. The residue was taken up in dichloromethane and aqueous ammonia (~15%, 1 L) before the product was extracted with dichloromethane (3×700 mL). The dichloromethane phases were combined, washed with brine and dried over $MgSO_4$ before being concentrated under reduced pressure. The residue was purified by silica chromatography eluted with 10% methanol, 5% $Et_3N$ in dichloromethane to give (4bS,8aR,9R)-3-(benzyloxy)-4-hydroxy-11-methyl-8,8a,9,10-tetrahydro-5H-9,4b-(epiminoethano)phenanthren-6(7H)-one (50.4 g, 74.3% pure LCMS, 64% yield); $[M+H]^+$ 378.2.

Synthesis of (4bS,8aR,9R)-3-(benzyloxy)-11-methyl-6-oxo-6,7,8,8a,9,10-hexahydro-5H-9,4b-(epiminoethano)phenanthren-4-yl trifluoromethanesulfonate

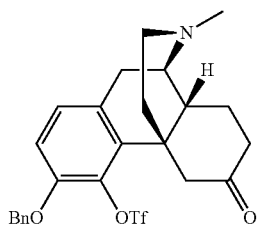

To a solution of (4bS,8aR,9R)-3-(benzyloxy)-4-hydroxy-1-methyl-8,8a,9,10-tetrahydro-5H-9,4b-(epiminoethano) phenanthren-6(7H)-one (28.2 g, 74.7 mmol) in tetrahydrofuran under an atmosphere of argon at 0° C. was added sodium hydride (4.48 g, 112.1 mmol) portionwise. The reaction was stirred for 30 minutes before N-Phenylbis (trifluoromethanesulfonamide) (40.03 g, 112.1 mmol) was added. The reaction was left to warm to room temperature overnight. The reaction was cooled to 0° C. and quenched with IPA followed by water. The solution was diluted with ethyl acetate/heptanes (1:1) and aqueous ammonia (30%, 400 mL) added. The phases were separated and the organic phase washed with aqueous ammonia (15%) twice before being washed with brine, dried over $MgSO_4$ and concentrated under reduced pressure. The residue was purified by silica chromatography eluted with a gradient from 2.5-10% methanol/dichloromethane to give (4bS,8aR,9R)-3-(benzyloxy)-11-methyl-6-oxo-6,7,8,8a,9,10-hexahydro-5H-9,4b-(epiminoethano)phenanthren-4-yl trifluoromethanesulfonate (31.6 g, 81% pure LCMS, 67% yield); $[M+H]^+$ 510.2.

Synthesis of (4bS,8aR,9R)-3-(benzyloxy)-11-methyl-8,8a,9,10-tetrahydro-5H-9,4b-(epiminoethano)phenanthren-6(7H)-one

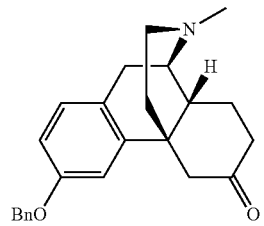

To a solution of (4bS,8aR,9R)-3-(benzyloxy)-11-methyl-6-oxo-6,7,8,8a,9,10-hexahydro-5H-9,4b-(epiminoethano) phenanthren-4-yl trifluoromethanesulfonate (31.9 g, 62.6 mmol) in degassed dimethylformamide (320 mL) was added $Pd(OAc)_2$ (1.405 g, 6.6 mmol), 1,3-bis(diphenylphosphino) propane (2.58 g, 6.3 mmol) and triethylsilane (100 mL, 626.0 mmol). The reaction was heated to 86° C. under argon for 4 hours. The reaction was cooled to room temperature, quenched with 2M HCl and extracted with diethyl ether: ethyl acetate (1:1). The organic phase was washed with 2M HCl. The acid phases were combined and washed with diethyl ether: ethyl acetate (1:1) (×3). The aqueous phase was basified with 2M NaOH and extracted with ethyl acetate (×3). The organic phase was washed with water (×3) and then brine before being dried over $MgSO_4$ and concentrated under reduced pressure to give (4bS,8aR,9R)-3-(benzyloxy)-11-methyl-8,8a,9,10-tetrahydro-5H-9,4b-(epiminoethano)phenanthren-6(7H)-one (20.2 g, 85% pure LCMS); $[M+H]^+$ 362.3. This was taken onto the next step without purification.

Synthesis of (4bS,8aR,9R)-3-(benzyloxy)-11-methyl-5,7,8,8a,9,10-hexahydrospiro[9,4b-(epiminoethano)phenanthrene-6,2'-[1,3]dioxolane]

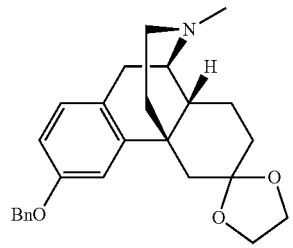

To a suspension of (4bS,8aR,9R)-3-(benzyloxy)-11-methyl-8,8a,9,10-tetrahydro-5H-9,4b-(epiminoethano) phenanthren-6(7H)-one (20.2 g, 55.9 mmol) in ethylene glycol (280 mL) was added methane sulfonic acid (14.5 mL, 223.5 mmol). The reaction went into solution and was stirred at room temperature for 16 hours. The reaction was poured into aqueous ammonia/ice and was extracted with ethyl acetate (×3). The organics were combined, washed with water/brine (×3) and dried over MgSO$_4$ and concentrated under reduced pressure to give (4bS,8aR,9R)-3-(benzyloxy)-11-methyl-5,7,8,8a,9,10-hexahydrospiro[9,4b-(epiminoethano)phenanthrene-6,2'-[1,3]dioxolane](18.6 g, 84% pure UPLC); [M+H]$^+$ 406.3. This was taken onto the next step without purification.

Synthesis of (4bS,8aR,9R)-11-methyl-5,7,8,8a,9,10-hexahydrospiro[9,4b-(epiminoethano)phenanthrene-6,2'-[1,3]dioxolan]-3-ol

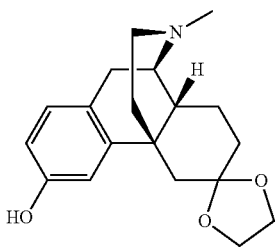

To a solution of (4bS,8aR,9R)-3-(benzyloxy)-11-methyl-5,7,8,8a,9,10-hexahydrospiro[9,4b-(epiminoethano)phenanthrene-6,2'-[1,3]dioxolane](21.8 g, 53.8 mmol) in ethanol (545 mL) was added 10% palladium on carbon (2.2 g, 0.1 eq by weight) and the reaction placed under an atmosphere of hydrogen. The reaction was stirred for 16 hours at room temperature. The reaction was filtered through a pad of celite and the filtrate concentrated under reduced pressure to give (4bS,8aR,9R)-11-methyl-5,7,8,8a,9,10-hexahydrospiro[9,4b-(epiminoethano)phenanthrene-6,2'-[1,3]dioxolan]-3-ol (16.9 g, 73% pure LCMS); [M+H]$^+$ 316.2. This was taken onto the next step without purification.

Synthesis of (4bS,8aR,9R)-11-methyl-5,7,8,8a,9,10-hexahydrospiro[9,4b-(epiminoethano)phenanthrene-6,2'-[1,3]dioxolan]-3-yl trifluoromethanesulfonate

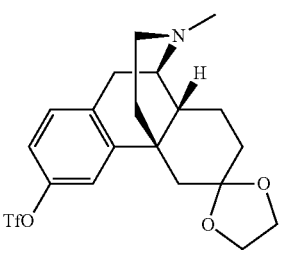

To a mixture of (4bS,8aR,9R)-11-methyl-5,7,8,8a,9,10-hexahydrospiro[9,4b-(epiminoethano)phenanthrene-6,2'-[1,3]dioxolan]-3-ol (16.95 g, 53.7 mmol) and triethylamine (22.5 mL, 161.2 mmol) in dichloromethane (400 mL) was added N-Phenylbis(trifluoromethanesulfonamide) (19.77 g, 55.4 mmol) and the mixture stirred at room temperature overnight. The solvent was concentrated under reduced pressure and the residue taken up in ethyl acetate. The organic phase was washed with aqueous ammonia/water (1:1×3) before washing with brine. The organic phase was dried over MgSO$_4$ and concentrated under reduced pressure. The residue was purified by silica chromatography eluted with 0-10% methanol in dichloromethane to give (4bS,8aR,9R)-11-methyl-5,7,8,8a,9,10-hexahydrospirospiro[9,4b-(epiminoethano)phenanthrene-6,2'-[1,3]dioxolan]-3-yl trifluoromethanesulfonate (18.7 g, 76.8% pure LCMS, 57.7% over 4 steps); [M+H]$^+$ 448.2.

Synthesis of (4bS,8aR,9R)-11-methyl-5,7,8,8a,9,10-hexahydrospiro[9,4b-(epiminoethano)phenanthrene-6,2'-[1,3]dioxolane]-3-carbonitrile

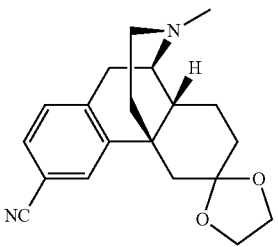

To a solution of (4bS,8aR,9R)-11-methyl-5,7,8,8a,9,10-hexahydrospirospiro[9,4b-(epiminoethano)phenanthrene-6,2'-[1,3]dioxolan]-3-yl trifluoromethanesulfonate (18.7 g, 41.8 mmol) in degassed dimethylformamide (250 mL) was added tetrakis(triphenylphosphine)palladium(0) (4.83 g, 4.2 mmol). After heating to 40° C., zinc cyanide (2.94 g, 25.0 mmol) was added and the reaction mixture heated at 130° C. for 24 hours. Reaction incomplete so cooled to room temperature and tetrakis(triphenylphosphine)palladium(0) (4.83 g, 4.2 mmol) was added and the reaction heated to 135° C. for 4 hours. The reaction mixture was cooled to room temperature and diluted with ethyl acetate and quenched with sodium hydrogen carbonate solution. The mixture was filtered through a pad of celite. The phases were separated and the product extracted with ethyl acetate (×3). The organic phases were combined, washed with water/brine (×3), dried over MgSO$_4$ and concentrated under reduced pressure. Purification by silica chromatography (100% dichloromethane to 5% NH$_3$/methanol in dichloromethane) gave (4bS,8aR,9R)-11-methyl-5,7,8,8a,9,10-hexahydrospiro[9,4b-(epiminoethano)phenanthrene-6,2'-[1,3]dioxolane]-3-carbonitrile (8.26 g, 89% pure LCMS). [M+H]$^+$ 325.2.

Synthesis of (4bS,8aR,9R)-5,7,8,8a,9,10-hexahydrospiro[9,4b-(epiminoethano)phenanthrene-6,2'-[1,3]dioxolane]-3-carbonitrile

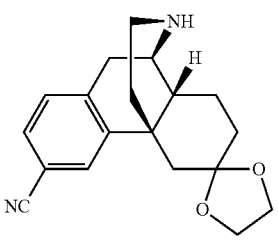

To a suspension of (4bS,8aR,9R)-11-methyl-5,7,8,8a,9,10-hexahydrospiro[9,4b-(epiminoethano)phenanthrene-6,2'-[1,3]dioxolane]-3-carbonitrile (8.26 g, 25.5 mmol) in dimethylformamide (65 mL) was added diisopropyl azodicarboxylate (9.32 mL, 47.4 mmol). The reaction was heated to 55° C. for 4 hours until starting material is consumed. To the reaction was added dimedone (9.99 g, 71.3 mmol) and methanol (3.1 mL, 94.2 mmol) and the reaction heated to 60° C. for 3 hours. The reaction was allowed to cool to room temperature overnight. The reaction was poured into 0.5 M HCl$_{(aq)}$ (250 mL) and washed with diethyl ether:ethyl acetate (3:1). The organic phase was back extracted with 0.5 M HCl$_{(aq)}$ (250 mL) and the acidic phases combined before basifying with 2M NaOH until pH9. The aqueous phase was extracted with ethyl acetate (×3). The combined organic phases were washed with water/brine (×3) before drying over MgSO$_4$ and concentrating under reduced pressure. The residue was purified by silica chromatography (100% dichloromethane to 10% NH$_3$/methanol in dichloromethane) to give (4bS,8aR,9R)-5,7,8,8a,9,10-hexahydrospiro[9,4b-(epiminoethano)phenanthrene-6,2'-[1,3]dioxolane]-3-carbonitrile (5.95 g, 42% yield over two steps, 92% pure LCMS); [M+H]$^+$ 311.2.

A1. Experimental Procedure for Compound A and a Hydrochloride Salt Thereof

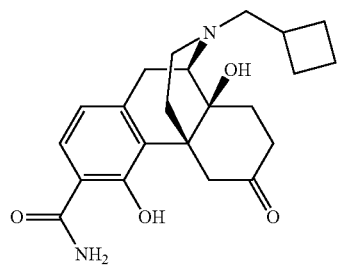

Chemical Formula: C$_{22}$H$_{28}$N$_2$O$_4$
Exact Mass: 384.20
Molecular Weight: 384.48

2-Cyclobutanecarbaldehyde

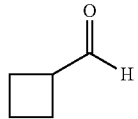

Chemical Formula: C$_5$H$_8$O
Exact Mass: 84.06
Molecular Weight: 84.12

To a mixture of Pyridinium chlorochromate (41.3 g, 191.6 mmol) in dichloromethane (120 mL) was added Cyclobutanemethanol (7.5 g, 87.1 mmol). The mixture was stirred for 1.5 hours then filtered through a pad of silica and rinsed with further dichloromethane (300 mL). The solvent was removed under reduced pressure to give 2-cyclobutylcarbaldehyde (10.0 g, contains residual dichloromethane) that was used without further purification.

(4R,4aS,7aR,12bS)-3-(cyclobutylmethyl)-4a,9-dihydroxy-2,3,4,4a,5,6-hexahydro-1H-4,12-methanobenzofuro[3,2-e]isoquinolin-7(7aH)-one

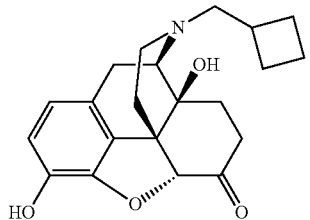

Chemical Formula: C$_{21}$H$_{25}$NO$_4$
Exact Mass: 355.18
Molecular Weight: 355.43

A mixture of Noroxymorphone (8.8 g, 30.6 mmol) in methanol (250 mL) was degassed for 20 minutes. 2-cyclobutanecarbaldehyde (7.7 g, 91.5 mmol) was added and the mixture heated at reflux for 1 hour. The reaction mixture was cooled to ambient temperature. In a separate flask formic acid (14.0 g, 306 mmol) was added slowly to a solution of triethylamine (12.4 g, 123 mmol) in methanol (40 mL). The formic acid solution was stirred for 5 minutes before being added to the solution containing Noroxymorphone along with dichloro(p-cymene)ruthenium(II) dimer (53 mg). The reaction was heated at reflux for a further 2.5 hours. The reaction was concentrated under reduced pressure then partitioned between ethyl acetate and saturated sodium bicarbonate solution. The aqueous phase was extracted with further ethyl acetate then the organic layers combined and dried (MgSO$_4$). Filtration and removal of the solvent under reduced pressure gave (4R,4aS,7aR,12bS)-3-(cyclobutylmethyl)-4a,9-dihydroxy-2,3,4,4a,5,6-hexahydro-1H-4,12-methanobenzofuro[3,2-e]isoquinolin-7(7aH)-one (10.2 g, 94% yield); LC/MS (M+H)$^+$=356.2.

(4R,4aS,7aR,12bS)-3-(cyclobutylmethyl)-4a-hydroxy-7-oxo-2,3,4,4a,5,6,7,7a-octahydro-1H-4,12-methanobenzofuro[3,2-e]isoquinolin-9-yl trifluoromethanesulfonate

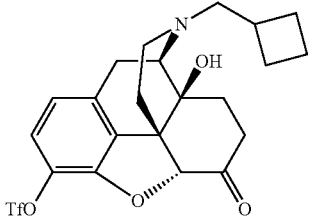

Chemical Formula: C$_{22}$H$_{24}$F$_3$NO$_6$S
Exact Mass: 487.13
Molecular Weight: 487.49

To a solution of (4R,4aS,7aR,12bS)-3-(cyclobutylmethyl)-4a,9-dihydroxy-2,3,4,4a,5,6-hexahydro-1H-4,12-methanobenzofuro[3,2-e]isoquinolin-7(7 aH)-one (10.2 g, 28.7 mmol) and triethylamine (12.2 mL, 88.3 mmol) in dichloromethane (200 mL) was added N-Phenylbis(trifluoromethanesulfonamide) (11.0 g, 30.9 mmol) and the mixture stirred at room temperature overnight. The solvent was concentrated under reduced pressure and the residue partitioned between 20% hexane in ethyl acetate (500 mL) and water (300 mL). The organic layer was washed twice more with water and dried (MgSO$_4$). Filtration and removal of the solvent under reduced pressure gave (4R,4aS,7aR,12bS)-3-(cyclobutylmethyl)-4a-hydroxy-7-oxo-2,3,4,4a,5,6,7,7a-octahydro-1H-4,12-methanobenzofuro[3,2-e]isoquinolin-9-yl trifluoromethanesulfonate (14.3 g, 100% yield); LC/MS (M+H)$^+$=488.1.

(4R,4aS,7aR,12bS)-3-(cyclobutylmethyl)-N-(2,4-dimethoxybenzyl)-4a-hydroxy-7-oxo-2,3,4,4a,5,6,7,7a-octahydro-1H-4,12-methanobenzofuro[3,2-e]isoquinoline-9-carboxamide

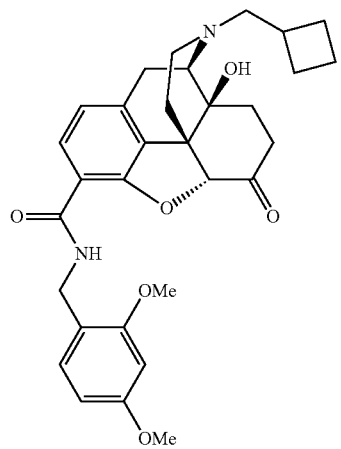

Chemical Formula: C$_{31}$H$_{36}$N$_2$O$_6$
Exact Mass: 532.26
Molecular Weight: 532.63

To a solution of (4R,4aS,7aR,12bS)-3-(cyclobutylmethyl)-4a-hydroxy-7-oxo-2,3,4,4a,5,6,7,7a-octahydro-1H-4,12-methanobenzofuro[3,2-e]isoquinolin-9-yl trifluoromethanesulfonate (14.3 g, 29.3 mmol) in degassed dimethyl sulfoxide (185 mL), was added N-hydroxysuccinimide (6.8 g, 58.7 mmol), palladium acetate (0.66 g, 2.93 mmol), triethylamine (8.2 mL, 58.7 mmol) and 4,5-bis(diphenylphosphino)-9,9-dimethylxanthene (1.7 g, 2.93 mmol). The reaction mixture was heated with carbon monoxide (1 atm) at 75° C. overnight. The reaction mixture was cooled to ambient temperature and 2,4-dimethoxybenzylamine (4.9 g, 29.3 mmol) added. The mixture was stirred for 1 hour before partitioning between water (2 L) and ethyl acetate (1 L). The aqueous phase was extracted twice more with ethyl acetate. The combined organic phase was dried (MgSO$_4$), filtered, and the solvent removed under reduced pressure. The crude material was purified by silica chromatography (3% methanol in dichloromethane) to give (4R,4aS,7aR,12bS)-3-(cyclobutylmethyl)-N-(2,4-dimethoxybenzyl)-4a-hydroxy-7-oxo-2,3,4,4a,5,6,7,7a-octahydro-1H-4,12-methanobenzofuro[3,2-e]isoquinoline-9-carboxamide (14.4 g, 55% yield); LC/MS (M+H)$^+$=533.3.

(4R,4aS,7aR,12bS)-3-(cyclobutylmethyl)-4a-hydroxy-7-oxo-2,3,4,4a,5,6,7,7a-octahydro-1H-4,12-methanobenzofuro[3,2-e]isoquinoline-9-carboxamide

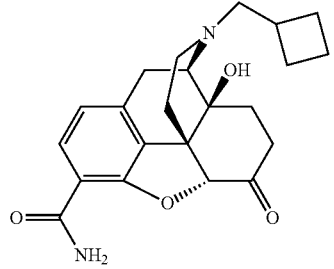

Chemical Formula: C$_{22}$H$_{26}$N$_2$O$_4$
Exact Mass: 382.19
Molecular Weight: 382.45

A mixture of (4R,4aS,7aR,12bS)-3-(cyclobutylmethyl)-N-(2,4-dimethoxybenzyl)-4a-hydroxy-7-oxo-2,3,4,4a,5,6,7,7a-octahydro-1H-4,12-methanobenzofuro[3,2-e]isoquinoline-9-carboxamide (14.4 g, 27.0 mmol) in trifluoroacetic acid was stirred at ambient temperature for 2 hours. The trifluoroacetic acid was removed under reduced pressure and the residue quenched with 300 mL of ammonium hydroxide (6%). The product was extracted twice into dichloromethane (300 mL), the organic phases combined and dried (MgSO$_4$). Filtration and removal of the solvent under reduced pressure gave (4R,4aS,7aR,12bS)-3-(cyclobutylmethyl)-4a-hydroxy-7-oxo-2,3,4,4a,5,6,7,7a-octahydro-1H-4,12-methanobenzofuro[3,2-e]isoquinoline-9-carboxamide (9.0 g, 87% yield); LC/MS (M+H)$^+$=383.2.

4bR,8aS,9R)-11-(cyclobutylmethyl)-4,8a-dihydroxy-6-oxo-6,7,8,8a,9,10-hexahydro-5H-9,4b-(epiminoethano)phenanthrene-3-carboxamide (Compound A)

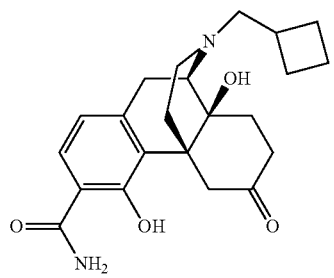

Chemical Formula: C$_{22}$H$_{28}$N$_2$O$_4$
Exact Mass: 384.20
Molecular Weight: 384.47

To a mixture of (4R,4aS,7aR,12bS)-3-(cyclobutylmethyl)-4a-hydroxy-7-oxo-2,3,4,4a,5,6,7,7a-octahydro-1H-4,12-methanobenzofuro[3,2-e]isoquinoline-9-carboxamide (4.5 g, 11.8 mmol), and zinc powder (29.0 g, 444 mmol) in acetic acid (135 mL) was added conc. HCl (25.5 mL). The mixture was heated to 125° C. for 2 hours. The reaction mixture was cooled to ambient temperature and quenched into ice/ammonium hydroxide solution (1 L, 28%). The product was extracted into dichloromethane (1 L) and dried (MgSO$_4$). Filtration and removal of the solvent under reduced pressure gave the crude material which was purified by silica chromatography (7.5% methanol/ammonia in DCM) followed by recrystallisation from methanol to give (4bR,8aS,9R)-11-(cyclobutylmethyl)-4,8a-dihydroxy-6-oxo-6,7,8,8a,9,10-hexahydro-5H-9,4b-(epiminoethano) phenanthrene-3-carboxamide (2.1 g, 46% yield); LC/MS (M+H)$^+$=385.2.

(4bR,8aS,9R)-11-(cyclobutylmethyl)-4,8a-dihydroxy-6-oxo-6,7,8,8a,9,10-hexahydro-5H-9,4b-(epiminoethano)phenanthrene-3-carboxamide hydrochloride

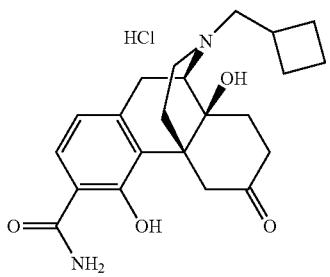

Chemical Formula: C$_{22}$H$_{29}$ClN$_2$O$_4$
Exact Mass: 420.18
Molecular Weight: 420.93

To a solution of (4bR,8aS,9R)-11-(cyclobutylmethyl)-4,8a-dihydroxy-6-oxo-6,7,8,8a,9,10-hexahydro-5H-9,4b-(epiminoethano)phenanthrene-3-carboxamide (2.1 g, 5.46 mmol) in ethyl acetate (100 mL) was added 2N HCl/ether (6 mL, 12 mmol) and the mixture stirred for 4 hours. The solvent was removed under reduced pressure and dried (55° C.) giving (4bR,8aS,9R)-11-(cyclobutylmethyl)-4,8a-dihydroxy-6-oxo-6,7,8,8a,9,10-hexahydro-5H-9,4b-(epiminoethano)phenanthrene-3-carboxamide hydrochloride (2.25 g, 98% yield); LC/MS (M+H)$^+$=385.2. $^1$H-NMR (400 MHz, DMSO) δ 8.98 (br s, 1H), 8.45 (s, 1H), 7.96 (s, 1H), 7.68 (d, 1H), 6.64 (d, 1H), 6.33 (s, 1H), 3.85 (d, 1H), 3.45 (br s, 1H), 3.29 (br s, 3H+H$_2$O), 3.15-2.91 (m, 2H), 2.74-2.60 (m, 3H), 2.40-2.10 (m, 2H), 2.12-1.55 (m, 10H).

A2. Experimental Procedure for Compound D and a Hydrochloride Salt Thereof

4bR,6R,8aS,9R)-11-(cyclobutylmethyl)-4,6,8a-trihydroxy-6,7,8,8a,9,10-hexahydro-5H-9,4b-(epiminoethano)phenanthrene-3-carboxamide (Compound D)

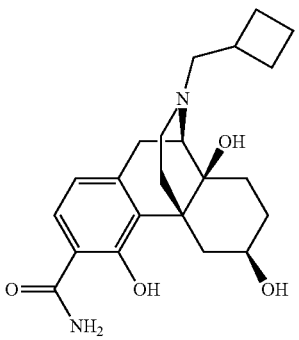

Chemical Formula: C$_{22}$H$_{30}$N$_2$O$_4$
Exact Mass: 386.22
Molecular Weight: 386.48

A solution of formamidinesulfinic acid (1.12 g, 10.4 mmol, 4.00 eq.) in 0.5 M aqueous sodium hydroxide (20 mL) was added dropwise over 10 minutes to a stirred solution of (4bR,8aS,9R)-11-(cyclobutylmethyl)-4,8a-dihydroxy-6-oxo-6,7,8,8a,9,10-hexahydro-5H-9,4b-(epiminoethano) phenanthrene-3-carboxamide (1.00 g, 2.60 mmol, 1.00 eq.) in 0.5 N NaOH$_{(aq)}$ (30 mL) at ambient temperature under argon. The mixture was heated to 80° C. under argon for 12 hours and then cooled to room temperature. The precipitated solid was collected by filtration and then washed with water (2×10 mL) and diethyl ether (2×20 mL). The solid was recrystallised in methanol and then dried at 50° C. under vacuum for 3 hours to leave (4bR,6R,8aS,9R)-11-(cyclobutylmethyl)-4,6,8a-trihydroxy-6,7,8,8a,9,10-hexahydro-5H-9,4b-(epiminoethano)phenanthrene-3-carboxamide as colourless crystals (400 mg, 40% yield); LC/MS (M+H)$^+$=387.26.

(4bR,6R,8aS,9R)-11-(cyclobutylmethyl)-4,6,8a-trihydroxy-6,7,8,8a,9,10-hexahydro-5H-9,4b-(epiminoethano)phenanthrene-3-carboxamide hydrochloride

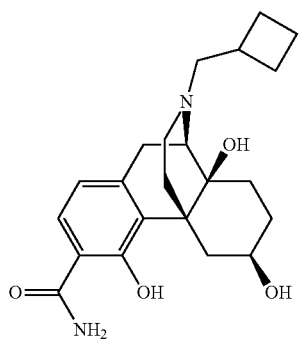

Chemical Formula: C$_{22}$H$_{30}$N$_2$O$_4$
Exact Mass: 386.22
Molecular Weight: 386.48

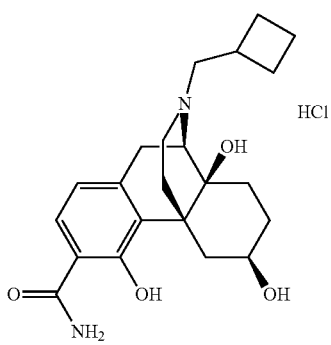

Chemical Formula: C$_{22}$H$_{31}$ClN$_2$O$_4$
Exact Mass: 422.20
Molecular Weight: 422.95

A solution of hydrochloric acid (0.40 mL, 2.0 M in diethyl ether) was added dropwise over 5 minutes to a stirred solution of (4bR,6R,8aS,9R)-11-(cyclobutylmethyl)-4,6,8a-trihydroxy-6,7,8,8a,9,10-hexahydro-5H-9,4b-(epiminoethano) phenanthrene-3-carboxamide (400 mg, 1.03 mmol, 1.00 eq.) in ethyl acetate (4 mL) at ambient temperature under argon. The mixture was stirred at ambient temperature under argon for 3 hours and then concentrated under reduced pressure. The solid was dried at 50° C. under vacuum for 1 hour, and then freeze dried to leave (4bR,6R,8aS,9R)-11-(cyclobutylmethyl)-4,6,8a-trihydroxy-6,7,8,8a,9,10-hexahydro-5H-9,4b-(epiminoethano)phenanthrene-3-carboxamide hydrochloride as a colourless solid (379 mg, 87%); LC/MS (M+H)$^+$=387.26. $^1$H NMR (300 MHz, CDCl3, 614-181-1_1H-1.jdf): 14.43 (s, 1H), 8.80 (br. s, 1H), 8.47 (s, 1H), 7.95 (s, 1H), 7.69 (d, J=8.3 Hz, 1H), 6.63 (d, J=8.3 Hz, 1H), 5.69 (s, 1H), 4.45 (s, 1H), 3.31-3.08 (m, 6H), 3.00-2.81 (m, 2H), 2.70-2.57 (m, 1H), 2.40-2.23 (m, 1H), 2.17-1.91 (m, 3H), 1.90-1.70 (m, 4H), 1.67-1.31 (m, 6H).

A3. Experimental Procedure for Compound C and a Hydrochloride Salt Thereof

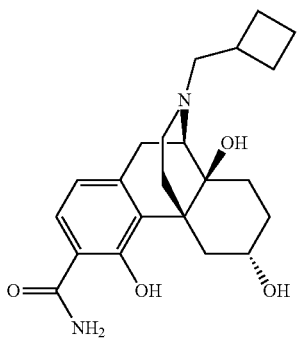

Chemical Formula: $C_{22}H_{30}N_2O_4$
Exact Mass: 386.22
Molecular Weight: 386.48

4bR,6S,8aS,9R)-11-(cyclobutylmethyl)-4,6,8a-trihydroxy-6,7,8,8a,9,10-hexahydro-5H-9,4b-(epiminoethano)phenanthrene-3-carboxamide (Compound C)

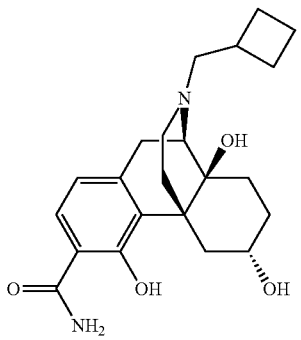

Chemical Formula: $C_{22}H_{30}N_2O_4$
Exact Mass: 386.22
Molecular Weight: 386.48

A solution of K-selectride (7.80 mL, 7.80 mmol, 3.00 eq., 1.0 M in tetrahydrofuran) was added dropwise over 15 minutes to a stirred solution of (4bR,8aS,9R)-11-(cyclobutylmethyl)-4,8a-dihydroxy-6-oxo-6,7,8,8a,9,10-hexahydro-5H-9,4b-(epiminoethano) phenanthrene-3-carboxamide (1.00 g, 2.60 mmol, 1.00 eq.) in tetrahydrofuran (50 mL) at 0° C. under argon. The mixture was stirred at 0° C. under argon for 2 hours and then water (20 mL) and methanol (50 mL) were carefully added dropwise over 15 minutes. The mixture was neutralised to pH 7 by addition of 2N HCl$_{(aq)}$. The mixture was concentrated under reduced pressure and the solid residue recrystallised in methanol. The solid was washed with methanol (4 mL) and diethyl ether (2×10 mL), and then dried at 50° C. under vacuum for 3 hours to leave (4bR,6S,8aS,9R)-11-(cyclobutylmethyl)-4,6,8a-trihydroxy-6,7,8,8a,9,10-hexahydro-5H-9,4b-(epiminoethano)phenanthrene-3-carboxamide as colourless crystals (750 mg, 74%); LC/MS (M+H)$^+$=387.3.

(4bR,6S,8aS,9R)-11-(cyclobutylmethyl)-4,6,8a-trihydroxy-6,7,8,8a,9,10-hexahydro-5H-9,4b-(epiminoethano)phenanthrene-3-carboxamide hydrochloride

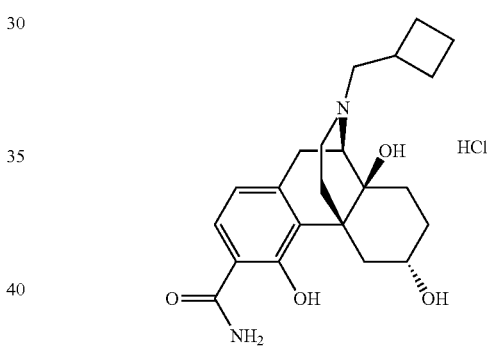

Chemical Formula: $C_{22}H_{31}ClN_2O_4$
Exact Mass: 422.20
Molecular Weight: 422.95

A solution of hydrochloric acid (0.75 mL, 2.0 M in diethyl ether) was added dropwise over 5 minutes to a stirred solution of (4bR,6S,8aS,9R)-11-(cyclobutylmethyl)-4,6,8a-trihydroxy-6,7,8,8a,9,10-hexahydro-5H-9,4b-(epiminoethano) phenanthrene-3-carboxamide (750 mg, 1.94 mmol) in ethyl acetate (10 mL) at ambient temperature under argon. The mixture was stirred at ambient temperature under argon for 3 hours and then concentrated under reduced pressure. The solid was triturated with diethyl ether (2×10 mL), dried at 50° C. under vacuum for 1 hour, then freeze dried to leave (4bR,6S,8aS,9R)-11-(cyclobutylmethyl)-4,6,8a-trihydroxy-6,7,8,8a,9,10-hexahydro-5H-9,4b-(epiminoethano)phenanthrene-3-carboxamide hydrochloride as a colourless solid (695 mg, 85% yield); LC/MS (M+H)$^+$=387.3. $^1$H NMR (300 MHz, DMSO): δ 14.26 (s, 1H), 8.82 (br. s, 1H), 8.36 (s, 1H), 7.79 (s, 1H), 7.60 (d, J=8.3 Hz, 1H), 6.56 (d, J=8.3 Hz, 1H), 5.63 (s, 1H), 3.83 (s, 1H), 3.63 (s, 1H), 3.49-3.36 (m, 1H), 3.29-3.08 (m, 4H), 2.97-2.80 (m, 2H), 2.72-2.58 (m, 1H), 2.36-2.20 (m, 1H), 2.14-1.70 (m, 9H), 1.68-1.49 (m, 2H), 1.38-1.22 (m, 2H).

A4. Experimental Procedure for

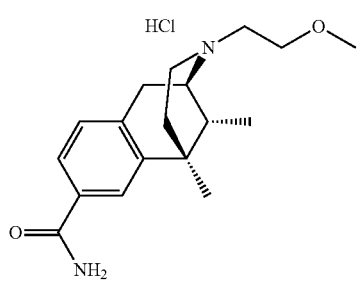

Chemical Formula: C$_{18}$H$_{27}$ClN$_2$O$_2$
Exact Mass: 338.18
Molecular Weight: 338.87

(2R,6R,11R)-tert-butyl 8-hydroxy-6,11-dimethyl-1,2,5,6-tetrahydro-2,6-methanobenzo[d]azocine-3(4H)-carboxylate

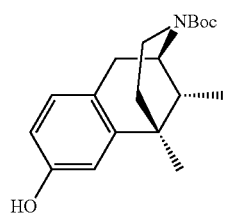

Chemical Formula: C$_{19}$H$_{27}$NO$_3$
Exact Mass: 317.20
Molecular Weight: 317.42

A mixture of (−)-Normetazocine (5.0 g, 23.0 mmol), di-tert-butyl dicarbonate (7.53 g, 34.5 mmol), and sodium hydrogen carbonate (5.80 g, 69.0 mmol), in dichloromethane (170 mL), tetrahydrofuran (170 mL), methanol (85 mL) and water (500 mL) was stirred at ambient temperature overnight. The organic phase was separated and the aqueous phase washed twice with dichloromethane (500 mL). The combined organic phases were dried (MgSO$_4$). Filtration and removal of the solvent under reduced pressure gave oil that was dissolved in industrial methylated spirits (250 mL) and stirred with imidazole (3.0 g, 44.1 mmol) for 1 hour. The solvent was removed under reduced pressure and the residue partitioned between dichloromethane (250 mL) and 0.5N HCl$_{(aq)}$ (250 mL). The organic phase was washed with further acid (250 mL), brine (100 mL), and dried (MgSO$_4$). Filtration and removal of the solvent under reduced pressure gave (2R,6R,11R)-tert-butyl 8-hydroxy-6,11-dimethyl-1,2,5,6-tetrahydro-2,6-methanobenzo[d]azocine-3(4H)-carboxylate (3.9 g, 53% yield); LC/MS (M+H)$^+$=318.5.

(2R,6R,11R)-tert-butyl 6,11-dimethyl-8-(((trifluoromethyl)sulfonyl)oxy)-1,2,5,6-tetrahydro-2,6-methanobenzo[d]azocine-3(4H)-carboxylate

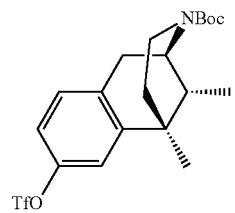

Chemical Formula: C$_{20}$H$_{26}$F$_3$NO$_5$S
Exact Mass: 449.15
Molecular Weight: 449.48

To a solution of (2R,6R,11R)-tert-butyl 8-hydroxy-6,11-dimethyl-1,2,5,6-tetrahydro-2,6-methanobenzo[d]azocine-3(4H)-carboxylate (3.9 g, 12.3 mmol) and triethylamine (5.1 mL, 36.9 mmol) in dichloromethane (100 mL) was added N-Phenylbis(trifluoromethanesulfonamide) (4.61 g, 12.9 mmol) and the mixture stirred at ambient temperature for 4 hours. The solvent was concentrated under reduced pressure and the residue partitioned between 20% hexane in ethyl acetate (500 mL) and water (400 mL). The organic layer was washed four more times more with water and dried (MgSO$_4$). Filtration and removal of the solvent under reduced pressure gave (2R,6R,11R)-tert-butyl 6,11-dimethyl-8-(((trifluoromethyl)sulfonyl)oxy)-1,2,5,6-tetrahydro-2,6-methanobenzo[d]azocine-3(4H)-carboxylate (5.32 g, 96% yield); LC/MS (M+H)$^+$=450.4.

(2R,6R,11R)-tert-butyl 8-((2,4-dimethoxybenzyl)carbamoyl)-6,11-dimethyl-1,2,5,6-tetrahydro-2,6-methanobenzo[d]azocine-3(4H)-carboxylate

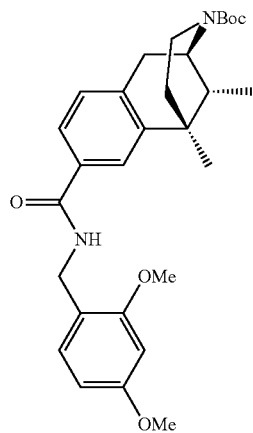

Chemical Formula: C$_{29}$H$_{38}$N$_2$O$_5$
Exact Mass: 494.28
Molecular Weight: 494.62

To a solution of (2R,6R,11R)-tert-butyl 6,11-dimethyl-8-(((trifluoromethyl)sulfonyl)oxy)-1,2,5,6-tetrahydro-2,6- methanobenzo[d]azocine-3(4H)-carboxylate (5.32 g, 11.8 mmol) in degassed dimethyl sulfone (50 mL), was added N-hydroxysuccinimide (2.73 g, 23.7 mmol), palladium acetate (265 mg, 1.18 mmol), triethylamine (3.3 mL, 23.7 mmol) and 4,5-bis(diphenylphosphino)-9,9-dimethylxanthene (683 mg, 1.18 mmol). The reaction mixture was heated with carbon monoxide (1 atm) at 70° C. overnight. The reaction mixture was cooled to ambient temperature and 2,4-dimethoxybenzylamine (2.17 mg, 13.0 mmol) added. The mixture was stirred for 2 hours diluted with ethyl acetate (800 mL), and filtered through celite. The organic solution was washed twice with water (800 mL), brine (300 mL), and dried (MgSO$_4$). Filtration and removal of the solvent under reduced pressure gave crude material that was purified by silica chromatography (EtOAc(1):heptanes(1)) to give (2R,6R,11R)-tert-butyl 8-((2,4-dimethoxybenzyl)carbamoyl)-6,11-dimethyl-1,2,5,6-tetrahydro-2,6-methanobenzo[d]azocine-3(4H)-carboxylate (4.0 g, 68% yield); LC/MS (M+H)$^+$=495.3.

(2R,6R,11R)—N-(2,4-dimethoxybenzyl)-6,11-dimethyl-1,2,3,4,5,6-hexahydro-2,6-methanobenzo[d]azocine-8-carboxamide hydrochloride

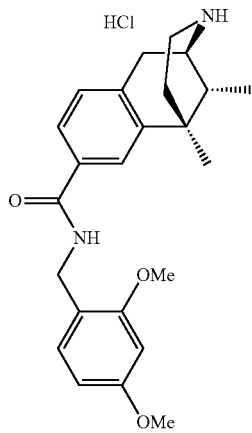

Chemical Formula: C$_{24}$H$_{31}$ClN$_2$O$_3$
Exact Mass: 430.20
Molecular Weight: 430.97

A mixture of (2R,6R,11R)-tert-butyl 8-((2,4-dimethoxybenzyl)carbamoyl)-6,11-dimethyl-1,2,5,6-tetrahydro-2,6-methanobenzo[d]azocine-3(4H)-carboxylate (4.00 g, 8.09 mmol) in 4N HCl/dioxane was stirred at ambient temperature overnight.

The majority of the solvent was decanted and the residue washed with diethyl ether (500 mL). The resulting solid was dried under reduced pressure giving (2R,6R,11R)—N-(2,4-dimethoxybenzyl)-6,11-dimethyl-1,2,3,4,5,6-hexahydro-2,6-methanobenzo[d]azocine-8-carboxamide hydrochloride (3.35 g, 96% yield); LC/MS (M+H)$^+$=395.5.

(2R,6R,11R)—N-(2,4-dimethoxybenzyl)-3-(2-methoxyethyl)-6,11-dimethyl-1,2,3,4,5,6-hexahydro-2,6-methanobenzo[d]azocine-8-carboxamide

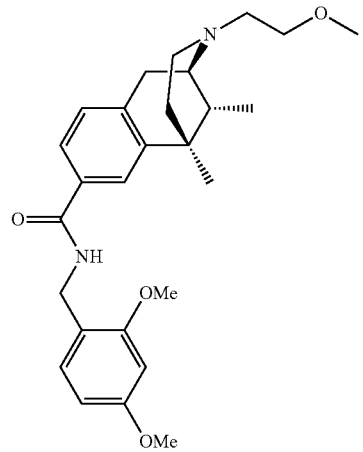

Chemical Formula: C$_{27}$H$_{36}$N$_2$O$_4$
Exact Mass: 452.27
Molecular Weight: 452.59

A mixture of 2R,6R,11R)—N-(2,4-dimethoxybenzyl)-6,11-dimethyl-1,2,3,4,5,6-hexahydro-2,6-methanobenzo[d]azocine-8-carboxamide hydrochloride (400 mg, 0.93 mmol), potassium carbonate (385 mg, 2.78 mmol), and bromoethyl methyl ether (142 mg, 1.02 mmol) in acetonitrile (15 mL) was heated at 65° C. overnight. Further bromoethyl methyl ether was added (70 mg, 0.50 mmol) and the reaction heated at 65° C. for 24 hours. The reaction mixture was allowed to return to ambient temperature before partitioning between ethyl acetate (100 mL) and water (100 mL). The organic phase was dried (MgSO$_4$). Filtration and removal of the solvent under reduced pressure gave (2R,6R,11R)—N-(2,4-dimethoxybenzyl)-3-(2-methoxyethyl)-6,11-dimethyl-1,2,3,4,5,6-hexahydro-2,6-methanobenzo[d]azocine-8-carboxamide (360 mg, 86% yield); LC/MS (M+H)$^+$=453.2.

(2R,6R,11R)-3-(2-methoxyethyl)-6,11-dimethyl-1,2,3,4,5,6-hexahydro-2,6-methanobenzo[d]azocine-8-carboxamide

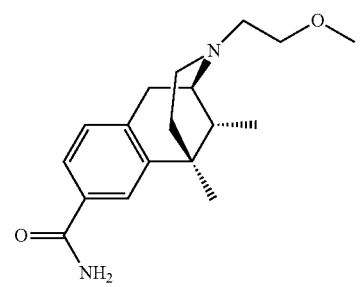

Chemical Formula: C$_{18}$H$_{26}$N$_2$O$_2$
Exact Mass: 302.20
Molecular Weight: 302.41

A mixture of (2R,6R,11R)—N-(2,4-dimethoxybenzyl)-3-(2-methoxyethyl)-6,11-dimethyl-1,2,3,4,5,6-hexahydro-2,6- methanobenzo[d]azocine-8-carboxamide (360 mg, 0.80 mmol) in trifluoroacetic acid (5 mL) was stirred at ambient temperature for 2 hours. The mixture was concentrated under reduced pressure before quenching with ice/ammonium hydroxide (28%) (25 mL). The crude product was extracted twice using dichloromethane (100 mL) and the combined organic layers dried (MgSO$_4$). Filtration and removal of the solvent under reduced pressure gave the crude product that was purified by prep-HPLC giving (2R,6R,11R)-3-(2-methoxyethyl)-6,11-dimethyl-1,2,3,4,5,6-hexahydro-2,6-methanobenzo[d]azocine-8-carboxamide (130 mg, 54% yield); LC/MS (M+H)$^+$=303.2.

2R,6R,11R)-3-(2-methoxyethyl)-6,11-dimethyl-1,2,3,4,5,6-hexahydro-2,6-methanobenzo[d]azocine-8-carboxamide hydrochloride (Compound 14)

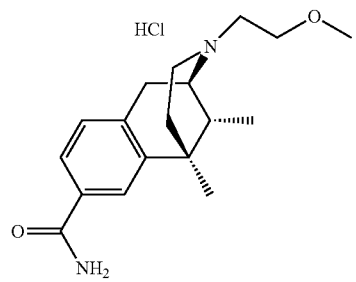

Chemical Formula: C$_{18}$H$_{27}$ClN$_2$O$_2$
Exact Mass: 338.18
Molecular Weight: 338.87

To a solution of (2R,6R,11R)-3-(2-methoxyethyl)-6,11-dimethyl-1,2,3,4,5,6-hexahydro-2,6-methanobenzo[d]azocine-8-carboxamide (130 mg, 0.43 mmol) in ethyl acetate (10 mL) was added 2N HCl/ether (320 µL, 0.64 mmol) and the mixture stirred for 1.5 hours. The solvent was removed under reduced pressure then freeze dried giving (2R,6R,11R)-3-(2-methoxyethyl)-6,11-dimethyl-1,2,3,4,5,6-hexahydro-2,6-methanobenzo[d]azocine-8-carboxamide hydrochloride (131 mg, 90% yield); LC/MS (M+H)$^+$=303.22.
$^1$H-NMR (300 MHz, DMSO) δ 10.59-10.44 (br d, 1H), 7.96 (s, 1H), 7.78 (s, 1H), 7.68 (d, 1H), 7.31 (d, 1H), 7.20 (d, 1H), 3.84-3.49 (m, 3H), 3.49-2.95 (6H+H$_2$O), 2.43-2.20 (m, 2H), 2.16-1.97 (m, 2H), 1.54-1.23 (m, 2H), 0.87-0.66 (m, 3H).

A5. Experimental Procedure for

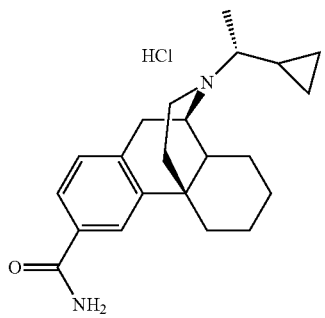

Chemical Formula: C$_{22}$H$_{31}$ClN$_2$O
Exact Mass: 374.21
Molecular Weight: 374.95

(4bS,9R)-4-hydroxy-3-methoxy-11-methyl-8,8a,9,10-tetrahydro-5H-9,4b-(epiminoethano)phenanthren-6(7H)-one (A) and (4bR,9R)-3-methoxy-11-methyl-6,7,8,8a,9,10-hexahydro-5H-9,4b-(epiminoethano)phenanthren-4-ol (B)

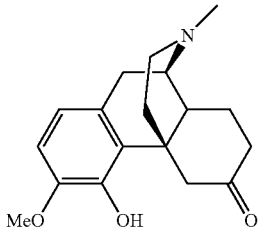

(A)

Chemical Formula: C$_{18}$H$_{23}$NO$_3$
Exact Mass: 301.17
Molecular Weight: 301.38

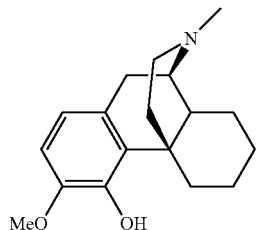

(B)

Chemical Formula: C$_{18}$H$_{25}$NO$_2$
Exact Mass: 287.19
Molecular Weight: 287.40

To a mixture of hydrocodone (2×22 g (2 batches), 147 mmol) and zinc powder (2×115 g, 3.46 mol) in acetic acid (2×1 L) was added conc. HCl (2×50 mL). The reaction was heated at 125° C. for 3 hours. Both reactions were combined and filtered. The zinc wash washed with industrial methylated spirits (1 L), and dichloromethane (1 L). Both organic washes and the acetic acid solution were concentrated under reduced pressure and the residue basified with ice/ammonium hydroxide (28%). The crude product was extracted into dichloromethane and dried (MgSO$_4$). Filtration and removal of the solvent under reduced pressure gave the crude products that were purified by silica chromatography (3% methanol/ammonia in dichloromethane) giving three batches of varying purity (2.4 g, (B); 20.5 g, 50% (A), 50% (B); 12.5 g, 65% (A), 10% (B)); LC/MS (M+H)$^+$=302.1 (A); LC/MS (M+H)$^+$=288.2 (B).

(4bS,9R)-3-methoxy-11-methyl-6-oxo-6,7,8,8a,9,10-hexahydro-5H-9,4b-(epiminoethano)phenanthren-4-yl trifluoromethanesulfonate (C) and (4bR,9R)-3-methoxy-11-methyl-6,7,8,8a,9,10-hexahydro-5H-9,4b-(epiminoethano)phenanthren-4-yl trifluoromethanesulfonate (D)

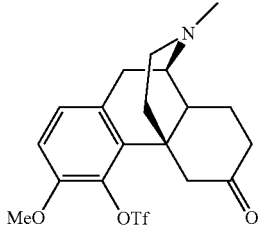

(C)

Chemical Formula: C$_{19}$H$_{22}$F$_3$NO$_5$S
Exact Mass: 433.12
Molecular Weight: 433.44

-continued

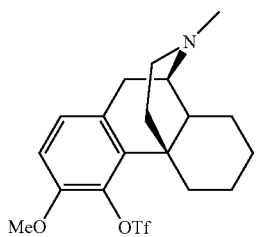

(D)

Chemical Formula: C₁₉H₂₄F₃NO₄S
Exact Mass: 419.14
Molecular Weight: 419.46

To a solution containing a (1:1) mixture of (4bS,9R)-4-hydroxy-3-methoxy-11-methyl-8,8a,9,10-tetrahydro-5H-9,4b-(epiminoethano)phenanthren-6(7H)-one (A) and (4bR,9R)-3-methoxy-11-methyl-6,7,8,8a,9,10-hexahydro-5H-9,4b-(epiminoethano)phenanthren-4-ol (B) (20.5 g, 69.4 mmol) in tetrahydrofuran at 0° C. under an argon atmosphere was added sodium hydride (4.18 g, 60% in mineral oil, 104.5 mmol). After 30 minutes N-Phenylbis(trifluoromethanesulfonamide) (37.3 g, 104.4 mmol) was added and the mixture allowed to slowly return to ambient temperature. The reaction was quenched with saturated aqueous sodium bicarbonate solution (500 mL) and extracted into ethyl acetate (1 L). The organic phase was washed with brine and dried (MgSO₄). Filtration and removal of the solvent under reduced pressure gave the crude product that was purified by silica chromatography (2.5% methanol/ammonia in dichloromethane) giving two batches of varying purity (11.0 g, (D); 15.1 g, 62% (C), 33% (D); LC/MS (M+H)⁺=434.1 (C); LC/MS (M+H)⁺=420.1 (D).

(4bR,9R)-3-methoxy-11-methyl-6,7,8,8a,9,10-hexahydro-5H-9,4b-(epiminoethano)phenanthrene

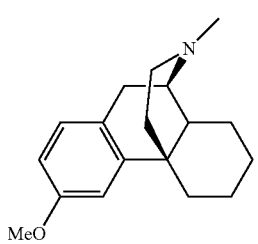

Chemical Formula: C₁₈H₂₅NO
Exact Mass: 271.19
Molecular Weight: 271.40

A mixture of (4bR,9R)-3-methoxy-11-methyl-6,7,8,8a,9,10-hexahydro-5H-9,4b-(epiminoethano)phenanthren-4-yl trifluoromethanesulfonate (D) (11.0 g, 26.2 mmol), palladium acetate (590 mg, 2.63 mmol), 1,3-bis(diphenylphosphino)propane (1.08 g, 2.61 mmol) and triethylsilane (10.0 mL, 62.6 mmol) in dimethylformamide (degassed) was heated at 60° C. overnight under an argon atmosphere. The reaction mixture was cooled to ambient temperature and partitioned between ethyl acetate (1 L) and water (1 L). The organic phase was washed twice more with water (2×500 mL). The combined aqueous phases were extracted using dichloromethane (2 L total). The organic phase containing dichloromethane and dimethyl formamide was concentrated under reduced pressure and the crude product purified by silica chromatography (3% methanol/ammonia in dichloromethane).

The same procedure was carried out with the 15.1 g batch (62% (C), 33% (D)). The material was purified as described above to give (4bR,9R)-3-methoxy-11-methyl-6,7,8,8a,9,10-hexahydro-5H-9,4b-(epiminoethano)phenanthrene (8.6 g); LC/MS (M+H)⁺=272.0.

(4bR,9R)-3-methoxy-6,7,8,8a,9,10-hexahydro-5H-9,4b-(epiminoethano)phenanthrene

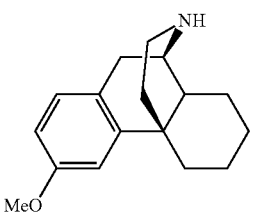

Chemical Formula: C₁₇H₂₃NO
Exact Mass: 257.18
Molecular Weight: 257.37

To a solution of (4bR,9R)-3-methoxy-11-methyl-6,7,8,8a,9,10-hexahydro-5H-9,4b-(epiminoethano)phenanthrene (5.0 g, 18.44 mmol) in dichloromethane (400 mL) was added a solution of CNBr (17 mL, 51 mmol, 3N in dichloromethane) under an argon atmosphere. The mixture was heated at reflux overnight. The solvent was removed under reduced pressure and to the residue was added diethyleneglycol (100 mL) and KOH (16.6 g, 296 mmol). The reaction mixture was heated at 160° C. for 2 hours, allowed to return to ambient temperature, then partitioned between dichloromethane (600 mL) and water (1 L). The aqueous phase was washed twice more with dichloromethane and the combined organic fractions dried (MgSO₄). Filtration and removal of the solvent under reduced pressure gave the crude product that was purified by silica chromatography (10% methanol/ammonia in DCM) giving (4bR,9R)-3-methoxy-6,7,8,8a,9,10-hexahydro-5H-9,4b-(epiminoethano)phenanthrene (4.02 g, 85% yield); LC/MS (M+H)⁺=258.5.

(4bR,9R)-11-(1-cyclopropylethyl)-3-methoxy-6,7,8,8a,9,10-hexahydro-5H-9,4b-(epiminoethano)phenanthrene

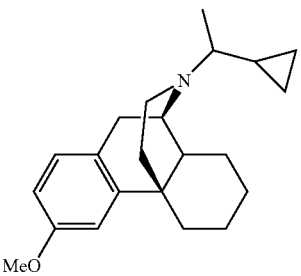

Chemical Formula: C₂₂H₃₁NO
Exact Mass: 325.24
Molecular Weight: 325.49

A mixture of (4bR,9R)-3-methoxy-6,7,8,8a,9,10-hexahydro-5H-9,4b-(epiminoethano)phenanthrene (1.41 g), methylcyclopropyl ketone (17 mL, 172 mmol), and acetic acid were heated at 70° C. for 1 hour. Sodium cyanoborohydride was added (830 mg, 13.2 mmol) and the mixture heated at 70° C. overnight. The reaction mixture was portioned between ethyl acetate (500 mL) and saturated sodium bicarbonate (500 mL). The organic phase was washed with brine and dried (MgSO$_4$). Filtration and removal of the solvent under reduced pressure gave the crude product that was purified by silica chromatography (2% methanol/ammonia in dichloromethane) giving (4bR,9R)-11-(1-cyclopropylethyl)-3-methoxy-6,7,8,8a,9,10-hexahydro-5H-9,4b-(epiminoethano)phenanthrene (0.75 g, 42% yield); LC/MS (M+H)$^+$=326.1.

(4bR,9R)-11-(1-cyclopropylethyl)-6,7,8,8a,9,10-hexahydro-5H-9,4b-(epiminoethano)phenanthren-3-ol

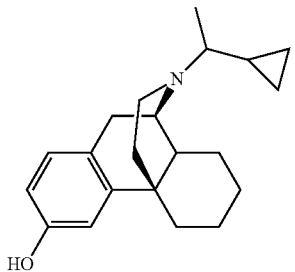

Chemical Formula: C$_{21}$H$_{29}$NO
Exact Mass: 311.22
Molecular Weight: 311.46

To an ice cooled solution of (4bR,9R)-11-(1-cyclopropylethyl)-3-methoxy-6,7,8,8a,9,10-hexahydro-5H-9,4b-(epiminoethano)phenanthrene (0.75 g, 2.31 mmol) in dichloromethane (50 mL) was added BBr$_3$ (0.9 mL, 9.23 mmol) dropwise under an argon atmosphere. The reaction was stirred for 3 hours then quenched with ammonia/methanol. The solvent was removed under reduced pressure giving (4bR,9R)-11-(1-cyclopropylethyl)-6,7,8,8a,9,10-hexahydro-5H-9,4b-(epiminoethano)phenanthren-3-ol (0.75 g, 100% yield); LC/MS (M+H)$^+$=312.1.

(4bR,9R)-11-(1-cyclopropylethyl)-6,7,8,8a,9,10-hexahydro-5H-9,4b-(epiminoethano)phenanthren-3-yl trifluoromethanesulfonate

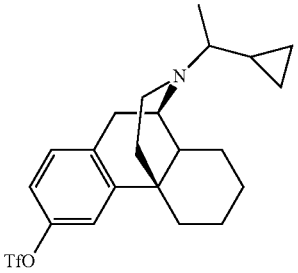

Chemical Formula: C$_{22}$H$_{28}$F$_3$NO$_3$S
Exact Mass: 443.17
Molecular Weight: 443.52

To a solution of (4bR,9R)-11-(1-cyclopropylethyl)-6,7,8,8a,9,10-hexahydro-5H-9,4b-(epiminoethano)phenanthren-3-ol (0.75 g, 2.41 mmol) and triethylamine (1.0 mL, 7.23 mmol) in dichloromethane (50 mL) was added N-Phenylbis(trifluoromethanesulfonamide) (0.95 g, 2.65 mmol) and the mixture stirred at room temperature overnight. The solvent was concentrated under reduced pressure and the residue partitioned between 20% hexane in ethyl acetate (300 mL) and water (150 mL). The organic layer was washed four more times more with water and dried (MgSO$_4$). Filtration and removal of the solvent under reduced pressure gave (4bR,9R)-11-(1-cyclopropylethyl)-6,7,8,8a,9,10-hexahydro-5H-9,4b-(epiminoethano)phenanthren-3-yl trifluoromethanesulfonate (0.78 g, 73% yield); LC/MS (M+H)$^+$=444.1.

(4bR,9R)-11-(1-cyclopropylethyl)-N-(2,4-dimethoxybenzyl)-6,7,8,8a,9,10-hexahydro-5H-9,4b-(epiminoethano)phenanthrene-3-carboxamide

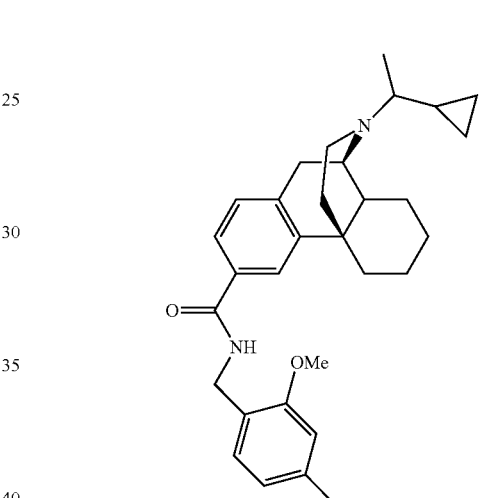

Chemical Formula: C$_{31}$H$_{40}$N$_2$O$_3$
Exact Mass: 488.30
Molecular Weight: 488.66

To a solution of (4bR,9R)-11-(1-cyclopropylethyl)-6,7,8,8a,9,10-hexahydro-5H-9,4b-(epiminoethano)phenanthren-3-yl trifluoromethanesulfonate (0.78 g, 1.76 mmol) in degassed dimethyl sulfoxide (15 mL), was added N-hydroxysuccinimide (405 mg, 3.52 mmol), palladium acetate (79 mg, 0.352 mmol), triethylamine (490 μL, 3.52 mmol) and 4,5-bis(diphenylphosphino)-9,9-dimethylxanthene (203 mg, 0.352 mmol). The reaction mixture was heated with carbon monoxide (1 atm) at 75° C. overnight. The reaction mixture was cooled to ambient temperature and 2,4-dimethoxybenzylamine (294 mg, 1.76 mmol) added. The mixture was stirred for 1 hour before partitioning between water (300 mL) and ethyl acetate (400 mL). The aqueous phase was extracted twice more with ethyl acetate. The combined organic phase was dried (MgSO$_4$), filtered, and the solvent removed under reduced pressure. The crude material was purified by silica chromatography (3% methanol in dichloromethane) to give (4bR,9R)-11-(1-cyclopropylethyl)-N-(2,4-dimethoxybenzyl)-6,7,8,8a,9,10-hexahydro-5H-9,4b-(epiminoethano)phenanthrene-3-carboxamide (1.0 g, contains impurities—used directly in next step); LC/MS (M+H)$^+$=489.1.

(4bR,9R)-11-((R)-1-cyclopropylethyl)-6,7,8,8a,9,10-hexahydro-5H-9,4b-(epiminoethano)phenanthrene-3-carboxamide

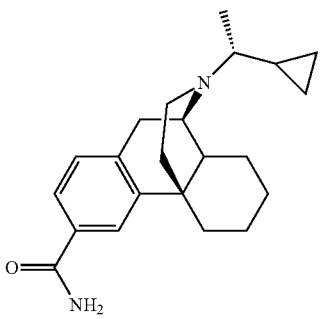

Chemical Formula: $C_{22}H_{30}N_2O$
Exact Mass: 338.24
Molecular Weight: 338.49

A mixture of (4bR,9R)-11-(1-cyclopropylethyl)-N-(2,4-dimethoxybenzyl)-6,7,8,8a,9,10-hexahydro-5H-9,4b-(epiminoethano)phenanthrene-3-carboxamide (1.0 g, 2.05 mmol) in trifluoroacetic acid (30 mL) was stirred at room temperature for 2 hours. The mixture was concentrated under reduced pressure before quenching with ice/ammonium hydroxide (28%) (50 mL). The crude product was extracted twice using dichloromethane (200 mL) and the combined organic layers dried (MgSO$_4$). Filtration and removal of the solvent under reduced pressure gave the crude product that was purified and separated from the (S)-diastereomer using prep-HPLC giving (4bR,9R)-11-((R)-1-cyclopropylethyl)-6,7,8,8a,9,10-hexahydro-5H-9,4b-(epiminoethano)phenanthrene-3-carboxamide (64 mg, 10% yield); LC/MS (M+H)$^+$=339.3.

(4bR,9R)-11-((R)-1-cyclopropylethyl)-6,7,8,8a,9,10-hexahydro-5H-9,4b-(epiminoethano)phenanthrene-3-carboxamide hydrochloride

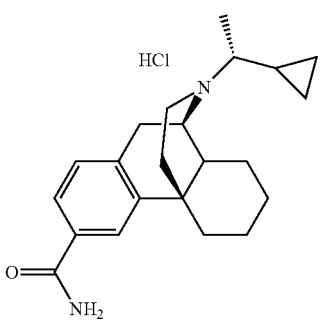

Chemical Formula: $C_{22}H_{31}ClN_2O$
Exact Mass: 374.21
Molecular Weight: 374.95

To a solution of (4bR,9R)-11-((R)-1-cyclopropylethyl)-6,7,8,8a,9,10-hexahydro-5H-9,4b-(epiminoethano)phenanthrene-3-carboxamide (64 mg, 0.19 mmol) in ethyl acetate (15 mL) was added 2N HCl/ether (140 μL, 0.28 mmol) and the mixture stirred for 30 minutes. The solvent was removed under reduced pressure then freeze dried giving (4bR,9R)-11-((R)-1-cyclopropylethyl)-6,7,8,8a,9,10-hexahydro-5H-9,4b-(epiminoethano)phenanthrene-3-carboxamide hydrochloride (71 mg, 100% yield); LC/MS (M+H)$^+$=339.3.
$^1$H-NMR (400 MHz, DMSO) δ 10.41 (br s, 1H), 7.95 (s, 1H), 7.81 (s, 1H), 7.68 (d, 1H), 7.30 (s, 1H), 7.22 (d, 1H), 4.18 (s, 1H), 3.57-3.03 (m, 3H+H$_2$O), 2.95 (d, 1H), 2.55 (d, 1H), 2.37-2.16 (m, 2H), 2.08-1.87 (m, 1H), 2.68-0.51 (m, 15H), 0.20 (s, 1H).

A6. Experimental Procedure for Compound E and a Hydrochloride Salt Thereof

Synthesis of (4R,4aR,7aR,12bS)-3-(cyclobutylmethyl)-1,2,3,4,4a,5,6,7a-octahydrospiro[4,12-methanobenzofuro[3,2-e]isoquinoline-7,2'-[1,3]dioxolane]-9-carbonitrile

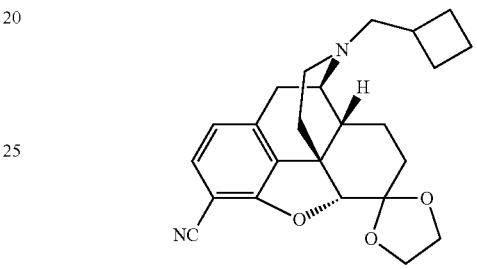

To a solution of cyclobutane carboxaldehyde (19.45 g, 231.2 mmol) in dichloromethane (500 mL) was added (4R,4aR,7aR,12bS)-1,2,3,4,4a,5,6,7a-octahydrospiro[4,12-methanobenzofuro[3,2-e]isoquinoline-7,2'-[1,3]dioxolane]-9-carbonitrile (25 g, 77.1 mmol). The reaction was stirred for 60 minutes at room temperature before sodium triacetoxyborohydride (32.7 g, 154.0 mmol) was added portionwise over 20 minutes. After one hour, the reaction was quenched with NaHCO$_3$ solution and extracted with dichloromethane (×3). The dichloromethane phases were combined, washed with brine, dried over MgSO$_4$ and concentrated under reduced pressure. The residue was purified by silica chromatography eluted with dichloromethane to 7% methanol in dichloromethane to give (4R,4aR,7aR,12bS)-3-(cyclobutylmethyl)-1,2,3,4,4a,5,6,7a-octahydrospiro[4,12-methanobenzofuro[3,2-e]isoquinoline-7,2'-[1,3]dioxolane]-9-carbonitrile (31.1 g, 98% pure LCMS, assume quant.); [M+H]$^+$ 393.1.

Synthesis of (4R,4aR,7aR,12bS)-3-(cyclobutylmethyl)-7-oxo-2,3,4,4a,5,6,7,7a-octahydro-1H-4,12-methanobenzofuro[3,2-e]isoquinoline-9-carbonitrile

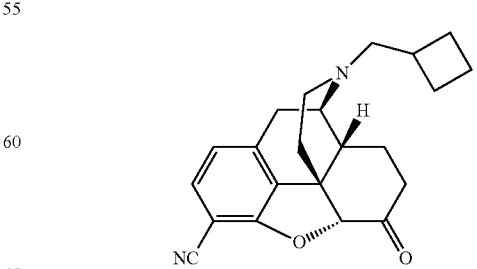

A suspension of (4R,4aR,7aR,12bS)-3-(cyclobutylmethyl)-1,2,3,4,4a,5,6,7a-octahydrospiro[4,12-methanobenzofuro[3,2-e]isoquinoline-7,2'-[1,3]dioxolane]-9-carbonitrile (31.1 g, 79.2 mmol) in 6M HCl (aq) (250 mL) was stirred at room temperature for 24 hours. Further 6M HCl was added (25 mL) and stirred for an additional 24 hours. The reaction was poured onto ice/NH$_3$ $_{(aq)}$ and stirred for 30 minutes and the solid collected by suction filtration and washed with water. The solid was dissolved in dichloromethane and washed with brine, dried over MgSO$_4$ and concentrated under reduced pressure to give (4R,4aR,7aR,12bS)-3-(cyclobutylmethyl)-7-oxo-2,3,4,4a,5,6,7,7a-octahydro-1H-4,12-methanobenzofuro[3,2-e]isoquinoline-9-carbonitrile (26.1 g, 96% pure LCMS, 95% yield); [M+H]$^+$ 367.2.

Synthesis of (4R,4aR,7aR,12bS)-3-(cyclobutylmethyl)-7-oxo-2,3,4,4a,5,6,7,7a-octahydro-1H-4,12-methanobenzofuro[3,2-e]isoquinoline-9-carboxamide

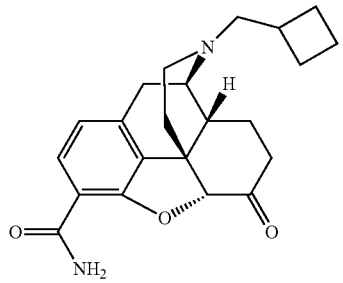 [SMILES: NC(=O)c1ccc2c3c1O[C@H]1C(=O)CC[C@H]4[C@@H](C2)N(CC2CCC2)CC[C@]314]

To a solution of (4R,4aR,7aR,12bS)-3-(cyclobutylmethyl)-7-oxo-2,3,4,4a,5,6,7,7a-octahydro-1H-4,12-methanobenzofuro[3,2-e]isoquinoline-9-carbonitrile (24 g, 68.9 mmol) in tert-butanol (240 mL) was added KOH (2.1 g, 37.1 mmol). The reaction was heated to 100° C. for 15 minutes. The reaction was allowed to cool to room temperature and concentrated to 50% volume. Diluted with water and extracted with ethyl acetate twice. The organic phases were combined, washed with sodium hydrogen carbonate solution and brine and dried over MgSO$_4$ and concentrated under reduced pressure. The residue was purified by silica chromatography eluted with 4% methanol in dichloromethane to give to give (4R,4aR,7aR,12bS)-3-(cyclobutylmethyl)-7-oxo-2,3,4,4a,5,6,7,7a-octahydro-1H-4,12-methanobenzofuro[3,2-e]isoquinoline-9-carboxamide (14.2 g, 89% pure LCMS, 56% yield); [M+H]$^+$ 367.2.

Synthesis of (4bS,8aR,9R)-11-(cyclobutylmethyl)-4-hydroxy-6-oxo-6,7,8,8a,9,10-hexahydro-5H-9,4b-(epiminoethano)phenanthrene-3-carboxamide (Compound E)

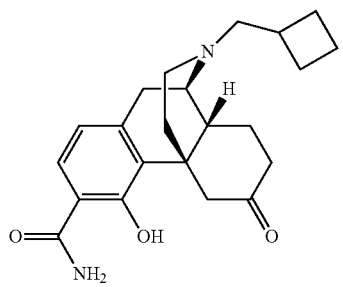 [SMILES: NC(=O)c1ccc2c(c1O)[C@]13CCN(CC4CCC4)[C@H](C2)[C@@H]1CCC(=O)C3]

To a solution of (4R,4aR,7aR,12bS)-3-(cyclobutylmethyl)-7-oxo-2,3,4,4a,5,6,7,7a-octahydro-1H-4,12-methanobenzofuro[3,2-e]isoquinoline-9-carboxamide (14.2 g, 38.75 mmol) in ethanol (500 mL) was added ammonium chloride (31.1 g, 581 mmol) followed by zinc powder (25.3 g, 388 mmol). The reaction was heated to reflux for 2.5 hours. The reaction was cooled to ~50° C. and filtered through a pad of celite. The celite was washed with ethanol/methanol. The filtrate was concentrated under reduced pressure. The residue was partitioned between dichloromethane and NH$_{3(aq)}$/H$_2$O (1:1) and the aqueous phase re-extracted with dichloromethane. The combined dichloromethane phase was washed with brine, dried over MgSO$_4$ and concentrated. The crude product was purified by silica chromatography and eluted with 3.5% NH$_3$/methanol in dichloromethane to give (4bS,8aR,9R)-11-(cyclobutylmethyl)-4-hydroxy-6-oxo-6,7,8,8a,9,10-hexahydro-5H-9,4b-(epiminoethano)phenanthrene-3-carboxamide (9.7 g, 98.5% pure LCMS, 68% yield); [M+H]$^+$ 369.2.

Synthesis of (4bS,6S,8aR,9R)-11-(cyclobutylmethyl)-4,6-dihydroxy-6,7,8,8a,9,10-hexahydro-5H-9,4b-(epiminoethano)phenanthrene-3-carboxamide hydrochloride

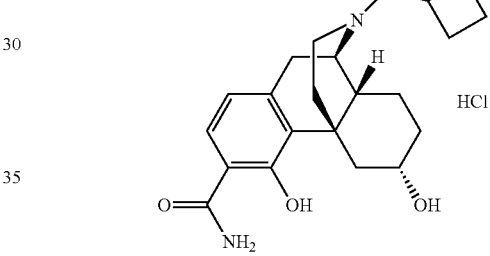

1M K-selectride in tetrahydrofuran (49.9 mL) was added to a solution of (4bS,8aR,9R)-11-(cyclobutylmethyl)-4-hydroxy-6-oxo-6,7,8,8a,9,10-hexahydro-5H-9,4b-(epiminoethano)phenanthrene-3-carboxamide (9.2 g, 25.0 mmol) in tetrahydrofuran (150 mL) cooled in an ice bath. After 30 minutes a saturated solution of ammonium chloride was added and the reaction mixture extracted with ethyl acetate (×3). The combined organic phase was washed with sodium hydrogen carbonate solution and brine, dried over MgSO$_4$ and concentrated. The residue was taken up in 2M HCl aq and washed with ethyl acetate. The aqueous phase was basified with 2 M NaOH to pH 7 then sodium hydrogen carbonate solution was added. The aqueous solution was extracted with dichloromethane (×3) dried over MgSO$_4$, concentrated, and purified via prep HPLC (30-50% acetonitrile in 0.1% NH$_4$HCO$_3$ pH10 buffer) to give (4bS,8aR,9R)-11-(cyclobutylmethyl)-4-hydroxy-6-oxo-6,7,8,8a,9,10-hexahydro-5H-9,4b-(epiminoethano)phenanthrene-3-carboxamide (4.7 g, 99.76% pure LCMS, 51% yield); [M+H]$^+$ 371.19.

To a solution of (4bS,8aR,9R)-11-(cyclobutylmethyl)-4-hydroxy-6-oxo-6,7,8,8a,9,10-hexahydro-5H-9,4b-(epiminoethano)phenanthrene-3-carboxamide (4.6 g, 12.4 mmol) in ethyl acetate (30 mL) and dichloromethane (30 mL) was added 2M HCl in diethyl ether (7.45 mL, 14.9 mmol). After 2 hours, the liquors were removed under reduced pressure and the residue suspended in diethyl ether, collected by suction filtration and washed with diethyl ether. The solid was dissolved in 9:1 water/methanol and freeze dried to give (4bS,6S,8aR,9R)-11-(cyclobutylmethyl)-4,6-dihydroxy-6,7,8,8a,9,10-hexahydro-5H-9,4b-(epiminoethano)phenanthrene-3-carboxamide hydrochloride (4.7 g, 99.81% pure LCMS, 93% yield); [M+H]$^+$ 371.19. $^1$H NMR (300 MHz, D$_2$O) 7.37 (1H, d), 6.62 (1H, d), 3.99 (1H, br s), 3.66 (1H, br d), 3.51 (1H, br s), 2.91-3.27 (5H, m), 2.44-2.62 (2H, m), 1.23-2.05 (14H, m).

A7. Experimental Procedure for Compound B and a Hydrochloride Salt Thereof

Synthesis of (4bS,8aR,9R)-11-(cyclopropylmethyl)-5,7,8,8a,9,10-hexahydrospiro[9,4b-(epiminoethano)phenanthrene-6,2'-[1,3]dioxolane]-3-carbonitrile

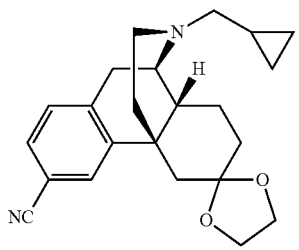

To a solution of (4bS,8aR,9R)-5,7,8,8a,9,10-hexahydrospiro[9,4b-(epiminoethano)phenanthrene-6,2'-[1,3]dioxolane]-3-carbonitrile (3.58 g, 11.5 mmol) in dichloromethane (115 mL) was added cyclopropylcarboxaldehyde (2.55 mL, 34.6 mmol). The reaction was stirred for 60 minutes at room temperature before sodium triacetoxyborohydride (4.90 g, 23.1 mmol) was added portionwise. After one hour, the reaction was quenched with aqueous NaHCO$_3$ solution and extracted with dichloromethane (×3). The dichloromethane phases were combined, washed with brine, dried over MgSO$_4$ and concentrated under reduced pressure. The residue was purified by silica chromatography eluted with dichloromethane to 5% methanol in dichloromethane to give (4bS,8aR,9R)-11-(cyclopropylmethyl)-5,7,8,8a,9,10-hexahydrospiro[9,4b-(epiminoethano)phenanthrene-6,2'-[1,3]dioxolane]-3-carbonitrile (3.59 g, 98.5% pure LCMS, 86% yield); [M+H]$^+$ 365.2.

Synthesis of (4bS,8aR,9R)-11-(cyclopropylmethyl)-5,7,8,8a,9,10-hexahydrospiro[9,4b-(epiminoethano)phenanthrene-6,2'-[1,3]dioxolane]-3-carboxamide

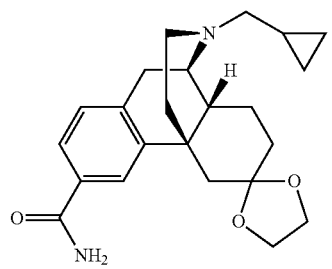

To a solution of (4bS,8aR,9R)-11-(cyclopropylmethyl)-5,7,8,8a,9,10-hexahydrospiro[9,4b-(epiminoethano)phenanthrene-6,2'-[1,3]dioxolane]-3-carbonitrile (3.95 g, 9.9 mmol) in dimethylsulfoxide (40 mL) was added potassium carbonate (4.09 g, 29.6 mmol). The reaction was cooled to 15° C. and hydrogen peroxide (12 mL, 35% aqueous solution) added dropwise maintaining the temperature between 15 and 20° C. After addition was complete, the reaction was allowed to warm to room temperature. The reaction was cooled to 0° C., quenched with water and extracted with ethyl acetate. The reaction was basified with sodium hydrogen carbonate solution to pH 10 and extracted with ethyl acetate (×3). The organics were combined, washed with water (×3), brine, dried over MgSO$_4$ and concentrated under reduced pressure. The product was purified by silica chromatography eluted with a gradient from 100% dichloromethane to 10% NH$_3$/methanol in dichloromethane to give (4bS,8aR,9R)-11-(cyclopropylmethyl)-5,7,8,8a,9,10-hexahydrospiro[9,4b-(epiminoethano)phenanthrene-6,2'-[1,3]dioxolane]-3-carboxamide (2.76 g, 98.3% pure LCMS, 73% yield); [M+H]$^+$ 383.2.

Synthesis of (4bS,8aR,9R)-11-(cyclopropylmethyl)-6-oxo-6,7,8,8a,9,10-hexahydro-5H-9,4b-(epiminoethano)phenanthrene-3-carboxamide hydrochloride

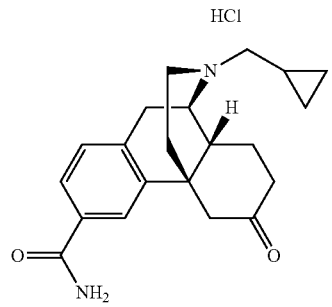

To (4bS,8aR,9R)-11-(cyclopropylmethyl)-5,7,8,8a,9,10-hexahydrospiro[9,4b-(epiminoethano)phenanthrene-6,2'-[1,3]dioxolane]-3-carboxamide (2.76 g, 7.2 mmol) was added 6M HCl (aq) (60 mL) with cooling. After an hour the reaction was poured onto ice/NH$_{3(aq)}$ and extracted with dichloromethane (×3). The dichloromethane phases were combined, washed with brine, dried over MgSO$_4$ and concentrated under reduced pressure. The residue was purified by silica chromatography eluted with 100% dichloromethane to 10% NH$_3$/methanol in dichloromethane to give Compound B: (4bS,8aR,9R)-11-(cyclopropylmethyl)-6-oxo-6,7,8,8a,9,10-hexahydro-5H-9,4b-(epiminoethano)phenanthrene-3-carboxamide (2.41 g, 97.5% pure LCMS, 96% yield).

To (4bS,8aR,9R)-11-(cyclopropylmethyl)-6-oxo-6,7,8,8a,9,10-hexahydro-5H-9,4b-(epiminoethano)phenanthrene-3-carboxamide (2.39 g, 7.1 mmol) in ethyl acetate (60 mL) was added 2M HCl in diethyl ether (3.87 mL, 7.8 mmol). The product precipitated from solution and was collected by filtration. The solid was washed with ethyl acetate and diethyl ether before drying under vacuum. The product was dissolved in water and freeze dried to give (4bS,8aR,9R)-11-(cyclopropylmethyl)-6-oxo-6,7,8,8a,9,10-hexahydro-5H-9,4b-(epiminoethano)phenanthrene-3-carboxamide hydrochloride (2.62 g, 99.9% LCMS, 99% yield); [M+H]$^+$ 339.3. $^1$H NMR (300 MHz, D$_2$O) 7.60 (1H, s), 7.43 (1H, d), 7.17 (1H, d), 4.07 (0.8H, d), 3.97 (0.2H, d), 2.34-3.44 (10H, m), 1.74-2.18 (3H, m), 1.60 (0.8H, d), 1.44 (0.2H, d), 1.27 (1H, dq), 0.96 (1H, m), 0.59 (2H, d), 0.25 (2H, m).

A8. Experimental Procedure for

Synthesis of (4bS,8aR,9R)-11-(cyclobutylmethyl)-5,7,8,8a,9,10-hexahydrospiro[9,4b-(epiminoethano)phenanthrene-6,2'-[1,3]dioxolane]-3-carbonitrile

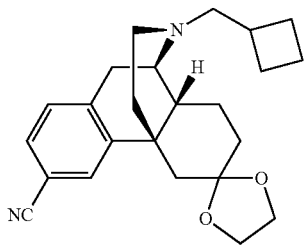

To a solution of cyclobutylmethanol (3.70 g, 42.9 mmol) in dichloromethane (100 mL) was added silica (25 g), followed by pyridinium chlorochromate (18.52 g, 85.9 mmol). The reaction mixture was stirred for 2 h and filtered through a plug of silica eluting with dichloromethane (300 mL). The resulting solution was concentrated to about 75 mL and (4bS,8aR,9R)-5,7,8,8a,9,10-hexahydrospiro[9,4b-(epiminoethano)phenanthrene-6,2'-[1,3]dioxolane]-3-carbonitrile (0.40 g, 0.13 mmol) added, followed by sodium triacetoxyborohydride (0.71 g, 0.34 mmol). The reaction mixture was stirred for 2 h, washed with aqueous sat. NaHCO$_3$ (100 mL) and dried over MgSO$_4$. After filtration and evaporation the residue was further purified by silica column chromatography eluting with 5-10% methanol/dichloromethane to give the desired product (4bS,8aR,9R)-11-(cyclobutylmethyl)-5,7,8,8a,9,10-hexahydrospiro[9,4b-(epiminoethano)phenanthrene-6,2'-[1,3]dioxolane]-3-carbonitrile as a yellow oil (0.48 g, 56% pure LCMS); [M+H]$^+$ 379.3. This was used in the next reaction without further purification.

Synthesis of (4bS,8aR,9R)-11-(cyclobutylmethyl)-5,7,8,8a,9,10-hexahydrospiro[9,4b-(epiminoethano)phenanthrene-6,2'-[1,3]dioxolane]-3-carboxamide

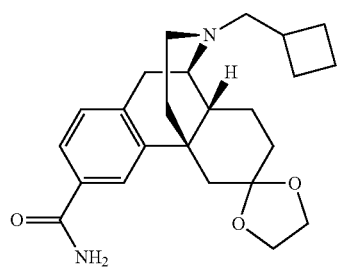

To (4bS,8aR,9R)-11-(cyclobutylmethyl)-5,7,8,8a,9,10-hexahydrospiro[9,4b-(epiminoethano)phenanthrene-6,2'-[1,3]dioxolane]-3-carbonitrile (0.48 g, 1.3 mmol) in dimethylsulfoxide (12 mL) was added potassium carbonate (0.53 g, 3.8 mmol). The reaction was cooled to 15° C. and hydrogen peroxide (2.0 mL, 35% aqueous solution) added dropwise maintaining the temperature between 15 and 20° C. After addition was complete, the reaction was allowed to warm to room temperature. The reaction was cooled to 0° C., quenched with water and extracted with ethyl acetate. The reaction was basified with sodium hydrogen carbonate solution and extracted with ethyl acetate (×3). The organics were combined, washed with water (×3), brine, dried over MgSO$_4$ and concentrated under reduced pressure. The product was purified by silica chromatography eluted with a gradient from 10% methanol in dichloromethane to 5% NH$_3$/methanol in dichloromethane to give (4bS,8aR,9R)-11-(cyclobutylmethyl)-5,7,8,8a,9,10-hexahydrospiro[9,4b-(epiminoethano)phenanthrene-6,2'-[1,3]dioxolane]-3-carboxamide (0.27 g, 94% pure LCMS, 54% yield over two steps); [M+H]$^+$ 397.3.

Synthesis of (4bS,8aR,9R)-11-(cyclobutylmethyl)-6-oxo-6,7,8,8a,9,10-hexahydro-5H-9,4b-(epiminoethano)phenanthrene-3-carboxamide hydrochloride

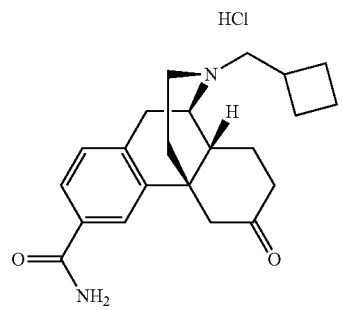

To (4bS,8aR,9R)-11-(cyclobutylmethyl)-5,7,8,8a,9,10-hexahydrospiro[9,4b-(epiminoethano)phenanthrene-6,2'-[1,3]dioxolane]-3-carboxamide (274 mg, 0.69 mmol) was added 6M HCl (aq) (12 mL). The reaction was stirred for 24 hours until complete. The reaction was poured onto ice/NH$_{3(aq)}$ and extracted with dichloromethane (×3). The dichloromethane phases were combined, washed with brine, dried over MgSO$_4$ and concentrated under reduced pressure. The residue was purified by silica chromatography eluted with 5-10% NH$_3$/methanol in dichloromethane to give (4bS,8aR,9R)-11-(cyclobutylmethyl)-6-oxo-6,7,8,8a,9,10-hexahydro-5H-9,4b-(epiminoethano)phenanthrene-3-carboxamide (225 mg, 99.2% pure LCMS, 93% yield).

To (4bS,8aR,9R)-11-(cyclobutylmethyl)-6-oxo-6,7,8,8a,9,10-hexahydro-5H-9,4b-(epiminoethano)phenanthrene-3-carboxamide (225 mg, 0.64 mmol) in ethyl acetate (10 mL) was added 2M HCl in diethyl ether (0.35 mL, 0.70 mmol). The product precipitated from solution and the liquors were concentrated under vacuum. The solid was triturated with diethyl ether before drying under vacuum. The product was dissolved in water and freeze dried to give (4bS,8aR,9R)-11-(cyclobutylmethyl)-6-oxo-6,7,8,8a,9,10-hexahydro-5H-9,4b-(epiminoethano)phenanthrene-3-carboxamide hydrochloride (237 mg, 99.3% LCMS, 89% yield); [M+H]$^+$ 353.2. $^1$H NMR (300 MHz, D$_2$O) 7.69 (1H, s), 7.59 (1H, dd), 7.29 (1H, d), 3.84 (1H, s), 2.48-3.55 (11H, m), 1.31-2.31 (11H, m).

A9. Experimental Procedure for

Synthesis of (4bS,6S,8aR,9R)-11-(cyclobutylmethyl)-6-hydroxy-6,7,8,8a,9,10-hexahydro-5H-9,4b-(epiminoethano)phenanthrene-3-carboxamide hydrochloride

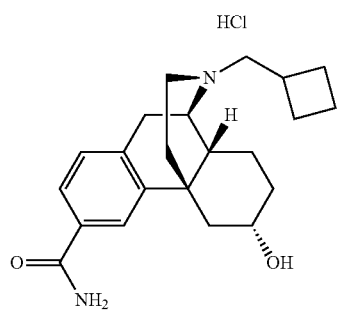

To a solution of (4bS,8aR,9R)-11-(cyclobutylmethyl)-6-oxo-6,7,8,8a,9,10-hexahydro-5H-9,4b-(epiminoethano)phenanthrene-3-carboxamide (84 mg, 0.24 mmol) in methanol (4 mL) was added sodium borohydride (18 mg, 0.48 mmol) at room temperature. The reaction was stirred for an hour before quenching with ammonium chloride solution. The aqueous phase was basified with 2M NaOH solution and extracted with dichloromethane (×4). The dichloromethane phases were combined, washed with brine, dried over MgSO$_4$ and concentrated under reduced pressure. The residue was purified by silica chromatography eluted with 10% NH$_3$/methanol in dichloromethane to separate the diastereoisomers. The major diastereoisomer was the desired (4bS,6S,8aR,9R)-11-(cyclobutylmethyl)-6-hydroxy-6,7,8,8a,9,10-hexahydro-5H-9,4b-(epiminoethano)phenanthrene-3-carboxamide (50 mg, 98.1% pure LCMS, 59% yield).

To (4bS,6S,8aR,9R)-11-(cyclobutylmethyl)-6-hydroxy-6,7,8,8a,9,10-hexahydro-5H-9,4b-(epiminoethano)phenanthrene-3-carboxamide (50 mg, 0.14 mmol) in ethyl acetate (4 mL) was added 2M HCl in diethyl ether (0.07 mL, 0.70 mmol). The solvent was removed under vacuum before freeze drying from water to give (4bS,6S,8aR,9R)-11-(cyclobutylmethyl)-6-hydroxy-6,7,8,8a,9,10-hexahydro-5H-9,4b-(epiminoethano)phenanthrene-3-carboxamide hydrochloride (55 mg, 99.0% pure LCMS, 100% yield); [M+H]$^+$ 355.3. $^1$H NMR (300 MHz, D$_2$O) 7.76 (1H, s), 7.44 (1H, d), 7.16 (1H, d), 4.02 (1H, s), 3.58 (1H, s), 2.88-3.44 (5H, m), 2.70 (1H, d), 2.55 (1H, m), 2.35 (1H, dt), 0.99-2.16 (14H, m).

Part B. Biological Assays

B1. In Vitro Characterization

The in vitro kinetic and pharmacological characteristics of the compounds set forth in Table B and Table C were tested using the following assays.

Opioid Receptor Binding Assay

The K$_i$ (binding affinity) for opioid receptors was determined using a competitive displacement assay as previously described in Neumeyer (Journal of Med. Chem. 2012, p 3878), which is incorporated herein in its entirety. Briefly, membrane protein from CHO (Chinese Hamster Ovarian) cells that stably expressed the cloned human opioid receptor were incubated with 12 different concentrations of the compound set forth herein in the presence of 0.25 nM [3H]DAMGO (see Tiberi et al., Can. J. Physiol. Pharmacol. 1988, Vol. 66, p 1368, which is incorporated by reference herein in its entirety) in a final volume of 1 mL of 50 mM Tris-HCl, pH 7.5 at 25° C. Incubation times of 60 min were used for [3H]DAMGO (see Gulati et al., Life Sci. 1990, Vol. 47, p 159, which is incorporated by reference herein in its entirety). Nonspecific binding was measured by inclusion of 10 M naloxone. The binding was terminated by filtering the samples through Schleicher & Schuell No. 32 glass fiber filters using a Brandel 48-well cell harvester. The filters were subsequently washed three times with 3 mL of cold 50 mM Tris-HCl, pH 7.5, and were counted in 2 mL Ecoscint A scintillation fluid. IC50 values were calculated by least squares fit to a logarithm-probit analysis. Ki values of unlabelled compounds were calculated from the equation Ki=(IC50)/1+S where S=(concentration of radioligand)/(Kd of radioligand) (Cheng and Prusoff, 1973). The calculated IC50 and Ki values for the compounds tested are set forth in Table B and Table C, herein.

Functional Assay (GTPγS Binding)

The EC50 and Imax for opioid receptors was determined using a [$^{35}$S]GTPγS binding assay. This assay measures the functional properties of a compound by quantifying the level of G-protein activation following agonist binding in studies using stably transfected cells, and is considered to be a measure of the efficacy of a compound. Membranes from CHO (Chinese Hamster Ovary) cells that stably expressed the cloned human Mu opioid receptor were used in the experiments. Specifically, in a final volume of 0.5 mL, 12 different concentrations of each test compound were incubated with 7.5 g of CHO cell membranes that stably expressed the human μ opioid receptor. The assay buffer consisted of 50 mM Tris-HCl, pH 7.4, 3 mM MgCl2, 0.2 mM EGTA, 3 M GDP, and 100 mM NaCl. The final concentration of [35S]GTPγS was 0.080 nM. Nonspecific binding was measured by inclusion of 10 μM GTPγS. Binding was initiated by the addition of the membranes. After an incubation of 60 min at 30° C., the samples were filtered through Schleicher & Schuell No. 32 glass fiber filters. The filters were washed three times with cold 50 mM Tris-HCl, pH 7.5, and were counted in 2 mL of Ecoscint scintillation fluid. Data are the mean Emax and EC50 values±S.E.M. For calculation of the Emax values, the basal [35S]GTPγS binding was set at 0%, and the 100% [35S]GTPγS binding level was set at the maximum binding achieved with DAMGO. To determine antagonist activity of a compound at the μ opioid receptors, CHO membranes expressing the t opioid receptor, were incubated with 12 different concentrations of the compound in the presence of 200 nM of the μ agonist DAMGO. The Emax values are the maximal percentage increase of [35S]GTPγS binding induced by a test compound relative to basal [35S]GTPγS binding in the absence of any drug. Data for antagonists are the mean Imax and IC50 values±S.E.M. The calculated EC50 and Imax values for the compounds tested are set forth in Table B and Table C, herein. It should be noted that the GTPγS binding assay described above is performed under conditions such that the observed Emax value for buprenorphine in this assay is at least 50% compared to baseline.

TABLE B

| Structure | mu_Ki | mu_EC50 | mu_Emax | mu_IC50 | mu_Imax |
|---|---|---|---|---|---|
| 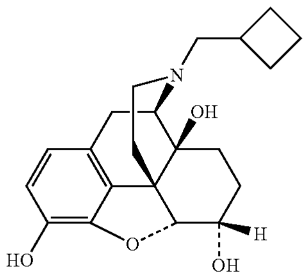 [SMILES: Oc1ccc2c3c1O[C@H]1[C@@H](O)CC[C@@]4(O)[C@@H](C2)N(CC2CCC2)CC[C@]314] | 0.98 | 34 ± 17 | 26 | 87 ± 13 | 74 ± 3 |
| 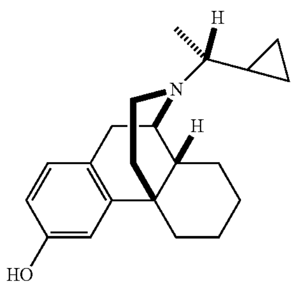 | 0.079 | 0.56 | 25 | 2.2 | 68 |
| 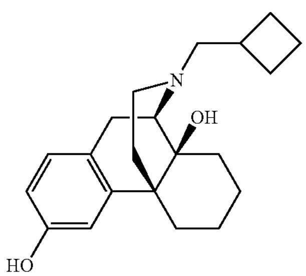 [SMILES: Oc1ccc2c(c1)[C@@]13CCCC[C@@]1(O)[C@@H](C2)N(CC1CCC1)CC3] | 0.19 | 3.3 | 27 | 28 | 66 |
| 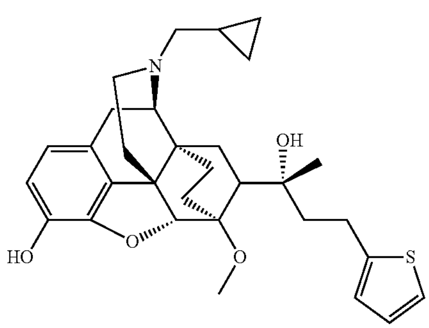 [SMILES: CO[C@]12CC[C@@]3(CC1[C@](C)(O)CCc1cccs1)[C@H]1Cc4ccc(O)c5c4[C@@]3(CCN1CC1CC1)[C@H]2O5] | 0.43 | 0.35 | 64 | 0.28 | 30 |
| 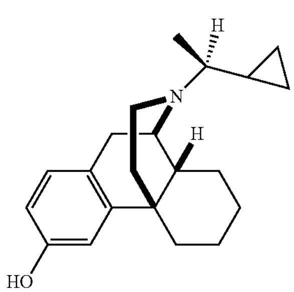 | 18 | 50 | 29 | 970 | 67 @ 10 uM |

TABLE B-continued

| Structure | mu_Ki | mu_EC50 | mu_Emax | mu_IC50 | mu_Imax |
|---|---|---|---|---|---|
| (structure) | 0.061 | 1.1 | 28 | 0.71 | 67 |
| (structure) | 0.54 | 20 | 47 | 130 | 47 |
| (structure) | 2.7 | 61 | 38 | 280 | 64 |
| (structure) | 0.08 | 1.3 | 24 | 10 | 74 |
| (structure) | 22 | >630 | 56 | NI | NI |
| (structure) | 32 | >600 | 59 | | 16% @ 10 uM |
| (structure) | 0.49 | 16 | 56 | 74 | 42 |

TABLE B-continued

| Structure | mu_Ki | mu_EC50 | mu_Emax | mu_IC50 | mu_Imax |
| --- | --- | --- | --- | --- | --- |
| 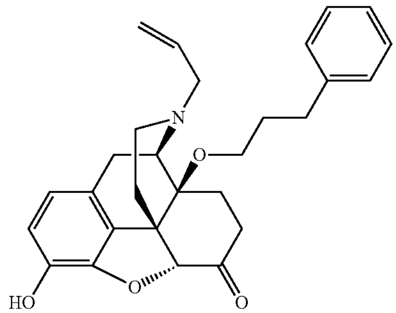 [SMILES: C=CCN1CC[C@]23c4c5ccc(O)c4O[C@H]2C(=O)CC[C@@]3(OCCCc2ccccc2)[C@H]1C5] | 0.2 | 0.19 | 56 | 0.18 | 53 |
| 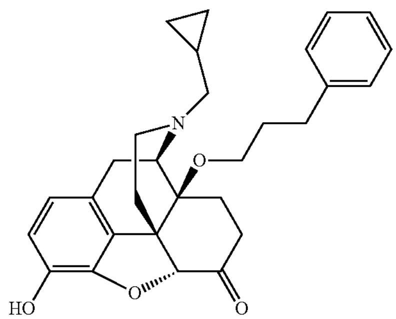 [SMILES: O=C1CC[C@@]2(OCCCc3ccccc3)[C@H]3Cc4ccc(O)c5c4[C@@]2(CCN3CC2CC2)[C@H]1O5] | 0.061 | 0.075 | 34 | 0.079 | 59 |
| 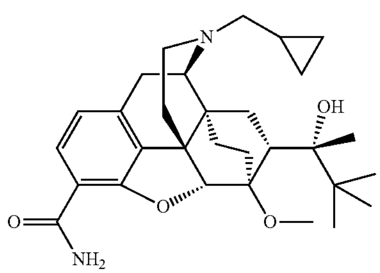 [SMILES: CO[C@]12CC[C@@]3(C[C@@H]1[C@](C)(O)C(C)(C)C)[C@H]1Cc4ccc(C(N)=O)c5c4[C@@]3(CCN1CC1CC1)[C@H]2O5] | 0.77 | 1.8 | 38 | 1.6 | 57 |
| 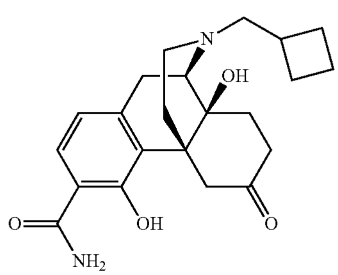 [SMILES: NC(=O)c1ccc2c(c1O)[C@]13CCN(CC4CCC4)[C@H](C2)[C@]1(O)CCC(=O)C3] | 0.16 | 1 ± 0.11 | 31 ± 1 | 2.2 ± 0.5 | 69 ± 1.5 |
| 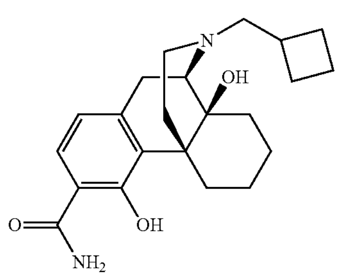 [SMILES: NC(=O)c1ccc2c(c1O)[C@@]13CCCC[C@@]1(O)[C@@H](C2)N(CC1CCC1)CC3] | 0.28 | 1.4 ± 0.06 | 30 ± 2.2 | 4.2 ± 0.6 | 71 ± 0.8 |

TABLE B-continued

| Structure | mu_Ki | mu_EC50 | mu_Emax | mu_IC50 | mu_Imax |
| --- | --- | --- | --- | --- | --- |
| (structure) | 0.11 | 1.1 ± 0.3 | 29 ± 1 | 2.0 ± 0.3 | 74 ± 2 |
| (structure) Compound C | 0.59 ± 0.07 | 2.8 ± 0.3 | 18 ± 1 | 47 | 78.5 ± 4.5 |
| (structure) Compound D | 0.10 ± 0.04 | 0.98 ± 0.12 | 18 ± 5 | 3.8 | 80 ± 1 |
| (structure) | 0.097 | 0.53 | 28 | 1.3 | 65 |

TABLE B-continued
| Structure | mu_Ki | mu_EC50 | mu_Emax | mu_IC50 | mu_Imax |
|---|---|---|---|---|---|
| 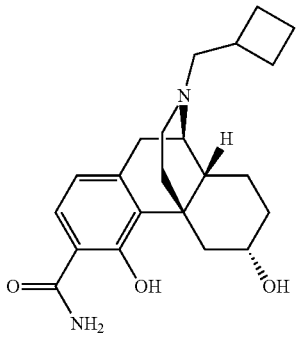 Compound E | 0.22 | 3.3 | 33 | 14 | 69 |
| 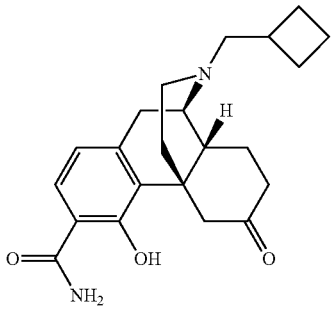 [SMILES: NC(=O)c1ccc2c(c1O)[C@]13CCN(CC4CCC4)[C@H](C2)[C@@H]1CCC(=O)C3] | 0.097 | 0.39 | 42 | 1.1 | 54 |
| 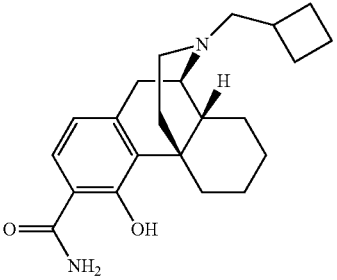 [SMILES: NC(=O)c1ccc2c(c1O)[C@@]13CCCC[C@H]1[C@@H](C2)N(CC1CCC1)CC3] | 0.12 | 2.1 | 38 | 5 | 63 |
| 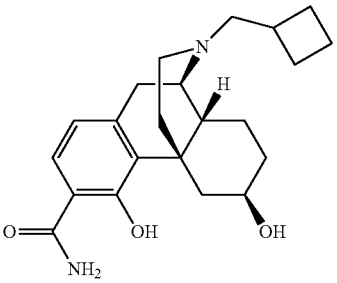 [SMILES: NC(=O)c1ccc2c(c1O)[C@]13CCN(CC4CCC4)[C@H](C2)[C@@H]1CC[C@@H](O)C3] | 0.13 | 1.5 | 44 | 3.7 | 66 |
| 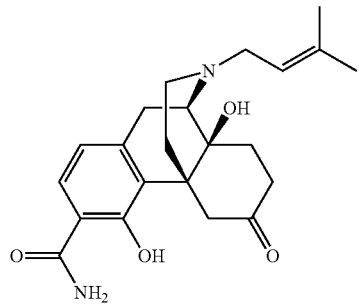 [SMILES: CC(C)=CCN1CC[C@]23CC(=O)CC[C@@]2(O)[C@H]1Cc1ccc(C(N)=O)c(O)c13] | 0.56 | 4.2 | 49 | 34 | 54 |

TABLE B-continued

| Structure | mu_Ki | mu_EC50 | mu_Emax | mu_IC50 | mu_Imax |
|---|---|---|---|---|---|
| 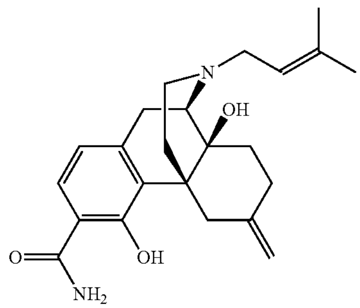 [SMILES: C=C1CC[C@@]2(O)[C@H]3Cc4ccc(C(N)=O)c(O)c4[C@@]2(CCN3CC=C(C)C)C1] | 0.5 | 15 | 35 | 51 | 70 |
| 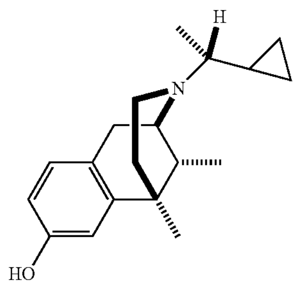 | 0.19 | 2.3 | 36 | 14 | 55 |
| 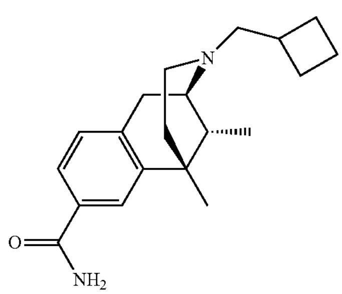 [SMILES: C[C@H]1[C@H]2Cc3ccc(C(N)=O)cc3[C@]1(C)CCN2CC1CCC1] | 0.1 | 3.5 | 32 | 3.3 | 73 |
| 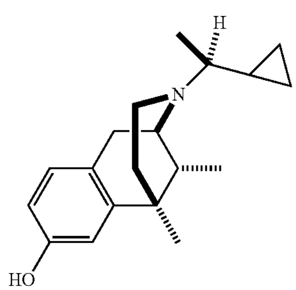 | 22 | 60 | 27 | 950 | 65 |
| 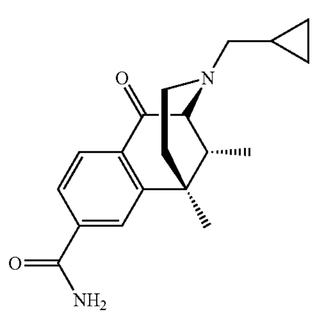 | 1.2 | 12 | 35 | 69 | 65 |

TABLE B-continued
| Structure | mu_Ki | mu_EC50 | mu_Emax | mu_IC50 | mu_Imax |
|---|---|---|---|---|---|
| 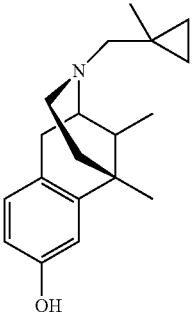 | 0.82 | 13 | 26 | 85 | 76 |
| 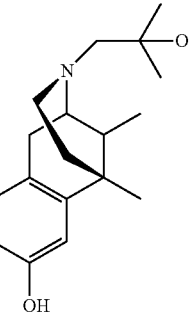 | 4.6 | 84 | 23 | 210 | 74 |
| 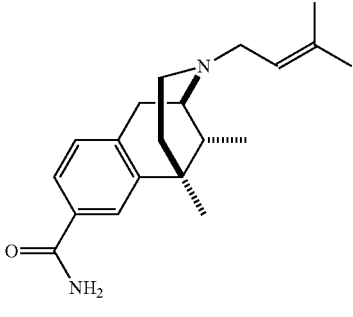 | 2.1 | 110 (12) | 43 (7) | >1300 (280) | 53% @ 10 uM |
| 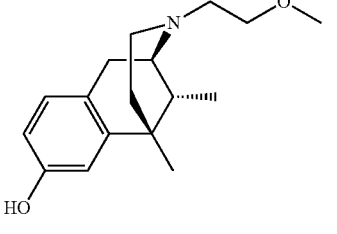 | 0.11 | 4.8 | 53 | 26 | 37 |
| 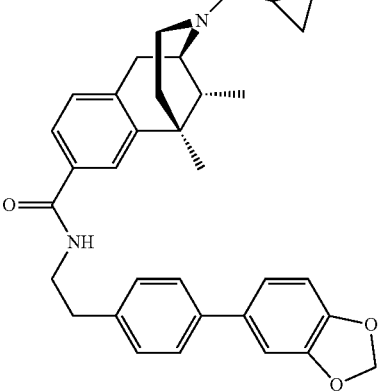 | 0.2 | 0.59 | 51 | 0.84 | 57 |

TABLE B-continued

| Structure | mu_Ki | mu_EC50 | mu_Emax | mu_IC50 | mu_Imax |
|---|---|---|---|---|---|
| *(structure)* | 0.26 | 0.85 | 48 | 3.5 | 53 |
| *(structure)* | 0.3 | 1.4 | 48 | 1.1 | 56 |
| *(structure)* | 0.68 | 22 | 25 | 47 | 83 |
| *(structure)* | 0.17 | 2.6 | 19 | 5.2 | 79 |

TABLE B-continued
| Structure | mu_Ki | mu_EC50 | mu_Emax | mu_IC50 | mu_Imax |
|---|---|---|---|---|---|
| 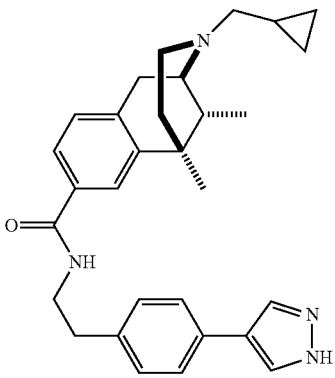 | 0.27 | 5.2 | 32 | 18 | 59 |
| 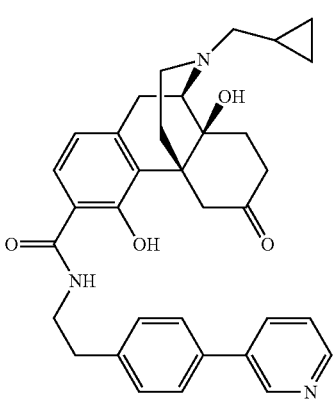 [SMILES: O=C1CC[C@@]2(O)[C@H]3Cc4ccc(C(=O)NCCc5ccc(-c6cccnc6)cc5)c(O)c4[C@@]2(CCN3CC2CC2)C1] | 0.37 | 2.9 | 46 | 1.5 | 43 |
| 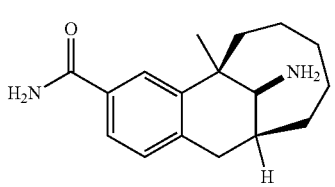 [SMILES: C[C@@]12CCCCC[C@@H](Cc3ccc(C(N)=O)cc31)[C@@H]2N] | 2.3 | 62 | 18 | 170 | 87 |
| Rac 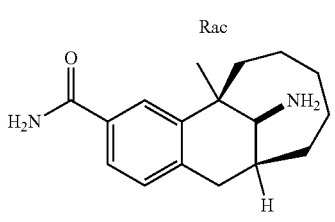 | 3 | 41 | 19 | 170 | 83 |
| 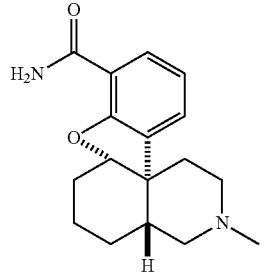 | 23 | 190 | 35 | >3000 | 57 @ 10 uM |

TABLE B-continued

| Structure | mu_Ki | mu_EC50 | mu_Emax | mu_IC50 | mu_Imax |
|---|---|---|---|---|---|
| (structure) | 4.4 | 20 | 20 | 340 | 76 |
| (structure) | 1.2 |  | 1.6 | 44 | 85 |

TABLE C

| Compound | μ Ki/nm | μ EC50/nM | μ Emax/% | μ IC50/nM | μ Imax/% |
|---|---|---|---|---|---|
| (structure) | 0.083 | 1.3 | 18 | 1.7 | 82 |
| (structure) | 0.14 |  | 11 | 0.65 | 86 |
| (structure) | 5.8 | — | 7.7 | 43 | 91 |

TABLE C-continued

| Compound | μ Ki/nm | μ EC50/nM | μ Emax/% | μ IC50/nM | μ Imax/% |
|---|---|---|---|---|---|
| [structure] | 1.2 | — | 11 | 38 | 86 |
| [structure] | 0.12 | 2.2 | 46 | 14 | 41 |
| [structure] | 0.098 | 2.5 | 54 | 7.8 | 59 |
| [structure] | 0.1 | 0.89 | 21 | 1.5 | 80 |
| [structure] | 0.05 | | 20 | 58 | 89 |
| morphine | 0.32 | 34 ± 14 | 96.5 ± 36 | No inhibition | No inhibition |
| nalbuphine | 1.3 ± 0.4 | 21 ± 15 | 26 ± 1.55 | 88 ± 18 | 74 ± 2 |
| buprenorphine | 0.41 | 0.30 ± 0.042 | 53 ± 2.3 | 0.45 ± 0.060 | 48 ± 1.7 |

B2. Thermal Pain Assay

The antinociceptive effect of the compounds disclosed herein is determined using a rodent hot plate model. This model tests the responses to acute thermal pain in rats as set forth below.

Male Sprague-Dawley rats (275-425 g) are used for all studies. Rats are housed 2/cage and are given food and water ad libitum. Body weights were taken once before testing begins and rats were marked on their tail to indicate numbering. The hot plate apparatus (Columbus Instruments) was used to measure antinociception to acute thermal pain.

Rats are placed individually on the hot plate apparatus (surface temperature is equal to 52.5° C. and is confirmed with an infrared thermometer at the beginning of each study) and the response latency to lick either hind paw is recorded. The maximum response latency (MRL) is set to 60 seconds to avoid potential thermal injury associated with longer exposure times. Rats are tested for a baseline hot plate response (licking one hind paw) immediately prior to subcutaneous injection with test compound. Any rat which displays a baseline response latency greater than 30 seconds is removed from the study. The latency to lick a hind paw is compared to the dose of morphine (7.5 mg/kg, SC) that produced a maximum response latency of 60 seconds when measured 30 minutes after administration. Following test compound administration, rats are tested 30, 60, 90, 120, and 240 minutes later on the hot plate. The time to lick one hind paw is recorded as the response latency for each rat.

Raw data is reported as the time (in seconds) to lick one hind paw following exposure to the hot plate. The mean and SEM of the responses latencies for each experimental group are calculated and a line graph depicting mean hot plate latency vs. time is generated using GraphPad Prism. An increase in mean response latency above baseline following test compound administration is indicative of an antinociceptive effect.

In one study, the antinociceptive effects of Compound A, either alone or in combination with morphine were determined using the hot plate assay described above. Specifically, rats were administered: 1) 5 mg/kg morphine; 2) 1 mg/kg Compound A; 3) 5 mg/kg morphine and 0.01 mg/kg Compound A; 4) 5 mg/kg morphine and 0.1 mg/kg Compound A; or 5) 5 mg/kg morphine and 1 mg/kg Compound A. The results, set forth in FIG. 1, show that although Compound A inhibits morphine analgesia at doses ranging from 0.01 mg/kg to 1 mg/kg, Compound A alone has no antinociceptive effect at a dose of 1 mg/kg.

Figure 2:
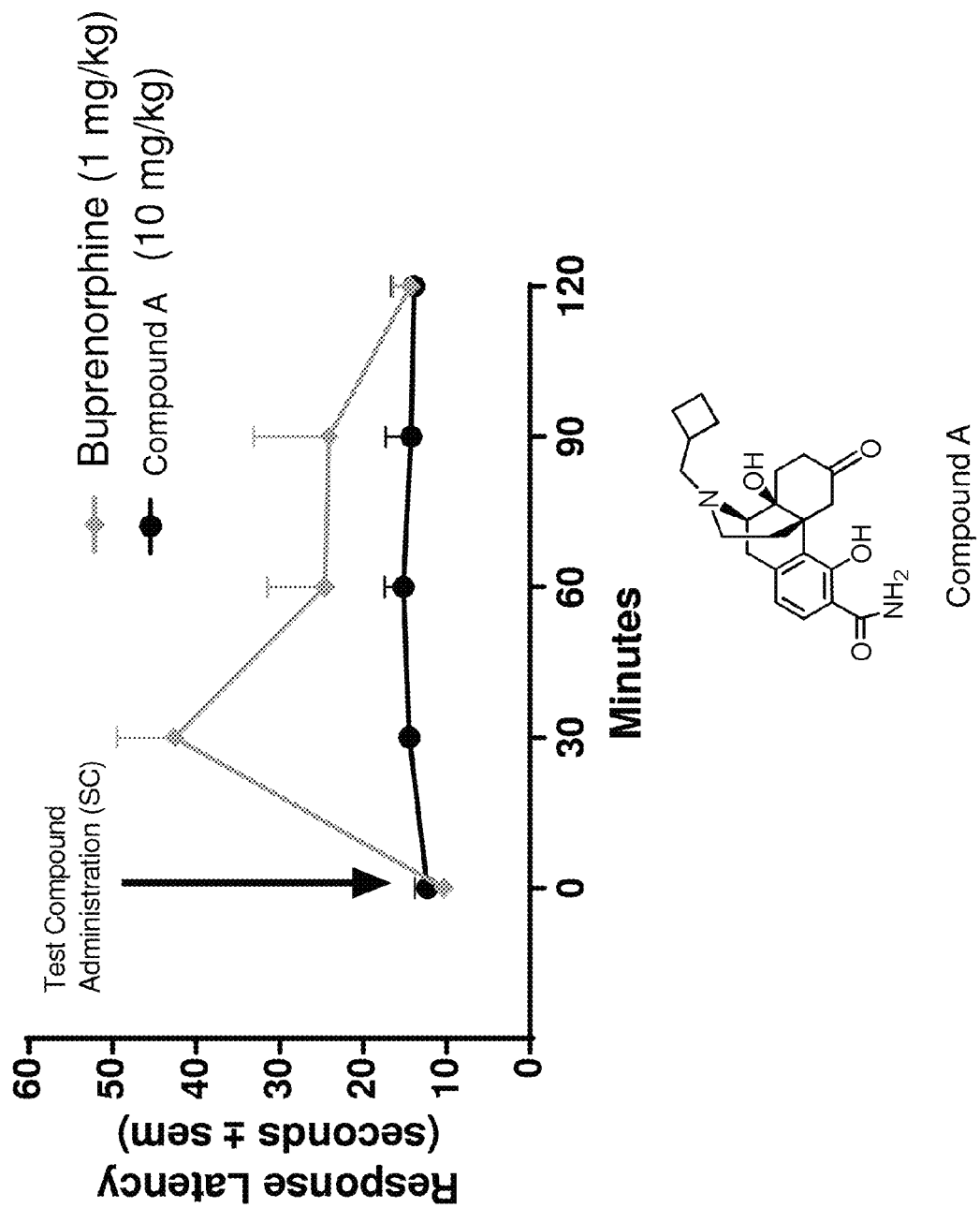
FIG. 2 depicts the results of experiments measuring the antinociceptive effects of Compound A, or buprenorphine using a rat hot plate assay.

In another study, the antinociceptive effects of Compound A and buprenorphine were compared using the hot plate assay described above. Specifically, rats were administered with either 10 mg/kg of Compound A, or 1 mg/kg of buprenorphine. The results, set forth in FIG. 2, show that buprenorphine inhibits thermal pain in rats at a dose of 1 mg/kg, whereas Compound A has no antinociceptive effect at a dose of 10 mg/kg.

Figure 4:
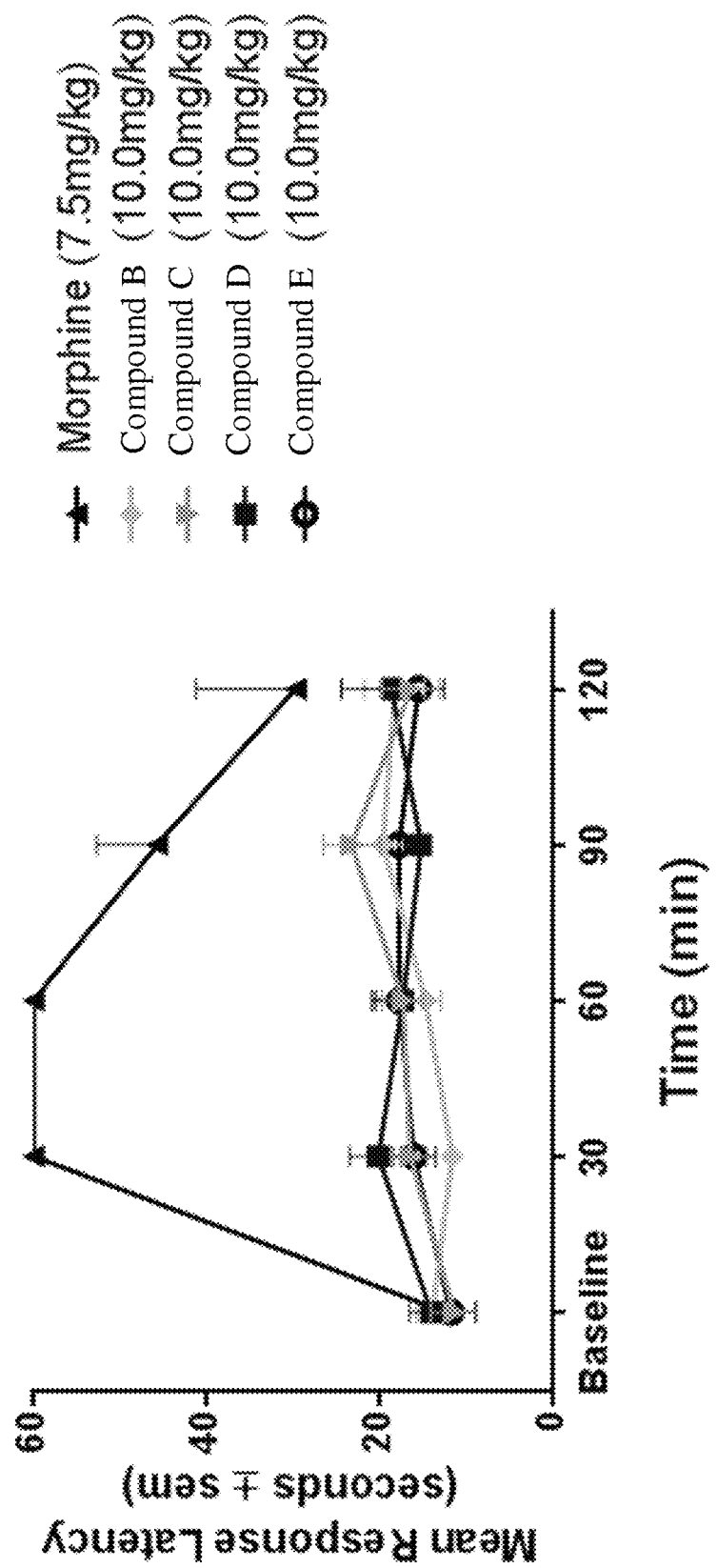
FIG. 4 depicts the results of experiments measuring the antinociceptive effects of morphine, Compound B, Compound C, Compound D and Compound E, using a rat hot plate assay.
Figure 5:
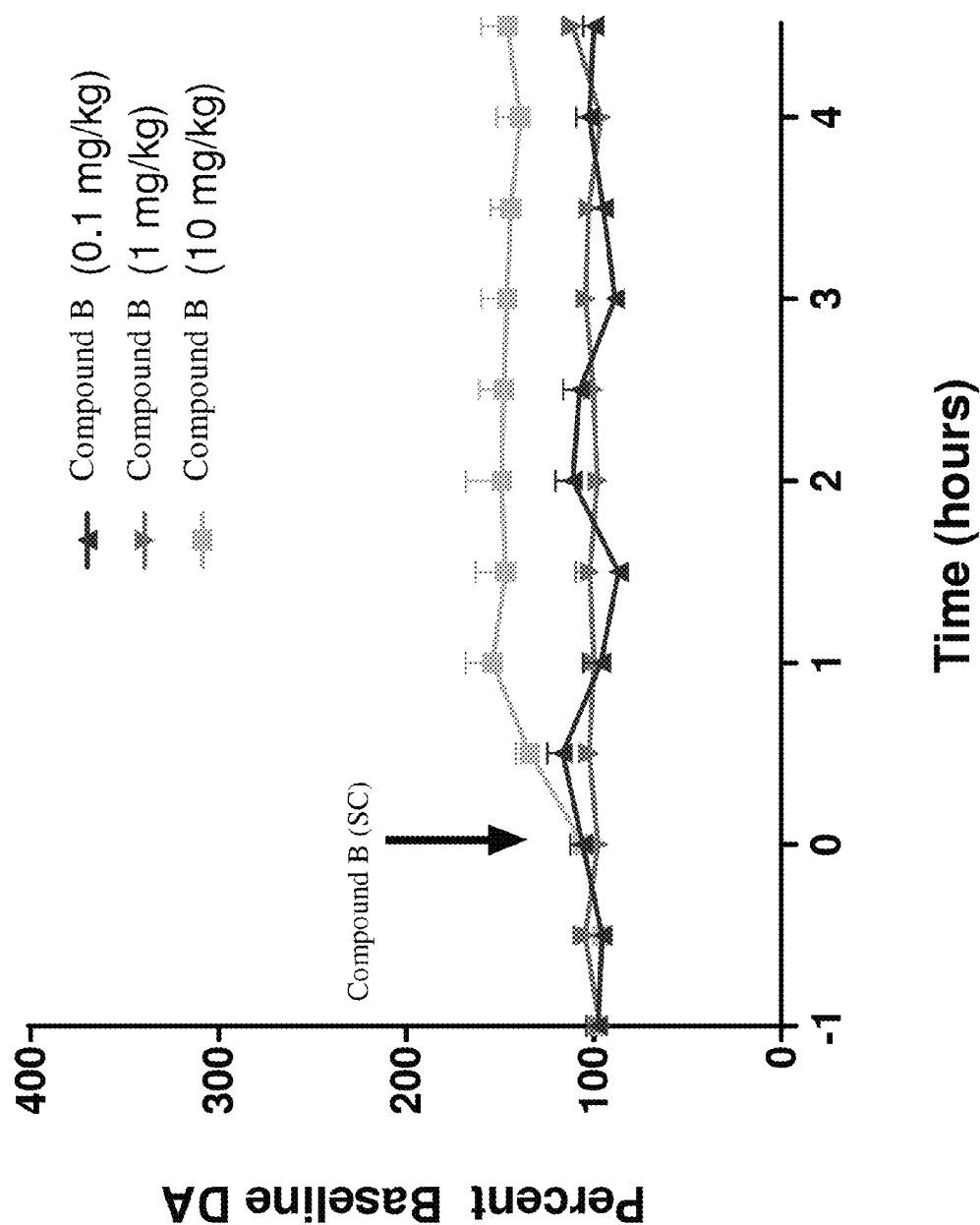
FIG. 5 depicts the results of in vivo microdialysis experiments measuring dopamine release in the rat nucleus accumbens induced by different doses of Compound B.
Figure 6:
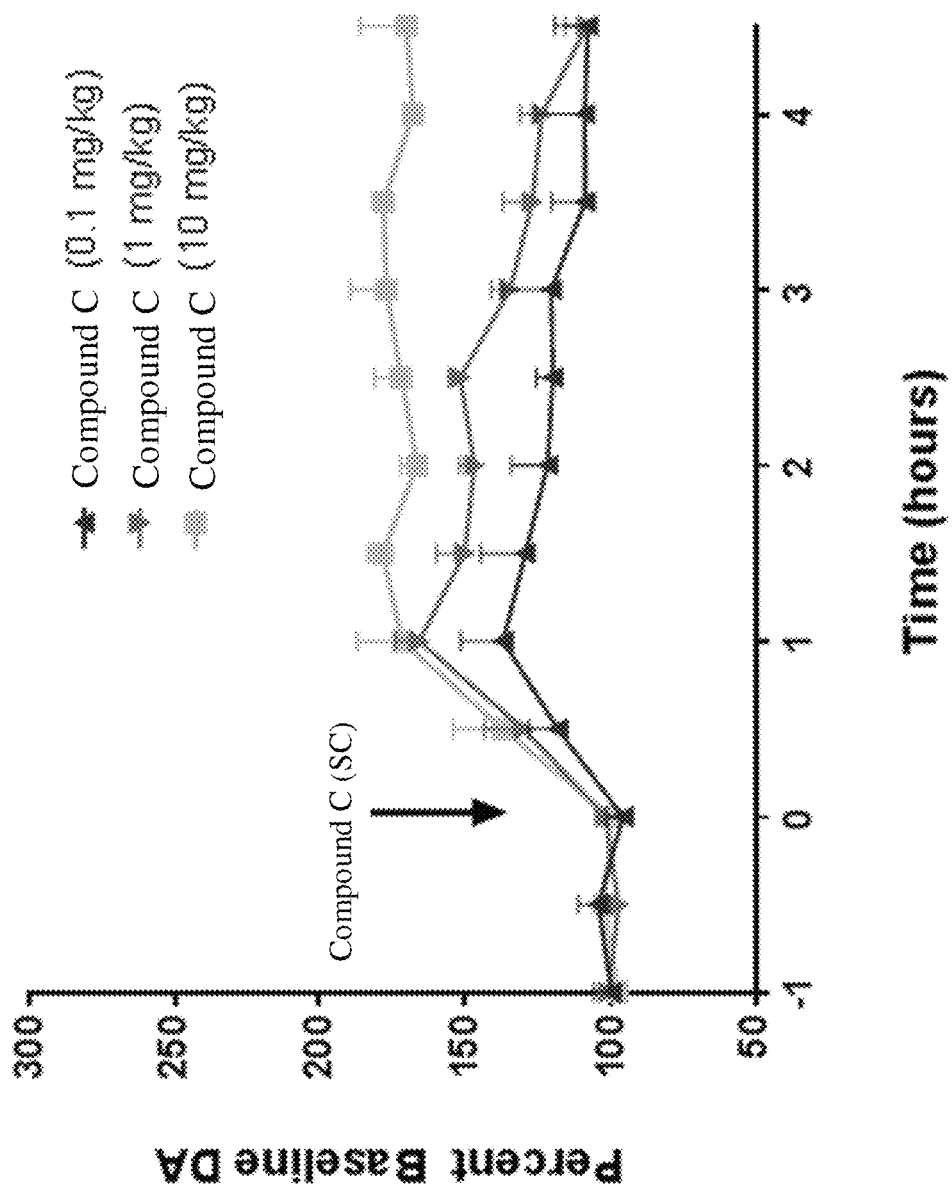
FIG. 6 depicts the results of in vivo microdialysis experiments measuring dopamine release in the rat nucleus accumbens induced by different doses of Compound C.
Figure 7:
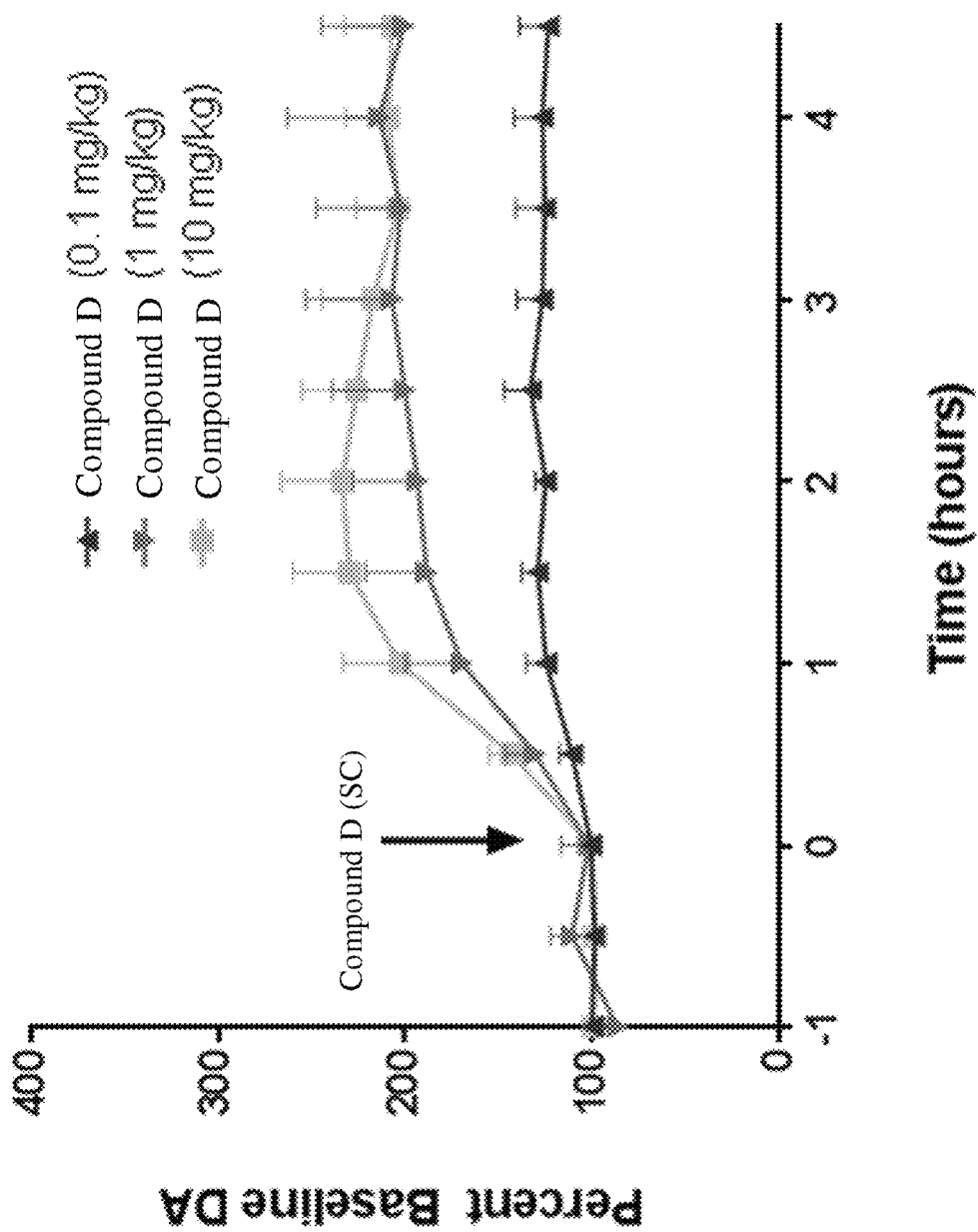
FIG. 7 depicts the results of in vivo microdialysis experiments measuring dopamine release in the rat nucleus accumbens induced by different doses of Compound D.
Figure 8:
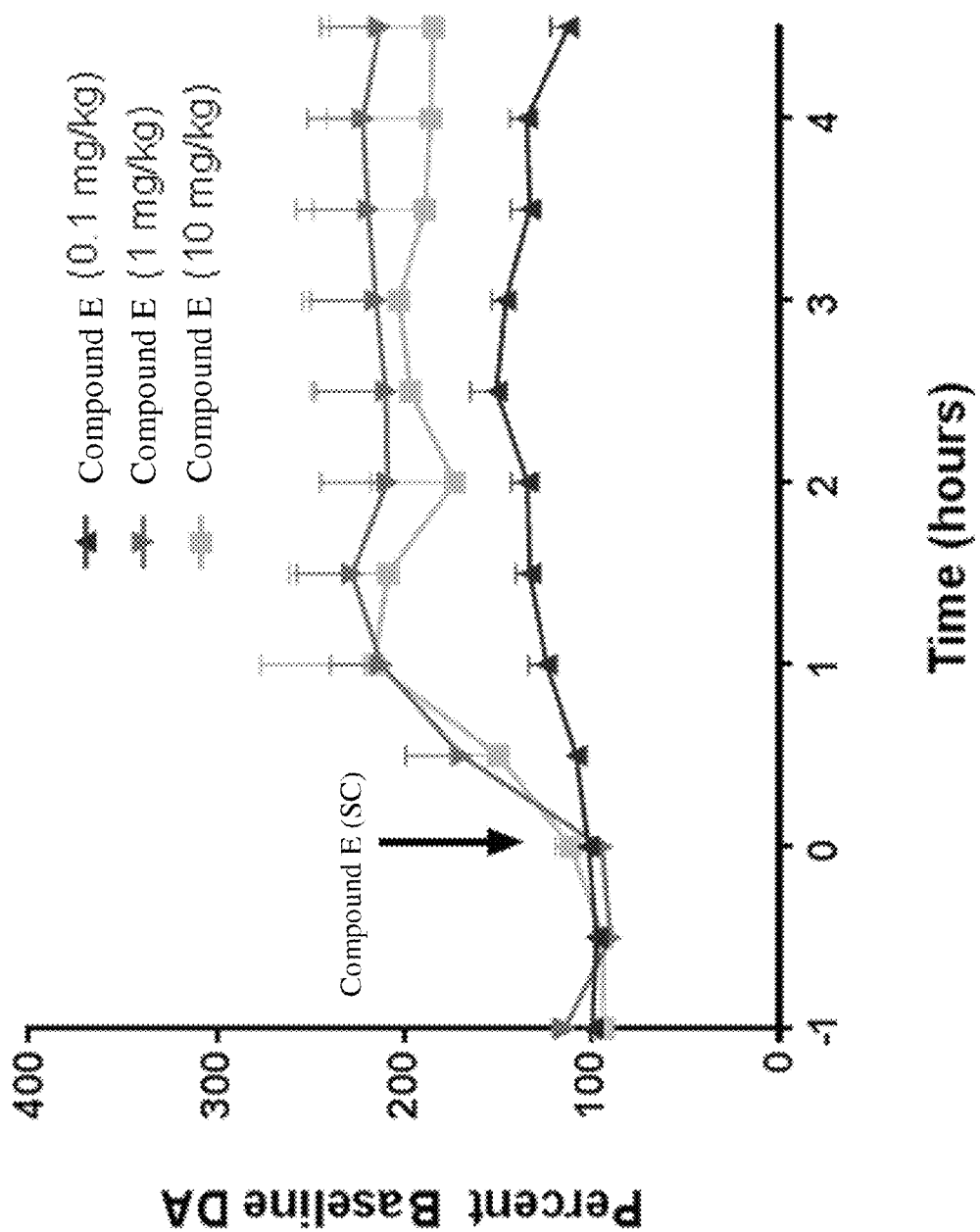
FIG. 8 depicts the results of in vivo microdialysis experiments measuring dopamine release in the rat nucleus accumbens induced by different doses of Compound E.

In another study, the antinociceptive effects of morphine, and Compounds B, C, D, and E, separately, were determined using the hot plate assay described above. Specifically, rats were administered: 1) 7.5 mg/kg morphine; 2) 10.0 mg/kg Compound B; 3) 10.0 mg/kg Compound C; 4) 10.0 mg/kg Compound D; or 5) 10.0 mg/kg Compound E. The results, set forth in FIG. 4, show that morphine inhibits thermal pain at a dose of 7.5 mg/kg, and that Compounds B, C, D, or E have no antinociceptive effect at a dose of 10.0 mg/kg.

B3. In Vivo Dopamine Efflux Assay

The neurochemical response of the compounds disclosed herein is determined by in vivo microdialysis in awake rats. Intra-cranial microdialysis in rats allows the sampling of extracellular cerebrospinal fluid (CSF) from specific brain regions of interest and the measurement and quantitation of neurotransmitter, neuropeptide, and drug concentrations following the analysis of sampled dialysate with bioanalytical chemistry techniques. This technique allows measurement and comparison of neurotransmitter release in response to test compounds to basal neurotransmitter levels. The nucleus accumbens shell is a brain region which is critically important for understanding the rewarding effects of a variety of stimuli including food, mating behavior and drugs of abuse. Rewarding stimuli have been shown to act though multiple pathways to modulate the mesolimbic dopamine system, ultimately resulting in acute increases in extracellular DA ($DA_{ext}$) within the nucleus accumbens shell following systemic administration or self-administration. In these studies, microdialysate collected from probes implanted in the NAc-sh is analyzed for dopamine content by HPLC coupled to electrochemical detection (HPLC-EC) as set forth below.

Male Wistar rats (275-425 g) are used for all studies. Rats were housed 2/cage and are given food and water ad libitum. Approximately 3-4 days after arrival to the animal facility, rats underwent surgical implantation of microdialysis guide cannula to guide insertion of the microdialysis probe. Rats are anesthetized with a mixture of ketamine/xylazine (80/6 mg/kg IP) and placed in a stereotaxic apparatus. Ophthalmic lubricating petroleum based ointment is applied to the eyes as needed. The surgical area is shaved and prepared with a betadine scrub and wiped with alcohol. The skull is exposed and small burr holes were drilled to allow for the guide cannula to pass through and for the mounting screws to be attached to the skull. Guide cannula (CMA-12, CMA-Microdialysis, SWE) are stereotaxically implanted towards the NAc-sh (final microdialysis coordinates relative to bregma: A/P+1.70; M/L±0.80; D/V −5.90 from the top of the skull) (Paxinos and Watson, "The Rat Brain", 6th Edition, 2008). Each guide cannula is secured with 3, ⅛" skull screws (Small Parts Inc, USA) and cranioplastic cement (GC Fuji Plus Capsule; Henry Schein, USA). Following 3-4 days of recovery, microdialysis probes (CMA-12, CMA-Microdialysis, SWE) with a 2 mm active membrane length are inserted through the guide cannula and rats are individually tethered to a CMA 120 microdialysis system (CMA-Microdialysis, SWE). Rats are continuously perfused overnight with sterile artificial cerebrospinal fluid (aCSF) (CMA CNS Perfusion Solution; CMA-Microdialysis, SWE) via a syringe pump at 0.2 μl/minute. The following morning, continuous perfusion of aCSF was increased to 2.0 μl/minute and the flow rate was equilibrated for at least 2 hours prior to experimentation.

Microdialysis occurred on the day following probe insertion. Microdialysis samples are collected automatically at 15 minute intervals via a chilled microfraction collector for a total of 6.0 hours. Following equilibration, a 1.5 hour baseline measurement (6 fractions) of neurotransmitter levels is collected. Following baseline measurements, rats are separately administered various concentrations of test compound. Fractions were analyzed via HPLC-EC to determine dopamine concentrations.

Microdialysis fractions are analyzed via HPLC-EC using an Alexys Monoamine Analyzer (Antec Leyden, NLD) or via UHPLC-EC using an Alexys Neurotransmitter Analyzer. For HPLC-EC detection, an aliquot of each fraction (10 ul) is injected onto a 1 μm reverse-phase C18 column (HSS-T3, Waters Corp., Milford, Mass.). DA is eluted using a mobile phase (pH 6.0) consisting of 50 mM phosphoric acid, 8 mM KCL, 0.1 mM EDTA, 6.5% acetonitrile, and 1200 mg/L octane sulfonic acid. DA is detected using a Decade II amperometric detector (Antec Leyden) with a glassy carbon electrode maintained at approximately 0.460V relative to a salt-bridge reference electrode. For UHPLC-EC detection, an aliquot of each fraction (10 ul) is injected onto a 1 μm reverse-phase C18 column (HSS T3, Waters Corp., Milford, Mass.). DA is eluted using a mobile phase (pH 4.00) consisting of 50 mM phosphoric acid, 8 mM KCL, 50 mM Citric Acid, 0.1 mM EDTA, 6.5% acetonitrile, and 600 mg/L octane sulfonic acid. DA is detected using a Decade II amperometric detector (Antec Leyden) with a glassy carbon electrode maintained at approximately 0.55V relative to a Ag/AgCl reference electrode.

All data is recorded and analyte levels quantitated using a Clarity 3.0 software package (Data Apex, Czech Republic). A 6-point standard curve (0.25, 0.5, 1.0, 2.0, 4.0 and 8.0 pg DA/10 μl injection) is run daily prior to neurotransmitter analysis. The standard curve is fitted linearly and neurotransmitter content in microdialysate samples is quantitated based on the corresponding standard curve. The amount of dopamine or metabolites is quantified as "on-column" in picograms of analyte per 10 μl sample injection onto the column. Raw data are reported as picograms of dopamine per 10 μl sample and transformed (using Graph Pad Prism 5.0) to percentage of pre-drug baseline for each animal, as defined as the average of the six baseline microdialysis samples. Percentage change from baseline vs. time is then graphed using GraphPad Prism 5.0. Following completion of the study, all animals are analyzed via histological methods to ensure proper probe placement with the nucleus accumbens shell. Those animals with probe placement outside of the nucleus accumbens shell are excluded from the final data analysis To verify probe placement, rats are euthanized with an IP injection of 50% Euthasol (Virbac, AH Inc, Fort Worth, Tex.) shortly after microdialysis. Brains are rapidly dissected and frozen on dry ice and stored at −80° C. Coronal sections (approximately 60-μm) are then sliced at the level of the nucleus accumbens and digitally photographed for archival purposes. Only data from animals with verified probe placement are included in data analysis.

In one study, the amount of dopamine release induced by Compound A and buprenorphine in the rat nucleus accumbens was determined using the microdialysis assay herein. Specifically, rats were separately administered with Compound A (at 0.01 mg/kg, 0.1 mg/kg, or 1 mg/kg) or buprenorphine (at 0.001 mg/kg, 0.003 mg/kg, 0.01 mg/kg, 0.1 mg/kg, or 1 mg/kg) and microdialysate was sampled for 4.5 hours (18 fractions). The results of these experiments are set forth in FIG. 3. These data show that Compound A induced a dose dependent increase in dopamine efflux in the rat nucleus accumbens, achieving a maximum dopamine efflux of about 300% over baseline at 0.1 mg/kg of Compound A. Buprenorphine also induced a dose dependent increase in dopamine efflux. Although, no maximum dopamine efflux level for buprenorphine was determined, the maximum dopamine efflux induced by buprenorphine is clearly much greater than that obtainable using Compound A. The lower ceiling level of dopamine efflux of exhibited by Compound A relative to buprenorphine indicates that Compound A will likely have a lower risk of opioid dependence, opioid addiction and/or opioid withdrawal symptoms compared to buprenorphine.

In other studies, the amount of dopamine release induced by Compounds B, C, D, and E in the rat nucleus accumbens was determined using the microdialysis assay herein. Specifically, rats were administered (via subcutaneous injection at T=0) separately with Compounds B, C, D, or E at doses of 0.1 mg/kg, 1 mg/kg, or 10 mg/kg, and microdialysate was continuously sampled for 4.5 hours. The results of these experiments are set forth in FIGS. 5-8. Compound B exhibited a maximum dopamine efflux of about 150% to about 200% over baseline at a dose of 10 mg/kg. Compound C exhibited a maximum dopamine efflux of about 125% to about 200% over baseline at the three dose levels. Compounds D and E exhibited a maximum dopamine efflux of about 125% to about 250% over baseline at the three dose levels. These low ceiling levels of dopamine efflux indicate that Compounds B, C, D, and E will likely have a lower risk of opioid dependence, opioid addiction and/or opioid withdrawal symptoms.

B4. In Vivo Forced Swim Test

The Forced Swim Test is a classical preclinical model used to assess antidepressant effects of test compounds in rats. Rats forced to swim in an inescapable cylinder adopt a characteristic immobile posture after a period of vigorous swimming. Immobility has been shown to be reduced by most clinically effective antidepressant drugs. Furthermore, this paradigm has the benefit of being able to distinguish potential antidepressant compounds from other behavioral paradigms that measure activities (open-field) or other compounds that might have dose-dependent effects on general locomotor activities unrelated to mood.

A male, Wistar-Kyoto rat is placed into its assigned clear Plexiglas cylinders of water (23-25° C.) for a 15-min pretest swim. A compound is then administered in the rat by subcutaneously (sub-Q) injections following a dosing schedule. The sub-Q dosing schedule includes one injection at 0.5 hr after the pretest swim, one injection at 5 hrs before a test swim, and one injection at 1 hr before the test swim. Each test swim lasts 6 minutes, and this test swim is carried out within 24 hours after the pretest swim. The test swim is recorded using a digital video recording system and subsequently analyzed manually for immobility behavior.

Figure 9:
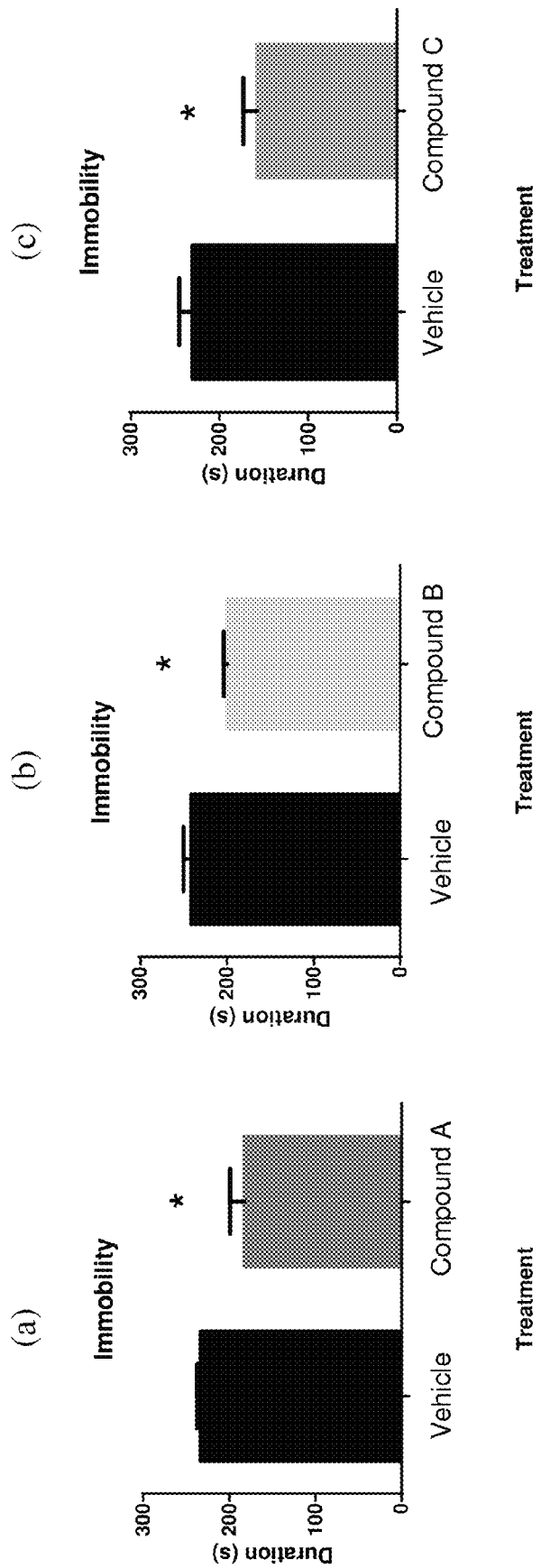
FIG. 9 depicts the results of in vivo Forced Swim Test measuring reduction of immobility in rats induced by different doses of Compound A, B or C.

In one study, reductions of the duration of immobility in rats induced by different doses of Compounds A, B and C were determined using the Forced Swim Test herein. Specifically, rats were administered with a vehicle (saline), Compound A, Compound B, or Compound C at a dose range between 0 and 10 mg/kg, and durations of immobility were recorded. The results of these experiments are set forth in FIG. 9. Maximal effects of Compounds A, B and C in the Forced Swim Test are shown in FIGS. 9(*a*), 9(*b*) and 9(*c*), respectively. Compounds A, B and C significantly ($p<0.05$) decreased immobility time in the Forced Swim Test compared to saline treated controls. The reductions of immobility indicate that Compounds A, B and C will likely improve depressive-like behavior.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

INCORPORATION BY REFERENCE

The entire contents of all patents, published patent applications and other references cited herein are hereby expressly incorporated herein in their entireties by reference.

The invention claimed is:

1. A method of treating a depressive symptom in a subject comprising administering to the subject a compound of Formula I:

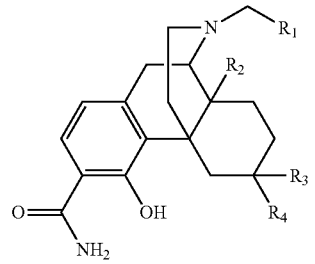

or a pharmaceutically acceptable salt thereof, wherein
R₁ is cyclobutyl,

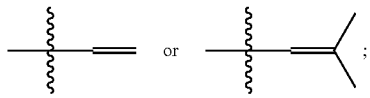

R₂ is H, hydroxyl, or methoxy; and
R₃ and R₄ are each, independently, H, hydroxyl, or NR₅R₆, wherein R₅ and R₆ are each independently H, alkyl or optionally substituted acyl, or alternatively, R₃ and R₄, together with the carbon atom to which they are attached, form C=O or C=CH₂;
wherein the depressive symptom is selected from the group consisting of depressed mood, loss of pleasure, post-partum depression, adjustment disorders with depressed mood, bereavement, bipolar I disorder, bipolar II disorder, cyclothymia, dysthymia, depression, dysthymic disorder, mixed mania, post-traumatic stress disorder, and seasonal affective disorder.

2. The method according to claim 1, wherein the compound of Formula I is:

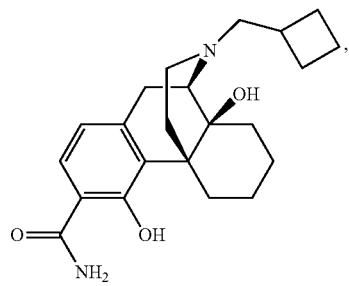

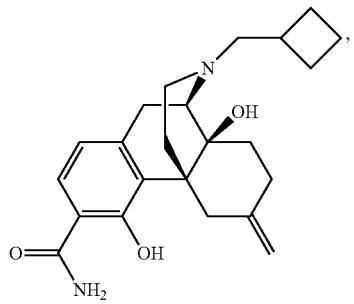

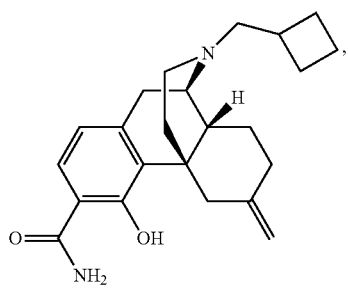

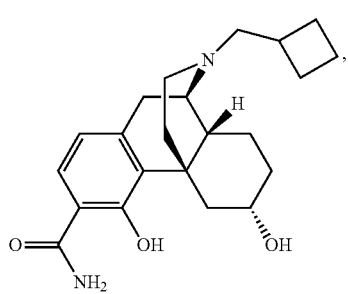

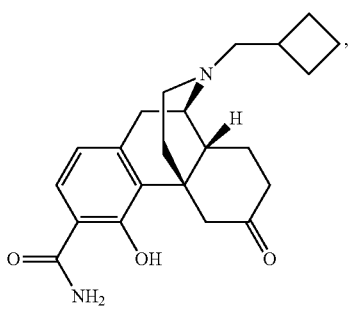

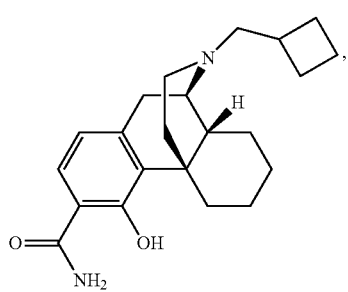

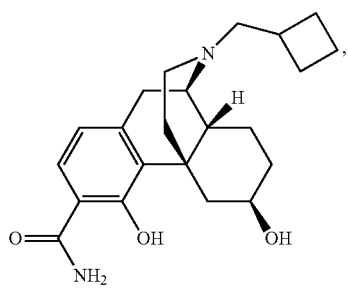

or a pharmaceutically acceptable salt thereof.

3. The method of claim 1, wherein the compound of Formula I exhibits an Emax of 5% to 45% in a GTPγS binding assay.

4. The method of claim 3, wherein the Emax is 15% to 35% in a GTPγS binding assay.

5. The method of claim 3, wherein the compound of Formula I has a low risk of opioid dependence, opioid addiction, or symptoms of opioid withdrawal.

6. The method of claim 1, wherein the compound of Formula I exhibits a maximal dopamine efflux in the nucleus accumbens of 125% to 300% over base line in a rat.

7. The method of claim 1, wherein the compound does not attenuate thermal pain in a rodent hot plate model when administered at a dose of at least 1 mg/kg.

8. The method of claim 1, wherein the depressive symptom is depressed mood, loss of pleasure, or post-partum depression.

9. The method of claim 1, wherein the depressive symptom is depression.

10. The method of claim 9, wherein the depression is major depressive disorder (MDD) or treatment-resistant disorder (TRD).

11. A method of treating a depressive symptom in a subject comprising administering to the subject a compound of Formula I:

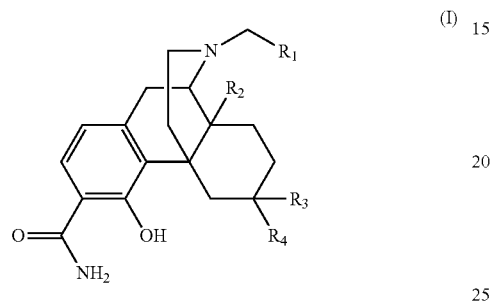

(I)

or a pharmaceutically acceptable salt thereof, wherein
R₁ is cyclobutyl,

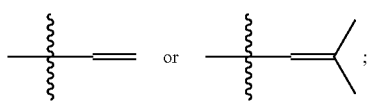

R₂ is H, hydroxyl, or methoxy; and
R₃ and R₄ are each, independently, H, hydroxyl, or NR₅R₆, wherein R₅ and R₆ are each independently H, alkyl or optionally substituted acyl, or alternatively, R₃ and R₄, together with the carbon atom to which they are attached, form C=O or C=CH₂;

wherein the depressive symptom is selected from the group consisting of acute stress disorder, anxiety disorder, Asperger syndrome, attention deficit, borderline personality disorder, fatigue, hyperactivity disorder, impulse control disorder, loss of appetite, obsessive-compulsive personality disorder (OCD), paranoid disorder, psychomotor changes, self-injury disorder, separation disorder, sleep disturbance, sleep disorder, substance-induced mood disorder, Tourette syndrome, tic disorder, and Trichotillomania.

12. The method of claim 11, wherein the depressive symptom is acute stress disorder, Asperger syndrome, attention deficit, borderline personality disorder, hyperactivity disorder, impulse control disorder, obsessive-compulsive personality disorder (OCD), paranoid disorder, self-injury disorder, separation disorder, sleep disorder, substance-induced mood disorder, Tourette syndrome, tic disorder, or Trichotillomania.

13. The method of claim 11, wherein the depressive symptom is an anxiety disorder, wherein the anxiety disorder is generalized anxiety disorder, panic, agoraphobia, acute stress, or post-traumatic stress disorder.

14. The method according to claim 11, wherein the compound of Formula I is:

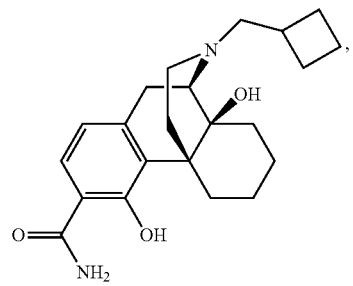

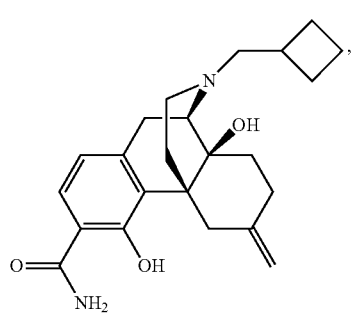

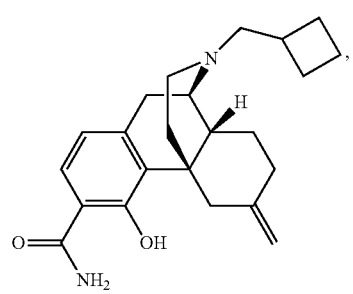

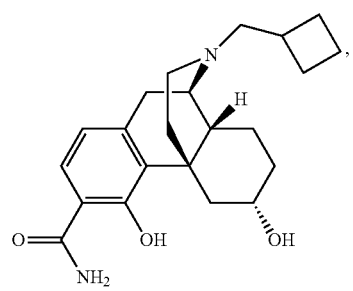

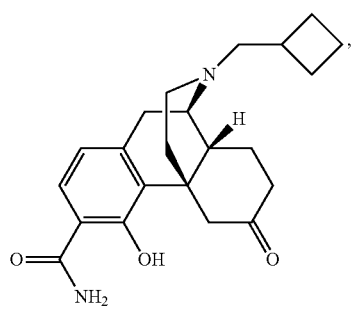

107
-continued
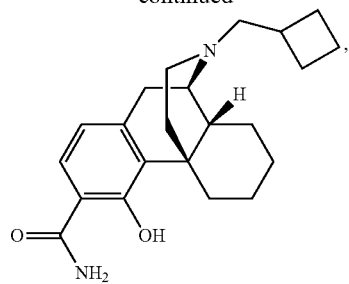
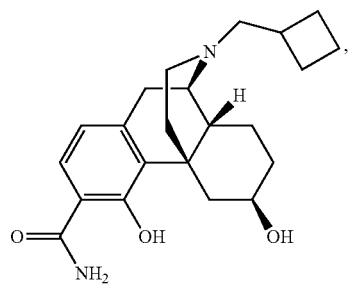
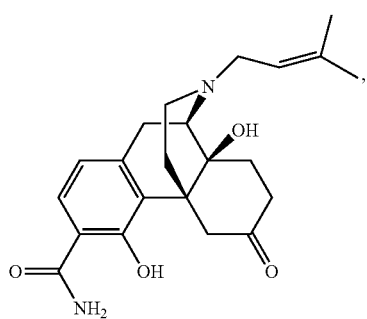
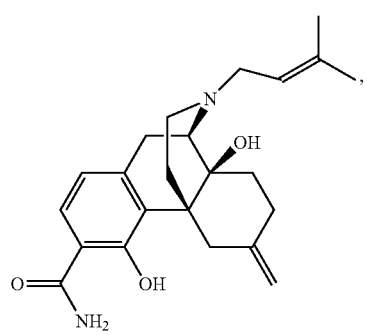
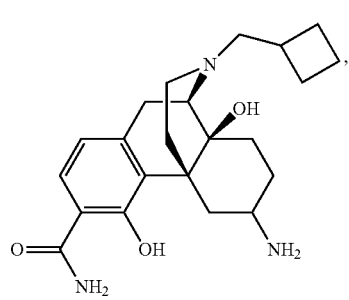
108
-continued
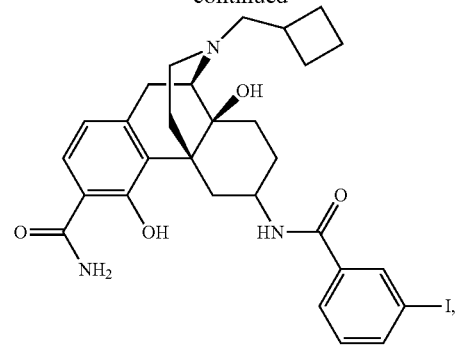
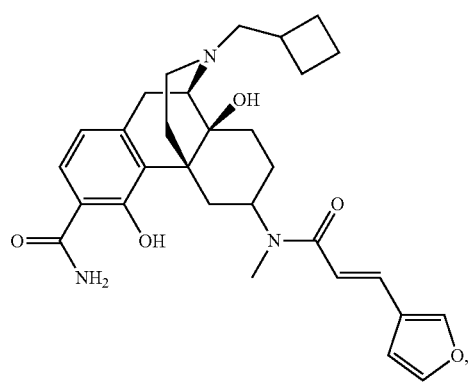
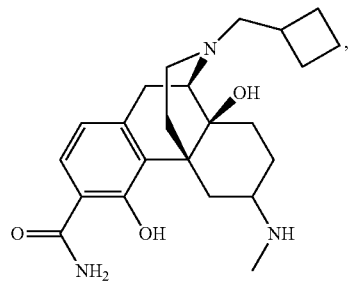
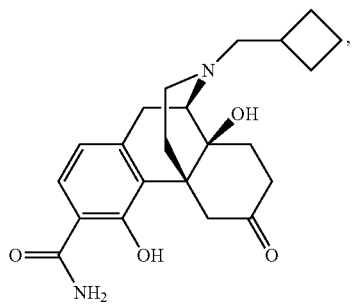
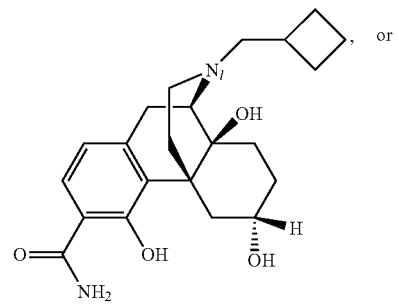

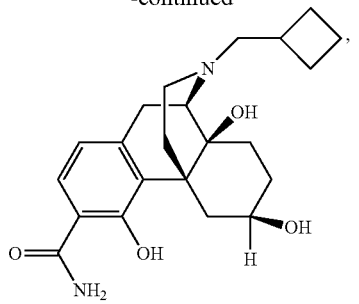

or a pharmaceutically acceptable salt thereof.

15. The method of claim 11, wherein the compound of Formula I exhibits an Emax of 5% to 45% in a GTPγS binding assay.

16. The method of claim 15, wherein the Emax is 15% to 35% in a GTPγS binding assay.

17. The method of claim 15, wherein the compound of Formula I has a low risk of opioid dependence, opioid addiction, or symptoms of opioid withdrawal.

18. The method of claim 11, wherein the compound of Formula I exhibits a maximal dopamine efflux in the nucleus accumbens of 125% to 300% over base line in a rat.

19. The method of claim 11, wherein the compound does not attenuate thermal pain in a rodent hot plate model when administered at a dose of at least 1 mg/kg.

* * * * *